(12) United States Patent
Tolkowsky et al.

(10) Patent No.: US 12,171,608 B2
(45) Date of Patent: *Dec. 24, 2024

(54) APPARATUS AND METHODS FOR USE WITH IMAGE-GUIDED SKELETAL PROCEDURES

(71) Applicant: Vuze Medical Ltd., Tel Aviv (IL)

(72) Inventors: David Tolkowsky, Tel Aviv (IL); Ran Cohen, Petah Tikva (IL)

(73) Assignee: Vuze Medical Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/377,568

(22) Filed: Oct. 6, 2023

(65) Prior Publication Data

US 2024/0138794 A1     May 2, 2024

Related U.S. Application Data

(63) Continuation of application No. 17/851,964, filed on Jun. 28, 2022, now Pat. No. 11,806,183, which is a
(Continued)

(51) Int. Cl.
*A61B 8/00*     (2006.01)
*A61B 6/46*     (2024.01)
(Continued)

(52) U.S. Cl.
CPC .............. *A61B 6/505* (2013.01); *A61B 6/466* (2013.01); *A61B 34/10* (2016.02); *A61B 34/20* (2016.02);
(Continued)

(58) Field of Classification Search
CPC ............................. A61B 6/505; A61B 16/466
See application file for complete search history.

(56) References Cited

U.S. PATENT DOCUMENTS

| 4,905,267 A | 2/1990 | Miller et al. |
| 4,985,019 A | 1/1991 | Michelson |

(Continued)

FOREIGN PATENT DOCUMENTS

| CN | 104637061 | 5/2015 |
| EP | 1504726 | 2/2005 |

(Continued)

OTHER PUBLICATIONS

U.S. Appl. No. 62/307,514, filed Mar. 13, 2016, Tolkowsky.
(Continued)

*Primary Examiner* — Joel F Brutus
(74) *Attorney, Agent, or Firm* — Fish & Richardson P.C.

(57) ABSTRACT

3D image data of a skeletal portion is acquired. While a portion of a tool is disposed at a first location along an insertion path, first and second x-rays are acquired from first and second image views. A processor registers the x-rays with the 3D image data, identifies a location of a tool within the x-rays, and computes an anticipated forward path of the tool within the 3D image data from the x-rays. The tool is moved to a second location along the insertion path and an additional x-ray is acquired from a single image view. The processor facilitates identifying if the tool has deviated from the anticipated forward path by registering the additional x-ray to the 3D image data and identifying a location of the portion of the tool within the additional x-ray. Other embodiments are also described.

19 Claims, 45 Drawing Sheets

Related U.S. Application Data continuation of application No. 16/629,449, filed as application No. PCT/IL2018/050732 on Jul. 5, 2018, now Pat. No. 11,406,338.

(60) Provisional application No. 62/641,359, filed on Mar. 11, 2018, provisional application No. 62/599,802, filed on Dec. 18, 2017, provisional application No. 62/556,436, filed on Sep. 10, 2017, provisional application No. 62/530,123, filed on Jul. 8, 2017.

(51) Int. Cl.
  *A61B 6/50* (2024.01)
  *A61B 34/10* (2016.01)
  *A61B 34/20* (2016.01)
  *A61B 34/30* (2016.01)
  *A61B 90/00* (2016.01)
  *G06N 20/00* (2019.01)

(52) U.S. Cl.
  CPC ............. *A61B 34/30* (2016.02); *A61B 90/36* (2016.02); *A61B 90/39* (2016.02); *G06N 20/00* (2019.01); *A61B 2034/105* (2016.02); *A61B 2034/107* (2016.02); *A61B 2034/2051* (2016.02); *A61B 2034/2055* (2016.02); *A61B 2034/303* (2016.02); *A61B 2090/364* (2016.02); *A61B 2090/367* (2016.02); *A61B 2090/3937* (2016.02); *A61B 2090/3966* (2016.02)

(56) References Cited

U.S. PATENT DOCUMENTS

| | | |
|---|---|---|
| 6,782,287 B2 | 8/2004 | Grzeszczuk et al. |
| 7,570,791 B2 | 8/2009 | Frank et al. |
| 7,853,311 B1 | 12/2010 | Webb |
| 8,036,441 B2 | 10/2011 | Frank et al. |
| 8,463,010 B2 | 6/2013 | Batman et al. |
| 9,240,046 B2 | 1/2016 | Carrell et al. |
| 9,262,830 B2 | 2/2016 | Bakker et al. |
| 9,401,020 B1 | 7/2016 | Li et al. |
| 9,427,286 B2 | 8/2016 | Siewerdsen et al. |
| 10,022,098 B2 | 7/2018 | Kleinszig et al. |
| 10,083,511 B2 | 9/2018 | Baumgart |
| 10,478,148 B2 | 11/2019 | Siewerdsen et al. |
| 10,716,631 B2 | 7/2020 | Tolkowsky |
| 10,846,893 B2 | 11/2020 | Weingarten et al. |
| 10,867,436 B2 | 12/2020 | Oved |
| 11,013,480 B2 | 5/2021 | Popovic et al. |
| 11,071,509 B2 | 7/2021 | Averbuch |
| 11,224,483 B2 | 1/2022 | Steinberg et al. |
| 11,406,338 B2 | 8/2022 | Tolkowsky |
| 11,452,570 B2 | 9/2022 | Tolkowsky |
| 11,490,967 B2 | 11/2022 | Tolkowsky |
| 11,806,183 B2 | 11/2023 | Tolkowsky |
| 2002/0038118 A1 | 3/2002 | Sholham |
| 2003/0130576 A1 | 7/2003 | Seeley et al. |
| 2003/0208122 A1 | 11/2003 | Melkent et al. |
| 2004/0103903 A1 | 6/2004 | Falahee |
| 2004/0127824 A1 | 7/2004 | Falahee |
| 2004/0215071 A1 | 10/2004 | Frank et al. |
| 2005/0272991 A1 | 12/2005 | Xu et al. |
| 2007/0055215 A1 | 3/2007 | Tran et al. |
| 2007/0100223 A1 | 5/2007 | Liao et al. |
| 2007/0167801 A1 | 7/2007 | Webler et al. |
| 2008/0118115 A1 | 5/2008 | Williamson |
| 2008/0262345 A1 | 10/2008 | Fichtinger et al. |
| 2009/0003523 A1 | 1/2009 | Raanes et al. |
| 2009/0082660 A1 | 3/2009 | Rahn et al. |
| 2009/0274271 A1 | 11/2009 | Pfister et al. |
| 2010/0106010 A1 | 4/2010 | Rubner et al. |
| 2010/0161022 A1 | 6/2010 | Tolkowsky |
| 2011/0152676 A1 | 6/2011 | Groszmann et al. |
| 2012/0155609 A1 | 6/2012 | Lemminger et al. |
| 2012/0230565 A1 | 9/2012 | Steinberg et al. |
| 2012/0289826 A1 | 11/2012 | Graumann et al. |
| 2015/0043798 A1* | 2/2015 | Carrell ............. G06T 7/73 382/131 |
| 2015/0085981 A1 | 3/2015 | Siewerdsen et al. |
| 2015/0100066 A1 | 4/2015 | Kostrzeski et al. |
| 2015/0125033 A1 | 5/2015 | Murphy et al. |
| 2015/0150523 A1 | 6/2015 | Sirpad et al. |
| 2015/0201892 A1 | 7/2015 | Hummel et al. |
| 2015/0282889 A1 | 10/2015 | Cohen et al. |
| 2016/0081762 A1 | 3/2016 | Stein et al. |
| 2016/0100911 A1 | 4/2016 | O'Neill |
| 2016/0191887 A1 | 6/2016 | Casas |
| 2016/0210742 A1 | 7/2016 | Weiss |
| 2016/0302747 A1 | 10/2016 | Averbuch |
| 2016/0310097 A1 | 10/2016 | Bae et al. |
| 2016/0374764 A1 | 12/2016 | Kemp et al. |
| 2017/0007334 A1 | 1/2017 | Crawford et al. |
| 2017/0084022 A1 | 3/2017 | Naidu et al. |
| 2017/0128041 A1 | 5/2017 | Hasser et al. |
| 2017/0156800 A1 | 6/2017 | Brown |
| 2017/0164920 A1 | 6/2017 | Lavallee et al. |
| 2017/0165008 A1 | 6/2017 | Finley |
| 2017/0258533 A1 | 9/2017 | Crawford et al. |
| 2017/0348061 A1 | 12/2017 | Joshi et al. |
| 2018/0040147 A1 | 2/2018 | Alhrishy et al. |
| 2018/0153626 A1 | 6/2018 | Yang et al. |
| 2018/0263706 A1 | 9/2018 | Averbuch |
| 2019/0209080 A1 | 7/2019 | Gullotti et al. |
| 2019/0350657 A1 | 11/2019 | Tolkowsky |
| 2020/0053335 A1 | 2/2020 | Casas |
| 2020/0305985 A1 | 10/2020 | Tolkowsky |
| 2020/0405399 A1 | 12/2020 | Steinberg et al. |
| 2021/0077047 A1 | 3/2021 | Tolkowsky |
| 2021/0386480 A1 | 12/2021 | Tolkowsky et al. |
| 2022/0110698 A1 | 4/2022 | Tolkowsky et al. |
| 2022/0133412 A1 | 5/2022 | Tolkowsky et al. |
| 2022/0249175 A1 | 8/2022 | Tolkowsky |
| 2022/0323033 A1 | 10/2022 | Tolkowsky |
| 2023/0027758 A1 | 1/2023 | Tolkowsky |
| 2023/0240628 A1 | 8/2023 | Cohen et al. |
| 2023/0380909 A1 | 11/2023 | Tolkowsky |

FOREIGN PATENT DOCUMENTS

| | | |
|---|---|---|
| EP | 3524157 | 8/2019 |
| WO | WO 2012/071566 | 5/2012 |
| WO | WO 2015/101948 | 7/2015 |
| WO | WO 2015/185503 | 12/2015 |
| WO | WO 2016/113165 | 7/2016 |
| WO | WO 2017/106357 | 6/2017 |
| WO | WO 2017/158592 | 9/2017 |
| WO | WO 2018/129532 | 7/2018 |
| WO | WO 2019/012520 | 1/2019 |
| WO | WO 2020/105049 | 5/2020 |

OTHER PUBLICATIONS

U.S. Appl. No. 62/334,463, filed May 11, 2016, Tolkowsky.
U.S. Appl. No. 62/362,607, filed Jul. 15, 2016, Tolkowsky.
U.S. Appl. No. 62/398,085, filed Sep. 22, 2016, Tolkowsky.
U.S. Appl. No. 62/439,495, filed Dec. 28, 2016, Tolkowsky.
U.S. Appl. No. 62/463,747, filed Feb. 27, 2017, Tolkowsky.
U.S. Appl. No. 62/530,123, filed Jul. 8, 2017, Tolkowsky.
U.S. Appl. No. 62/556,436, filed Sep. 10, 2017, Tolkowsky.
U.S. Appl. No. 62/599,802, filed Dec. 18, 2017, Tolkowsky.
U.S. Appl. No. 62/641,359, filed Mar. 11, 2018, Tolkowsky.
U.S. Appl. No. 62/770,758, filed Nov. 22, 2018, Tolkowsky.
U.S. Appl. No. 62/883,669, filed Aug. 7, 2019, Tolkowsky.
U.S. Appl. No. 62/909,791, filed Oct. 3, 2019, Tolkowsky.
U.S. Appl. No. 63/091,351, filed Oct. 14, 2020, Tolkowsky et al.
U.S. Appl. No. 63/130,877, filed Dec. 28, 2020, Tolkowsky et al.
U.S. Appl. No. 63/164,349, filed Mar. 22, 2021, Cohen et al.
"3-D Imaging Techniques Transform Cardiac Catheterization," UCLA Health, Jan. 1, 2014.

(56) References Cited

OTHER PUBLICATIONS

"Carestream DirectView DR Long-Length Imaging System with Automatic and Manual Stitching"—Carestream Health (2012).

Abe et al., "A novel 3D guidance system using augmented reality for percutaneous vertebroplasty," Journal of Neurosurgery Spine, 2013, 19(4):492-501.

Anderst et al., "Six-degrees-of-freedom cervical spine range of motion during dynamic flexion-extension after single-level anterior arthrodesis: comparison with asymptomatic control subjects," The Journal of bone and joint surgery, 2013, 95(6):497-506.

Bifulco et al., "Simulation of the radiography formation process from CT patient volume," University of Naples "Federico II", Electronic Engineering Dept., Bioengineering Unit, 1998.

Brown et al., "Registration of planar film radiographs with computed tomography," IEEE Workshop on Mathematical Methods Biomedical Imaging, 1996.

Chang et al., "Registration of 2D C-Arm and 3D CT images for a C-Arm image-assisted navigation system for spinal surgery," Applied bionics and biomechanics, 2015, 2015(478062): 9 pages.

Chen et al., "Learning to Predict 3D Objects with an Interpolation-Based differentiable Renderer," Advances in neural information processing systems, 2019, 12 pages.

Chen et al., "Ruler based automatic C-arm image stitching without overlapping constraint," Roboter-Assistenten werden sensitiv, 2015, 212-215.

Cheng et al., "Deep similarity learning for multimodal medical images," Computer Methods in Biomechanics and Biomedical Engineering: Imaging & Visualization, 2016, 6(3):248-252.

De Silva et al., "Development and Clinical Translation of the "Level Check" Registration Algorithm for Decision Support in Spine Surgery," presented at Radiological Society of North America (RSNA) 2016 annual meeting, Nov. 29, 2016.

Elmi-Terander et al., "Surgical navigation technology based on augmented reality and integrated 3D intraoperative imaging: a spine cadaveric feasibility and accuracy study," Spine, 2016, 41(21):E1303-E1311.

Extended European Search Report in European Appln. No. 18831854.7, mailed on Mar. 12, 2021, 11 pages.

Extended European Search Report in European Appln. No. 19887268.1, mailed on Jul. 25, 2022, 8 pages.

Extended European Search Report in European Appln. No. 21214161.8, mailed on Mar. 17, 2022, 7 pages.

Freiman et al., "Spectral-based 2D/3D X-ray to CT image rigid registration," Medical Imaging 2011: Visualization, Image-Guided Procedures, and Modeling. vol. 7964, International Society for Optics and Photonics, 2011.

Glocker et al., "Automatic localization and identification of vertebrae in arbitrary field-of-view CT scans," International Conference on Medical Image Computing and Computer-Assisted Intervention. Springer, Berlin, Heidelberg, 2012.

Goerres et al., "Deformable 3D-2D registration for guiding K-wire placement in pelvic trauma surgery," Medical Imaging 2017: Image-Guided Procedures, Robotic Interventions, and Modeling. vol. 10135, International Society for Optics and Photonics, 2017.

Gooßen et al., "Automatic stitching of digital radiographies using image interpretation," Proceedings of the 5th International Conference on Image Analysis and Recognition. Berlin: Springer Verlag. 2008.

Gooßen et al., "Ruler-based automatic stitching of spatially overlapping radiographs," Bildverarbeitung für die Medizin 2008, Springer, Berlin, Heidelberg, 2008, 192-196.

Hart et al., "Reduction of radiation exposure by the use of fluoroscopic guidance in transpedicular instrumentation," Acta Chir Orthop Traumatol Cech, 2001, 78(5):447-450 (Abstract).

International Search Report and Written Opinion in International Appln. No. PCT/IL2018/050732, mailed on Oct. 8, 2018, 16 pages.

International Search Report and Written Opinion in International Appln. No. PCT/IL2019/051272, mailed on Mar. 8, 2020, 27 pages.

International Search Report and Written Opinion in International Appln. No. PCT/IL2021/051218, mailed on Mar. 3, 2022, 26 pages.

International Search Report and Written Opinion in International Appln. No. PCT/US2016/066672, mailed on Feb. 21, 2017, 6 pages.

Jonic et al., "Multiresolution spline-based 3D/2D registration of CT volume and C-arm images for computer-assisted surgery," Medical Imaging, 2001: Image Processing, vol. 4322, presented at International Society for Optics and Photonics, 2001.

Joskowicz, "Computer Assisted Surgery Lectures Fluoro X-ray to CT rigid registration," School of Engineering and Computer Science, the Hebrew University of Jerusalem, Isreal, 2009.

Markelj et al., "A review of 3D/2D registration methods for image-guided interventions," Medical image analysis, 2012, 16(3):642-661.

Markelj et al., "Robust gradient-based 3-D/2-D registration of CT and MR to X-ray images," IEEE Transactions on Medical Imaging, 2008, 27(12):1704-1714.

Navab et al., "Merging visible and invisible: Two camera-augmented mobile C-arm (CAMC) applications," Proceedings 2nd IEEE and ACM International Workshop on Augmented Reality (IWAR'99), IEEE, 1999, 8 pages.

Notice of Allowance in U.S. Appl. No. 16/083,247, mailed on May 12, 2020, 15 pages.

Notice of Allowance in U.S. Appl. No. 16/629,449, mailed on Apr. 27, 2022, 9 pages.

Notice of Allowance in U.S. Appl. No. 16/629,449, mailed on May 19, 2022, 5 pages.

Notice of Allowance in U.S. Appl. No. 16/901,513, mailed on Jul. 5, 2022, 13 pages.

Notice of Allowance in U.S. Appl. No. 17/021,324, mailed on Nov. 24, 2021, 9 pages.

Notice of Allowance in U.S. Appl. No. 17/710,185, mailed on Aug. 18, 2022, 15 pages.

Notice of Allowance in U.S. Appl. No. 17/710,185, mailed on Jun. 7, 2022, 19 pages.

Notice of Allowance in U.S. Appl. No. 17/851,964, mailed on Jul. 14, 2023, 8 pages.

Notice of Allowance in U.S. Appl. No. 18/233,667, mailed on Oct. 17, 2023, 16 pages.

Office Action in Chinese Appln. No. 201780029652.X, dated Aug. 11, 2021, 9 pages (with English Translation).

Office Action in European Appln. No. 17713470.7, mailed on Jul. 6, 2020, 5 pages.

Office Action in Indian Patent Application No. 202027005043, dated Feb. 28, 2022, 7 pages (with English Translation).

Office Action in U.S. Appl. No. 17/021,324, mailed on Feb. 4, 2021, 28 pages.

Office Action in U.S. Appl. No. 17/557,633, mailed on Jul. 26, 2022, 22 pages.

Office Action in U.S. Appl. No. 17/557,633, mailed on Mar. 16, 2022, 33 pages.

Office Action in U.S. Appl. No. 17/578,974, mailed on Jul. 12, 2022, 15 pages.

Office Action in U.S. Appl. No. 17/578,974, mailed on Mar. 21, 2022, 23 pages.

Office Action in U.S. Appl. No. 16/629,449, mailed on Mar. 3, 2022, 7 pages.

Office Action in U.S. Appl. No. 17/021,324, mailed onMay 25, 2021, 20 pages.

Office Action in U.S. Appl. No. 17/295,221, mailed on Sep. 26, 2023, 9 pages.

Office Action in U.S. Appl. No. 17/851,964, mailed on Mar. 31, 2023, 8 pages.

Office Action in U.S. Appl. No. 17/959,062, mailed on Nov. 9, 2023, 17 pages.

Office Action in U.S. Appl. No. 18/297,802, mailed on Sep. 13, 2023, 25 pages.

OrthoSpineNews [online], "Zebra Medical Vision Secures a 7th FDA Clearance for Its Patented Breakthrough in Orthopedic Surgery Planning," Dec. 8, 2020, retrieved on Dec. 27, 2020, retrieved from URL<https://orthospinenews.com/2020/12/08/zebra-medical-vision-secures-a-7th-fda-clearance-for-its-patented-breakthrough-in-orthopedic-surgery-planning/>, 3 pages.

(56) References Cited

OTHER PUBLICATIONS

Otake et al., "Automatic Localization of Vertebral Levels in X-Ray Fluoroscopy Using 3D-2D Registration: A Tool to Reduce Wrong-Site Surgery," Phys Med Biol., Sep. 7, 2012, 57(17):5485-5508.

Otake et al., "Intraoperative image-based multiview 2D/3D registration for image-guided orthopaedic surgery: incorporation of fiducial-based C-arm tracking and GPU-acceleration," IEEE transactions on medical imaging, 2012, 31(4):948-962.

Rohlfing et al., "Progressive attenuation fields: Fast 2D-3D image registration without precomputation," Medical Physics, Sep. 2005, 32(9):2870-2880.

Russakoff et al., "Fast calculation of digitally reconstructed radiographs using light fields," Medical Imaging 2003: Image Processing. vol. 5032. International Society for Optics and Photonics, 2003.

Russakoff et al., "Fast generation of digitally reconstructed radiographs using attenuation fields with application to 2D-3D image registration," IEEE transactions on medical imaging, 2005, 24(11):1441-1454.

Russakoff et al., "Fast intensity-based 2D-3D image registration of clinical data using light fields," Proceedings of the Ninth International Conference on Computer Vision, 2003.

Russakoff et al., "Intensity-based 2D-3D spine image registration incorporating one fiducial marker," International Conference on Medical Image Computing and Computer-Assisted Intervention, Springer, Berlin, Heidelberg, 2003.

Sakai et al., "Simultaneous Registration With CT-Fluoro Matching for Spinal Navigation Surgery," Nagoya J. Med. Sci, 2006, 68:45-52.

Table of contents from 2001 IEEE Computer Science Conference on Computer Vision and Pattern Recognition, dated Dec. 8-14, 2001.

Toews et al., "A feature-based approach to big data analysis of medical images," International Conference on Information Processing in Medical Imaging, Springer, Cham, 2015.

Tomazevic et al. "3-D/2-D registration of CT and MR to X-ray images." IEEE transactions on medical imaging, 2003, 22(11):1407-1416.—abstract.

Tomaževič, "3D/2D Registration of medical images," Utrecht University, 2008.

Tomazevic, Dejan, and Franjo Pernus. "Robust gradient-based 3-D/2-D registration of CT and MR to X-ray images." IEEE Transactions on Medical Imaging 27.12 (2008): 1704-1714.

Touchette, "Artificial X-ray imaging system (AXIS)-design and evaluation on C-arm performance in operating room and educational settings," Doctoral dissertation, University of British Columbia, 2017, 127 pages.

Uneri et al., "Deformable 3D-2D registration of known components for image guidance in spine surgery," International Conference on Medical Image Computing and Computer-Assisted Intervention. Springer, Cham, 2016.

Uneri et al., "Image-Based Known-Component Registration for Surgical Guidance," presented at 2017 Image Guided Therapy (IGT) Workshop, Mar. 15, 2017.

Whitmarsh et al., "3D reconstruction of the lumbar vertebrae from anteroposterior and lateral dual-energy X-ray absorptiometry," Medical image analysis, 2013, 17(4):475-487.

Wu et al., "Scalable high-performance image registration framework by unsupervised deep feature representations learning," IEEE Transactions on Biomedical Engineering, 2016, 63(7):1505-1516.

Yaniv, "Registration for orthopaedic interventions," Computational Radiology for Orthopaedic Interventions, Springer, Cham, 2016, 41-70.

Zöllei et al., "2D-3D Rigid Registration of X-Ray Fluoroscopy and CT Images Using Mutual Information and Sparsely Sampled Histogram Estimators," Artificial Intelligence Laboratory, MIT Cambridge, MA 02139, 2001.

Zollei et al., "2D-3D rigid registration of X-ray fluoroscopy and CT images using mutual information and sparsely sampled histogram estimators," Computer Vision and Pattern Recognition, 2001, CVPR 2001, Proceedings of the 2001 IEEE Computer Society Conference on. vol. 2. IEEE, 2001 (Abstract).

\* cited by examiner

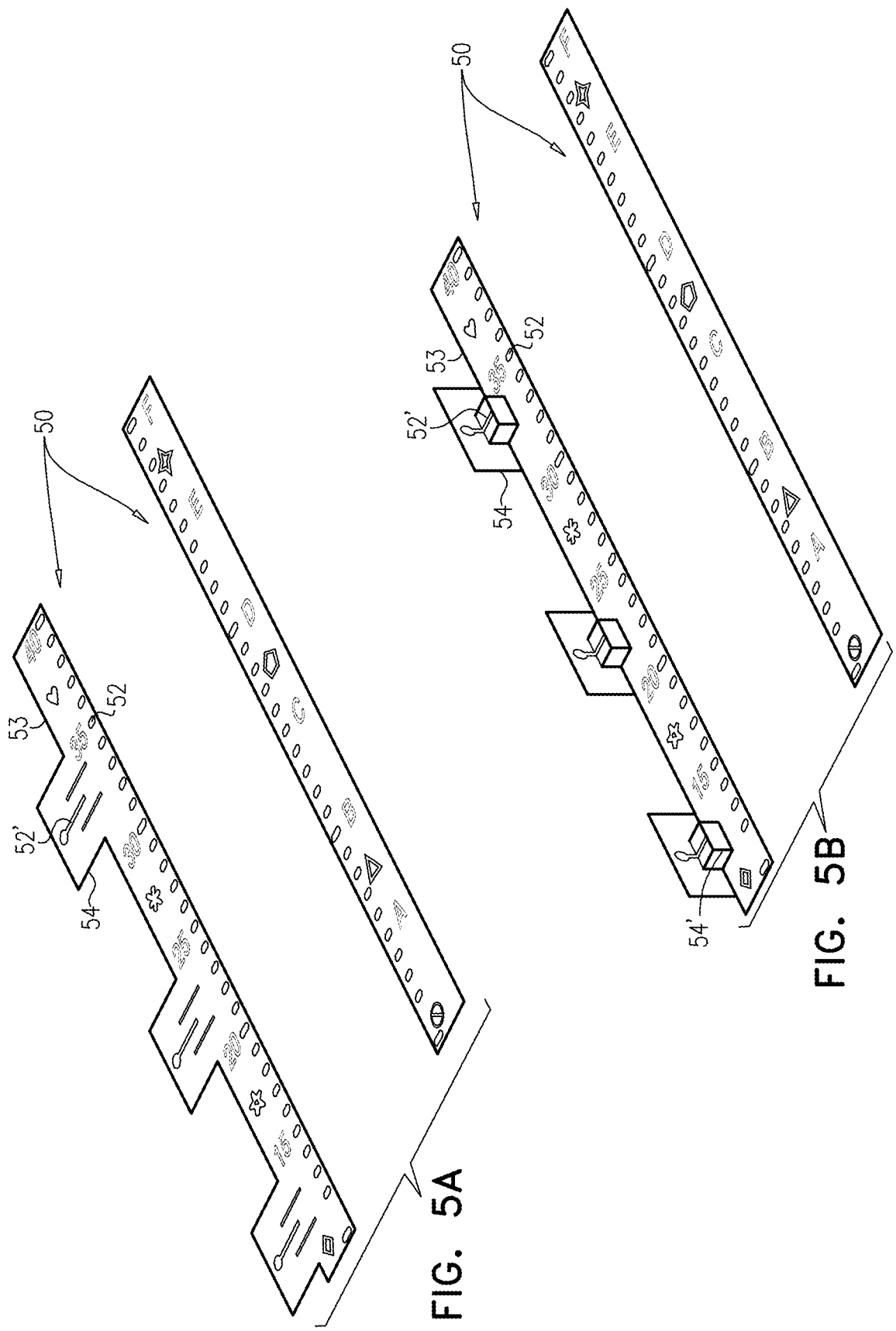

210   200

APPARATUS AND METHODS FOR USE WITH IMAGE-GUIDED SKELETAL PROCEDURES

CROSS-REFERENCE TO RELATED APPLICATIONS

The present application is a Continuation of U.S. Ser. No. 17/851,964 to Tolkowsky, filed Jun. 28, 2022, which issued as U.S. Pat. No. 11,806,183 to Tolkowsky, which is a Continuation of U.S. Ser. No. 16/629,449 to Tolkowsky, filed Jan. 8, 2020, which issued as U.S. Pat. No. 11,406,338 to Tolkowsky and which is the US national stage application of PCT/IL2018/050732, filed Jul. 5, 2018, which published as PCT Publication WO 2019/012520 to Tolkowsky et al., and which claims the priority of the following applications, all of which are incorporated herein by reference:

- U.S. 62/530,123 to Tolkowsky et al., filed Jul. 8, 2017, entitled, "Apparatus and methods for use with image-guided skeletal procedures,"
- U.S. 62/556,436 to Tolkowsky et al., filed Sep. 10, 2017, entitled, "Apparatus and methods for use with image-guided skeletal procedures,"
- U.S. 62/599,802 to Tolkowsky et al., filed Dec. 18, 2017, entitled, "Apparatus and methods for use with image-guided skeletal procedures," and
- U.S. 62/641,359 to Tolkowsky et al., filed Mar. 11, 2018, entitled, "Apparatus and methods for use with image-guided skeletal procedures."

FIELD OF EMBODIMENTS OF THE INVENTION

Some applications of the present invention generally relate to medical apparatus and methods. Specifically, some applications of the present invention relate to apparatus and methods for use in procedures that are performed on skeletal anatomy.

BACKGROUND

Approximately 5 million spine surgeries are performed annually worldwide. Traditional, manual surgery is known as freehand surgery. Typically, for such procedures, a 3D scan (e.g., a CT and/or MRI) scan is performed prior to surgery. A CT scan is typically performed for bony tissue (e.g., vertebra), and an MRI scan is typically performed for soft tissue (e.g., discs).

Reference is made to FIG. 1A, which is a schematic illustration of a typical set up of an orthopedic operating room, for procedures that are performed in a freehand manner. Typically, in freehand procedures, although the CT and/or MRI scan is examined by the surgeon when preparing for surgery, no use is made of the CT and/or MRI images during surgery, other than potentially as a general reference that may be viewed occasionally. Rather, the surgery is typically performed under 2D x-ray image guidance, the 2D x-rays typically being acquired using an x-ray C-arm. FIG. 1A shows a surgeon 10 performing a procedure using intraprocedural x-ray images that are acquired by a C-arm 34, and displayed on a display 12. Freehand surgery in which there is significant use of x-rays is known as fluoroscopy-guided surgery. X-ray C-arms are ubiquitous, familiar to surgeons, useful for acquiring real-time images, tool-neutral (i.e., there is no requirement to use only specific orthopedic tools that are modified specifically for imaging by that x-ray C-arm), and relatively inexpensive. A growing proportion of spinal surgeries are performed using a minimally-invasive surgery (also known as "MIS," or in the case of spine surgery, minimally-invasive spine surgery, which is also known as "MISS"), or "mini-open" surgery. In contrast to open surgery, in which an incision is typically made along the entire applicable segment of the spine upon which surgery is performed, in minimally-invasive surgery, very small incisions are made at the insertion point of tools. In "mini-open" surgery, incisions are made that are smaller than in open surgery and larger than in minimally-invasive surgery. Typically, the less invasive the type of surgery that is performed, the greater the use of x-ray imaging for assisting the procedure as the anatomy being operated on may not all be in the surgeon's direct line of sight. There is evidence that less invasive procedures that are performed under fluoroscopic guidance enable faster patient recovery compared with open procedures. However, the use of real-time fluoroscopic guidance typically exposes the patient, as well as the surgeon and the support staff to a relatively large amount of radiation.

A minority of procedures are performed using Computer Aided Surgery (CAS) systems that provide "GPS-like" navigation and/or robotics. Such systems typically make use of CT and/or MRI images that are generated before the patient is in the operating room, or when the patient is within the operating room, but typically before an intervention has commenced. The CT and/or MRI images are registered to the patient's body, and, during surgery, tools are navigated upon the images, the tools being moved manually, robotically or both.

Typically, in CAS procedures, a uniquely-identifiable location sensor is attached to each tool that needs to be tracked by the CAS system. Each tool is typically identified and calibrated at the beginning of the procedure. In addition, a uniquely-identifiable reference sensor is attached, typically rigidly, to the organ. In the case of spinal surgery, the reference sensor is typically drilled into, or fixated onto, the sacrum or spine, and, if surgery is performed along a number of vertebrae, the reference sensor is sometimes moved and drilled into a different portion of the spine, mid-surgery, in order to always be sufficiently close to the surgical site. The images to be navigated upon (e.g., CT, MRI), which are acquired before the patient is in the operating room, or when the patient is within the operating room, but before an intervention has commenced, are registered to the patient's body or a portion thereof. In order to register the images to the patient's body, the current location of the patient's body is brought into the same reference frame of coordinates as the images using the reference sensor. The location sensors on the tools and the reference sensor on the patient's body are then tracked, typically continuously, in order to determine the locations of the tools relative to the patient's body, and a symbolic representation of the tool is displayed upon the images that are navigated upon. Typically, the tool and the patient's body are tracked in 5-6 degrees of freedom.

There are various techniques that are utilized for the tracking of tools, as well as applicable portions of the patient's body, and corresponding location sensors are used for each technique. One technique is infrared ("IR") tracking, whereby an array of cameras track active IR lights on the tools and the patient's body, or an array of beams and cameras tracks passive IR reflectors on the tools and the patient's body. In both categories of IR tracking, lines of sight must be maintained at all times between the tracker and the tools. For example, if the line of sight is blocked by the surgeon's hands, this can interfere with the tracking. Another technique is electromagnetic or magnetic tracking, whereby a field generator tracks receivers, typically coils, on the tools and the patient's body. For those latter techniques, environmental interferences from other equipment must be avoided or accounted for. In each of the techniques, the location sensors of the navigation system are tracked using tracking components that would not be present in the operating room in the absence of the navigation system (i.e., the location sensors do not simply rely upon imaging by imaging devices that are typically used in an orthopedic operating room in the absence of the navigation system).

A further technique that can be used with a robotically-driven tool is to start with the tool at a known starting point relative to the patient's body, and to then record motion of the tool from the starting point. Alternatively, such tools can be tracked using the above-described techniques.

Given the nature of CAS procedures, the equipment required for such procedures is typically more expensive than that of non-CAS procedures (non-CAS procedures including open procedures, mini-open procedures, or minimally-invasive procedures that are not computer aided with respect to the guidance of tools). Such procedures typically limit tool selection to those fitted with location sensors as described above, and typically require such tools to be individually identified and calibrated at the beginning of each surgery.

SUMMARY OF EMBODIMENTS

In accordance with some applications of the present invention, the following steps are typically performed during procedures that are performed on skeletal anatomy, using a system that includes a computer processor. Such procedures may include joint (e.g., shoulder, knee, hip, and/or ankle) replacement, joint repair, fracture repair (e.g., femur, tibia, and/or fibula), a procedure that is performed on a rib (e.g., rib removal, or rib resection), and/or other interventions in which 3D image data are acquired prior to the intervention and 2D images are acquired during the intervention. For some applications, the steps are performed during a procedure that is performed on one or more vertebrae of a subject's spine and/or on other spinal elements.

Typically, in a first step, targeted vertebra(e) are marked by an operator, typically prior to the actual intervention, with respect to 3D image data (e.g., a 3D image, a 2D cross-section derived from 3D image data, and/or a 2D projection image derived from 3D image data) of the subject's spine. For some applications, pre-intervention planning is performed. For example, desired insertion points, incision areas, or tool trajectories may be planned and associated with the 3D image data. For some applications, in a second step, a radiopaque element, such as the tip of a surgical tool or a radiopaque marker, is placed in a vicinity of the subject, e.g., on the subject, underneath the subject, on the surgical table, or above the surgical table. Typically, in a third step, vertebrae of the spine are identified in order to verify that the procedure is being performed with respect to the correct vertebra (a step which is known as "level verification"), using radiographic images of the spine and the markers to facilitate the identification. For some applications, in a fourth step, an incision site (in the case of minimally-invasive surgery), or a tool entry point into a vertebra (in the case of open surgery) is determined upon the patient's body. In a fifth step, the first tool in the sequence of tools (which in the case of minimally-invasive or less-invasive surgery is typically a needle, e.g., a Jamshidi™ needle) is typically inserted into the subject (e.g., in the subject's back) via the incision site or the tool entry point, and is slightly fixated in the vertebra. In the case of more-invasive or open spinal surgery, such tool is typically a pedicle finder (which may also be known as a pedicle marker). Optionally, such tool is attached to a holder mechanism that is typically fixed to the surgical table but may also be fixed to a surface other than the surgical table, e.g., another table in the operating room, a stationary or movable stand, or imaging equipment inside the operating room. In a sixth step, two or more 2D radiographic images are typically acquired from respective views that typically differ by at least 10 degrees, e.g., at least 20 degrees (and further typically by 30 degrees or more), and one of which is typically from the direction of insertion of the tool. Typically, generally-AP and generally-lateral images are acquired. Alternatively or additionally, images from different views are acquired. Typically, in a seventh step, the computer processor registers the 3D image data to the 2D images.

Typically, 3D image data and 2D images of individual vertebrae are registered to each other. Further typically, the 3D image data and 2D images are registered to each other by generating a plurality of 2D projections from the 3D image data, and identifying respective first and second 2D projections that match each of the 2D x-ray images of the vertebra, as described in further detail hereinbelow. Typically, first and second 2D x-ray images of the vertebra are acquired using an x-ray imaging device that is unregistered with respect to the subject's body, or whose precise pose relative to the subject's body (and more specifically the applicable portion thereof) when acquiring images is not known or tracked, by (a) acquiring a first 2D x-ray image of the vertebra (and the tool positioned relative to the vertebra, or at least a portion of the tool inserted into the vertebra) from a first view, while the x-ray imaging device is disposed at a first pose with respect to the subject's body, (b) moving the x-ray imaging device to a second pose with respect to the subject's body, and (c) while the x-ray imaging device is at the second pose, acquiring a second 2D x-ray image of at least the portion of the tool and the vertebra from a second view. For some applications, more than two 2D x-rays are acquired from respective x-ray image views, and the 3D image data and 2D x-ray images are typically all registered to each other by identifying a corresponding number of 2D projections of the 3D image data that match respective 2D x-ray images.

For some applications, the "level verification" is performed using registration of the 2D x-ray images to the 3D image data. For example, the system may attempt to register each 2D x-ray with the targeted vertebra in the 3D image until a match is found. The targeted vertebra may now be marked in the 2D x-ray and can be seen with respect to a radiopaque element that is placed in the vicinity of the subject and appears in the same 2D x-ray. Additionally or alternatively, the system may take a plurality of 2D x-ray images, each one being of a different segment of the anatomy, e.g., skeletal portion of the body, e.g., spine, and register all of them to the 3D image data of the anatomy. Using post-registration correspondence of each 2D x-ray image to the 3D image data, the plurality of 2D x-ray images may be related to each other so as to create a combined 2D x-ray image of the anatomy.

For some applications, the computer processor acquires a 2D x-ray image of a tool inside, or relative to, the vertebra from only a single x-ray image view, and the 2D x-ray image is registered to the 3D image data by generating a plurality of 2D projections from the 3D image data, and identifying a 2D projection that matches the 2D x-ray image of the vertebra. In response to registering the 2D x-ray image to the 3D image data, the computer processor drives a display to display a cross-section derived from the 3D image data at a current location of a tip of the tool, as identified from the 2D x-ray image, and optionally to show a vertical line on the cross-sectional image indicating a line within the cross-sectional image somewhere along which the tip of the tool is currently disposed.

As described hereinabove, typically two or more 2D x-rays are acquired from respective x-ray image views, and the 3D image data and 2D images are typically registered to each other by identifying a corresponding number of 2D projections of the 3D image data that match the respective 2D x-ray images. Subsequent to the registration of the 3D image data to the 2D x-ray images, additional features of the system are applied by the computer processor. For example, the computer processor may drive the display to display the anticipated (i.e., extrapolated) path of the tool with reference to a target location and/or with reference to a desired insertion vector. For some applications, the computer processor simulates tool progress within a secondary 2D imaging view, based upon observed progress of the tool in a primary 2D imaging view. Alternatively or additionally, the computer processor overlays an image of the tool, a representation thereof, and/or a representation of the tool path, upon the 3D image data (e.g., a 3D image, a 2D cross-section derived from 3D image data, and/or a 2D projection image derived from 3D image data), the location of the tool or tool path having been derived from current 2D images.

For some applications, when more than one tool appear in the 2D x-rays, the system uses registration of two 2D x-ray images to 3D image data containing a pre-planned insertion path for each of the tools to automatically associate between (a) a tool in a first one of the 2D x-ray images and (b) the same tool in a second one of the 2D x-ray images.

As described hereinabove, for some applications, sets of markers are placed on the subject, underneath the subject, on the surgical table, or above the surgical table. Typically, the markers that are placed at respective locations with respect to the subject are identifiable in x-ray images, in optical images, and physically to the human eye. For example, respective radiopaque alphanumeric characters, arrangements of a discernible shape, or particular symbols, may be placed at respective locations. For some applications, markers placed at respective locations are identifiable based upon other features, e.g., based upon the dispositions of the markers relative to other markers. Using a radiographic imaging device, a plurality of radiographic images of the set of radiopaque markers are acquired, respective images being of respective locations along at least a portion of the subject's spine and each of the images including at least some of the radiopaque markers. Using the computer processor, locations of the radiopaque markers within the radiographic images are identified, by means of image processing. At least some of the radiographic images are combined with respect to one another based upon the identified locations of the radiopaque markers within the radiographic images. Typically, such combination of images is similar to stitching of images. However, the images may not necessarily be precisely stitched such as to stitch portions of the subject's anatomy in adjacent images to one another. Rather, the images are combined with sufficient accuracy to be able to determine a location of the given vertebra within the combined radiographic images. Also, the exact pose or spatial position of the imaging device (e.g., the x-ray c-arm) when acquiring any of the images, relative to the subject's body (and more specifically the applicable portion thereof), need not be known or tracked. The computer processor thus automatically determines (or facilitates manual determination of) a location of a given vertebra within the combined radiographic images.

Based upon the location of the given vertebra within the combined radiographic images, a location of the given vertebra in relation to the set of radiopaque markers that is placed on the subject is determined, as described in further detail hereinbelow. The markers are typically utilized to provide additional functionalities, or in some cases to facilitate functionalities, as described in further detail hereinbelow.

There is therefore provided, in accordance with some applications of the present invention, a method for performing a procedure with respect to a skeletal portion within a body of a subject, the method including:

acquiring 3D image data of at least the skeletal portion;
using at least one computer processor:
designating at least one point selected from the group consisting of (a) a skin-level incision point corresponding to the skeletal portion and (b) a skeletal-portion-level entry point within the body of the subject, and
associating the designated point with the 3D image data for the skeletal portion;
positioning a radiopaque element on the body of the subject with respect to the skeletal portion, the radiopaque element being visible to the naked eye;
acquiring an intraoperative 2D radiographic image of the skeletal portion, such that the radiopaque element appears in the 2D radiographic image;
using the at least one computer processor:
registering the 2D radiographic image to the 3D image data such that the designated point appears on the 2D radiographic image,
displaying a location of the designated point with respect to the radiopaque element on the 2D radiographic image.

For some applications, the skeletal portion is a vertebra of a spine of a subject.

For some applications, associating the designated point with the 3D image data includes storing the designated point as 3D coordinates within the 3D image data.

For some applications:
positioning the radiopaque element includes positioning a set of radiopaque markers on the body of the subject with respect to the skeletal portion, the radiopaque markers being visible to the naked eye, and
displaying the location of the designated point with respect to the radiopaque element includes displaying the location of the designated point with respect to the set of radiopaque markers on the 2D radiographic image.

For some applications, registering the 2D radiographic image to the 3D image data includes:
generating a plurality of 2D projections from the 3D image data; and
identifying a 2D projection that matches the 2D radiographic image of the skeletal portion.

For some applications, the method further includes, based on the location of the designated point with respect to the radiopaque element on the 2D radiographic image, labeling a location of the designated point on the subject's body.

There is further provided, in accordance with some applications of the present invention, apparatus for performing a procedure on a skeletal portion within a body of a subject, the apparatus comprising:

a radiopaque marker configured to be attached to a surface of the subject in a vicinity of the skeletal portion such that the radiopaque marker appears in radiographic images of the skeletal portion that are acquired from a first image view, the radiopaque marker including at least one 2D foldable segment, each 2D foldable segment configured to be foldable away from the surface of the subject such that if folded the 2D foldable segment appears in radiographic images of the skeletal portion that are acquired from a second image view that is different from the first image view, the at least one 2D foldable segment thereby facilitating associating a given skeletal portion that appears in the radiographic images of the skeletal portion from the first image view, with the given skeletal portion in the radiographic images of the skeletal portion from the second image view, by facilitating identification of the at least one 2D foldable segment in the radiographic images of the skeletal portion acquired from the second image view.

For some applications, the skeletal portion is a spine of a subject.

For some applications, the second image view is different from the first image view by at least 20 degrees.

For some applications, the first image view is an anteroposterior (AP) image view of the skeletal portion.

For some applications, the second image view is a lateral image view of the skeletal portion.

For some applications, a fold line of the 2D foldable segment is pre-designated.

For some applications, the apparatus further includes an adhesive disposed on the radiopaque marker.

For some applications, no adhesive is disposed on any of the at least one 2D foldable segments.

For some applications:
further comprising a support comprising a set of discretely identifiable support-affixed radiopaque markers, such that the set of discretely identifiable support-affixed radiopaque markers appear in radiographic images of the skeletal portion that are acquired from the first image view, and the at least one 2D foldable segment comprises at least one 2D foldable tab coupled to the support, wherein each 2D foldable tab comprises at least one tab-affixed radiopaque marker such that if the 2D foldable tab is folded away from the surface of the subject, the at least one tab-affixed radiopaque marker appears in radiographic images of the skeletal portion that are acquired from the second image view.

For some applications, the at least one 2D foldable segment is configured to be converted to a 3D element when folded away from the surface of the subject, such that, if folded, the 3D element appears in radiographic images acquired from at least the first and second image views.

There is further provided, in accordance with some applications of the present invention, a method for performing a procedure on a skeletal portion within a body of a subject, the method including:

attaching a radiopaque marker to a surface of the subject in a vicinity of the skeletal portion, the radiopaque marker comprising at least one 2D foldable segment;

acquiring a radiographic image, from a first image view, of (i) the skeletal portion and (ii) the radiopaque marker; and acquiring a radiographic image of (i) the skeletal portion and (ii) the at least one 2D foldable segment from a second image view that is different from the first image view when the 2D foldable segment is folded away from the surface of the subject.

For some applications, attaching includes attaching the radiopaque marker to a surface of the subject in the vicinity of a spine of the subject.

For some applications, acquiring the radiographic image of (i) the skeletal portion and (ii) the at least one 2D foldable segment from the second image view includes acquiring the radiographic image of (i) the skeletal portion and (ii) the at least one 2D foldable segment from a second image view that is different from the first image view by at least 20 degrees.

For some applications, attaching includes attaching a radiopaque marker including a support, (a) the support including a series of discretely identifiable support-affixed radiopaque markers, and acquiring the radiographic image, from the first image view, of (i) the skeletal portion and (ii) the radiopaque marker including acquiring a radiographic image, from the first image view, of (i) the skeletal portion and (ii) the series of discretely identifiable support-affixed radiopaque markers, and (b) the at least one 2D foldable segment including at least one 2D foldable tab coupled to the support, each 2D foldable tab including at least one tab-affixed radiopaque marker, and acquiring the radiographic image of (i) the skeletal portion and (ii) the at least one 2D foldable segment from a second image view including acquiring a radiographic image of (i) the skeletal portion and (ii) the at least one tab-affixed radiopaque marker.

There is further provided, in accordance with some applications of the present invention, a method for performing a procedure with respect to a targeted vertebra of a spine within a body of a subject, the method including:

acquiring 3D image data of at least the targeted vertebra;

using at least one computer processor, indicating the targeted vertebra within the 3D image data;

positioning a radiopaque element on the body of the subject with respect to the spine of the subject, the radiopaque element being visible to the naked eye;

acquiring a 2D radiographic image of the spine of the subject, such that the radiopaque element appears in the radiographic image; and using the computer processor, registering the targeted vertebra in the 3D image data to the targeted vertebra in the 2D radiographic image, the registering including:

generating a plurality of 2D projections of the targeted vertebra from the 3D image data, for each vertebra that is visible in the 2D radiographic image, identifying if there exists a 2D projection of the targeted vertebra that matches the 2D radiographic image of the vertebra that is visible in the 2D radiographic image, and in response to the identifying, indicating on the 2D radiographic image the vertebra for which a match with a 2D projection of the targeted vertebra was identified, such that a location of the targeted vertebra is identified with respect to the radiopaque element.

For some applications, the method further includes, based on the identified location of the targeted vertebra with respect to the radiopaque element, positioning an intraoperative 3D imaging device such that an imaging volume of the 3D imaging device at least partially overlaps the targeted vertebra.

For some applications, positioning the radiopaque element includes positioning at least one radiopaque marker on the body of the subject with respect to the spine of the subject, the at least one radiopaque marker being visible to the naked eye.

For some applications, positioning the radiopaque element includes positioning a radiopaque surgical tool on the body of the subject with respect to the spine of the subject.

There is further provided, in accordance with some applications of the present invention, a method for registering a 2D radiographic image of a targeted skeletal portion within a body of a subject to 3D image data of the targeted skeletal portion, the method including:
  acquiring 3D image data of the targeted skeletal portion;
  obtaining deep-learning data by inputting into a deep-learning engine (a) a database of 2D projection images generated from the 3D image data, and (b) respective values of viewing parameters corresponding to each 2D projection image, such that given a certain 2D projection image, the deep-learning engine learns to suggest simulated respective values of viewing parameters that correspond to that 2D projection image;
  inputting the obtained deep-learning data into at least one computer processor;
  acquiring an intraoperative 2D radiographic image of the targeted skeletal portion; and
  registering the intraoperative 2D radiographic image of the targeted skeletal portion to the 3D image data of the targeted skeletal portion, the registering including:
    using the computer processor:
      using the obtained deep-learning data to limit a search space in which a 2D projection from the 3D image data that matches the 2D radiographic image of the targeted skeletal portion should be searched for, and
      searching for a 2D projection that matches the 2D radiographic image of the targeted skeletal portion only within the limited search space.

For some applications, acquiring the 3D image data includes acquiring 3D image data of a targeted vertebra of a spine of the subject.

For some applications, obtaining the deep learning data includes obtaining deep learning data by inputting into the deep-learning engine (a) a database of 2D projection images generated from the 3D image data, and (b) respective viewing distances and viewing angles corresponding to each 2D projection image, such that given a certain 2D projection image, the deep learning engine learns to suggest a simulated respective viewing distance and viewing angle that correspond to that 2D projection image.

There is further provided, in accordance with some applications of the present invention, a method for use with at least two tools configured to be advanced into a skeletal portion within a body of a subject along respective longitudinal insertion paths, the method including:
  acquiring 3D image data of the skeletal portion;
  planning the respective longitudinal insertion paths;
  associating the planned respective longitudinal insertion paths with the 3D image data;
  while respective portions of the tools are disposed at first respective locations along their respective longitudinal insertion paths with respect to the skeletal portion, sequentially:
    acquiring a first 2D x-ray image of at least the respective portions of the tools and the skeletal portion from a first view, using a 2D x-ray imaging device that is disposed at a first pose with respect to the subject's body;
    moving the 2D x-ray imaging device to a second pose with respect to the subject's body; and
    while the 2D x-ray imaging device is at the second pose, acquiring a second 2D x-ray image of at least the respective portions of the tools and the skeletal portion from a second view; and
  using at least one computer processor, automatically matching between a tool in the first 2D x-ray image and the same tool in the second 2D x-ray image, the matching including:
    (A) identifying respective tool elements of each of the tools within each of the first and second 2D x-ray images, by means of image processing;
    (B) registering the first and second x-ray images to the 3D image data, the registering including:
      generating a plurality of 2D projections from the 3D image data, and
      identifying respective first and second ones of the 2D projections that match the first and second 2D x-ray images of the skeletal portion; and
    (C) based upon the identified respective tool elements within the first and second 2D x-ray images, and the registration of the first and second 2D x-ray images to the 3D image data, identifying for at least one tool element within the first and second 2D x-ray images a correspondence between (i) the tool element and (ii) the respective planned longitudinal insertion path for that tool.

For some applications, associating the planned respective longitudinal insertion paths with the 3D image data includes displaying each planned longitudinal insertion path distinctively within the 3D image data.

For some applications, the method further includes, using the at least one computer processor, based on the identified respective tool elements within the first and second 2D x-ray images, and the registration of the first and second 2D x-ray images to the 3D image data, overlaying the planned respective longitudinal insertion paths distinctively on the first and second 2D x-ray images.

For some applications, the method further includes, using the at least one computer processor, based on the identified respective tool elements within the first and second 2D x-ray images, and the registration of the first and second 2D x-ray images to the 3D image data, positioning respective representations of the respective tool elements within a display of the 3D image data.

For some applications, acquiring the first 2D x-ray image of at least the respective portions of the tools and the skeletal portion from the first view includes using a 2D x-ray imaging device that is unregistered with respect to the body of the subject.

There is further provided, in accordance with some applications of the present invention, a method for performing a procedure with respect to a given vertebra of a spine within a body of a subject, the method including:
  placing a set of radiopaque markers in a vicinity of the subject, the markers being visible to the naked eye;
  using a radiographic imaging device, acquiring a plurality of radiographic images of the set of radiopaque markers, respective images being of respective locations along at least a portion of the subject's spine and each of the images including at least some of the radiopaque markers;
  using at least one computer processor:

identifying locations of the radiopaque markers within the radiographic images, by means of image processing;

combining at least some of the radiographic images based upon the identified locations of the radiopaque markers within the radiographic images;

determining a location of the given vertebra within the combined radiographic images; and generating an output in response thereto; and based on the identified location of the given vertebra with respect to the radiopaque markers within the combined radiographic images, manually identifying a location of the given vertebra on the subject's body with respect to the markers positioned in the vicinity of the subject; and positioning an intraoperative 3D imaging device such that an imaging volume of the 3D imaging device at least partially overlaps the given vertebra to be subsequently operated on.

For some applications, placing the set of radiopaque markers in the vicinity of the subject includes placing the set of radiopaque markers in the vicinity of the subject such that the set of radiopaque markers is in contact with the subject.

For some applications, placing the set of radiopaque markers in the vicinity of the subject includes placing the set of radiopaque markers in the vicinity of the subject such that the set of radiopaque markers is not in contact with the subject.

For some applications, determining the location of the given vertebra within the combined radiographic images includes, using the at least one computer processor, determining the location of the given vertebra within the combined radiographic images by means of image processing.

There is further provided, in accordance with some applications of the present invention, a method for performing a procedure using a tool configured to be advanced into a skeletal portion within a body of a subject along a longitudinal insertion path, the method including:

acquiring 3D image data of the skeletal portion;

while a portion of the tool is disposed at a first location along the longitudinal insertion path with respect to the skeletal portion, sequentially:
1. acquiring a first 2D x-ray image of at least the portion of the tool and the skeletal portion from a first view, using a 2D x-ray imaging device that is disposed at a first pose with respect to the subject's body;
2. moving the 2D x-ray imaging device to a second pose with respect to the subject's body; and
3. while the 2D x-ray imaging device is at the second pose, acquiring a second 2D x-ray image of at least the portion of the tool and the skeletal portion from a second view;

using at least one computer processor:
registering the first and second 2D radiographic images to the 3D image data, the registering including:
generating a plurality of 2D projections from the 3D image data, and
identifying respective first and second 2D projections that match the first and second 2D radiographic images of the skeletal portion;
identifying a location of the portion of the tool with respect to the skeletal portion, within the first and second 2D radiographic images, by means of image processing; and
based upon (a) the identified location of the portion of the tool within the first and second 2D x-ray images, and (b) the registration of the first and second 2D x-ray images to the 3D image data, identifying the first location of the portion of the tool with respect to the 3D image data;

computing an anticipated longitudinal forward path of the tool within the 3D image data from the first and second 2D radiographic images;

subsequently, moving the portion of the tool to a second location along the longitudinal insertion path with respect to the skeletal portion;

subsequent to moving the portion of the tool to the second location, acquiring one or more additional 2D radiographic images of at least the portion of the tool and the skeletal portion from a single image view; and using the computer processor, facilitating identifying whether or not the tool has deviated from the anticipated longitudinal forward path by:
registering the additional one or more 2D radiographic images to the 3D image data, such that the anticipated longitudinal forward path of the tool is registered with the additional one or more 2D radiographic images, and
identifying a location of the portion of the tool with respect to the skeletal portion, within the additional one or more 2D radiographic images, by means of image processing.

For some applications, acquiring the first 2D x-ray image of at least the portion of the tool and the skeletal portion from the first view includes using a 2D x-ray imaging device that is unregistered with respect to the body of the subject.

For some applications, the method further includes, using the computer processor, subsequently to registering the additional one or more 2D radiographic images to the 3D image data, overlaying the anticipated longitudinal forward path of the tool on the additional one or more 2D radiographic images.

There is further provided, in accordance with some applications of the present invention, a method for registering a 2D radiographic image of a targeted skeletal portion within a body of a subject to 3D image data of the targeted skeletal portion, the method including:

during a pre-processing phase:
acquiring 3D image data of the skeletal portion; and
using at least one computer processor:
generating N 2D projection images from the 3D image data,
determining a set of attributes that describe each of the 2D projection images, the number of the attributes being smaller than a number of pixels in each 2D projection image,
determining, for each 2D projection image, a respective value for each of the attributes, and
storing N respective sets of attributes, with respective values assigned for each attribute, for the N 2D projection images;

following the pre-processing phase, during a medical procedure:
acquiring a 2D radiographic image of the skeletal portion; and
using at least one computer processor:
determining at least one specific set of values for the attributes that describe at least a portion of the 2D radiographic image,
searching among the stored N respective sets of attributes for a set that best matches any of the at least one specific set of values, and
using the set that best matches, generating an additional 2D projection image from the 3D image data, the additional 2D projection image matching at least the portion of the 2D radiographic image.

For some applications, the method further includes discarding the N 2D projection images subsequently to storing the N respective sets of attributes.

There is further provided, in accordance with some applications of the present invention, a method for registering a 2D radiographic image of a targeted skeletal portion within a body of a subject to 3D image data of the targeted skeletal portion, the method including:

during a pre-processing phase:
acquiring 3D image data of the skeletal portion;
and using at least one computer processor:
generating N 2D projection images from the 3D image data,
determining a set of attributes that describe each of the 2D projection images, the number of the attributes being smaller than a number of pixels in each 2D projection image,
determining, for each 2D projection image, a respective value for each of the attributes, and
storing N respective sets of attributes, with respective values assigned for each attribute, for the N 2D projection images;
following the pre-processing phase, during a medical procedure:
acquiring a 2D radiographic image of the skeletal portion; and
using at least one computer processor:
determining at least one specific set of values for the attributes that describe at least a portion of the 2D radiographic image,
searching among the stored N respective sets of attributes for a set that best matches any of the at least one specific set of values, and
using the set that best matches, generating a plurality of additional 2D projection images from the 3D image data, each of the plurality of additional projection images approximating at least the portion of the 2D radiographic image, and
using the plurality of additional projection images, optimizing to find a 2D projection image that matches at least the portion of the 2D radiographic image.

For some applications, the method further includes discarding the N 2D projection images subsequently to storing the N respective sets of attributes.

There is further provided, in accordance with some applications of the present invention, a method for performing a procedure with respect to a skeletal portion with the body of a subject, the method including:

acquiring 3D image data of the skeletal portion;
acquiring a plurality of 2D radiographic images, each image showing a distinct segment of the skeletal portion;
using at least one computer processor:
registering the 2D radiographic images with the 3D image data, such that a post-registration correspondence is created between each 2D radiographic image and the 3D image data;
using the post-registration correspondence between each of the 2D radiographic images and the 3D image data, relating the 2D images with respect to each other; and
using the relationship of the 2D radiographic images with respect to each other, generating a combined 2D radiographic image comprising multiple segments of the skeletal portion.

For some applications, acquiring the plurality of 2D radiographic images includes acquiring the plurality of 2D radiographic images from a similar viewing direction.

For some applications, acquiring the plurality of 2D radiographic images includes acquiring at least two of the 2D radiographic images from viewing directions that are not similar to one another.

For some applications, acquiring the plurality of 2D radiographic images includes acquiring the plurality of 2D radiographic images such that there is overlap between at least two of the segments shown in two respective 2D radiographic images.

For some applications, acquiring the plurality of 2D radiographic images includes acquiring the plurality of 2D radiographic images such that at least two of the segments shown in two respective 2D radiographic images do not overlap with each other.

For some applications, acquiring 3D image data of the skeletal portion includes acquiring 3D image data of a spine of the subject.

For some applications, generating a combined 2D radiographic image includes multiple segments of the skeletal portion comprises generating a combined 2D radiographic image comprising multiple segments of the spine, and the method further comprising, using the combined radiographic image of the spine, identifying a given vertebra of the spine of the subject.

The present invention will be more fully understood from the following detailed description of embodiments thereof, taken together with the drawings, in which:

BRIEF DESCRIPTION OF THE DRAWINGS

FIGS. 5A, 5B, 5C, and 5D are schematic illustrations of radiopaque markers which are placed upon a subject and include at least one 2D foldable segment, in accordance with some applications of the present invention;

DETAILED DESCRIPTION OF EMBODIMENTS

Figure 1A:
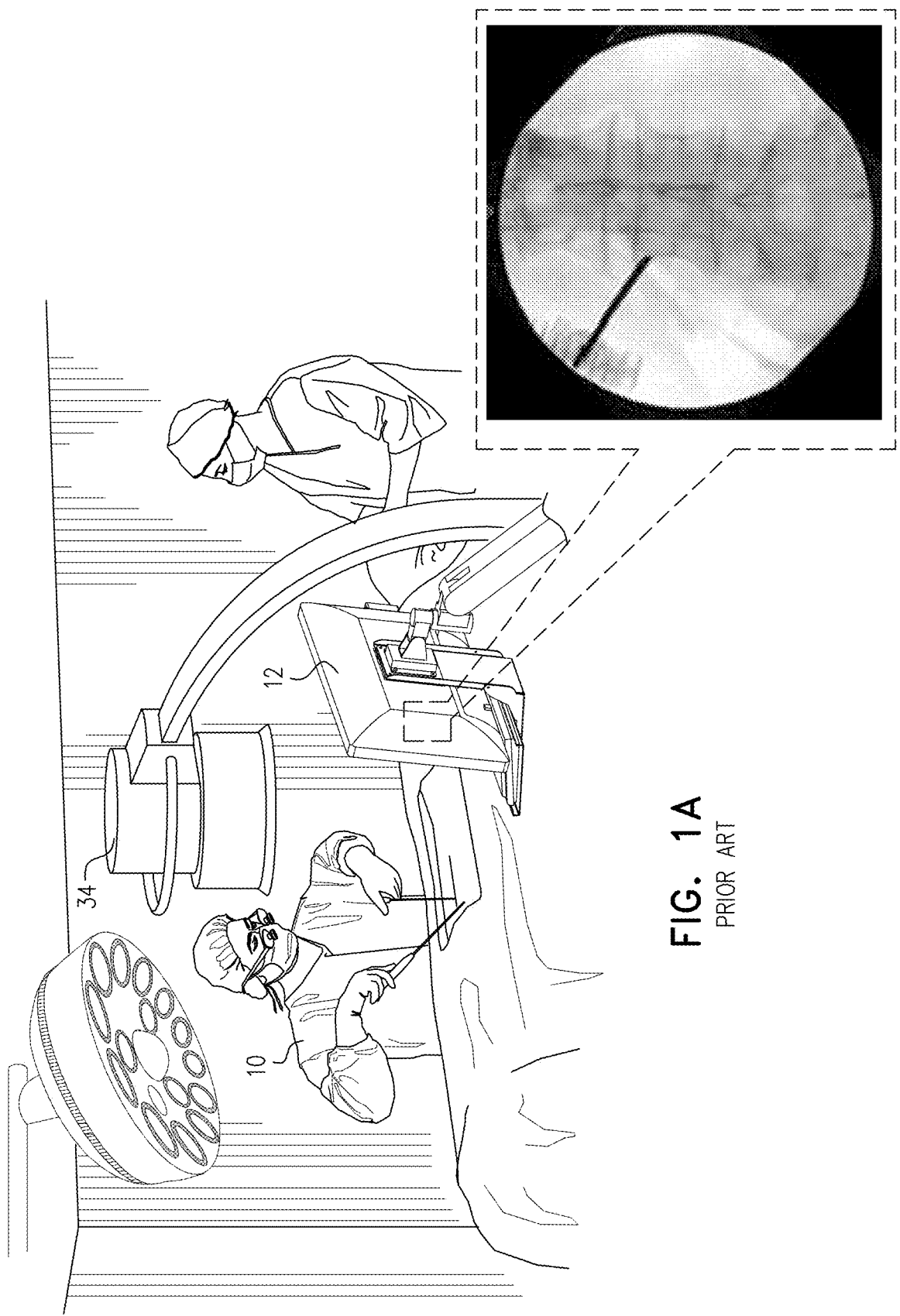
FIG. 1A is a schematic illustration of an orthopedic operating room, as used in prior art techniques.
Figure 1B:
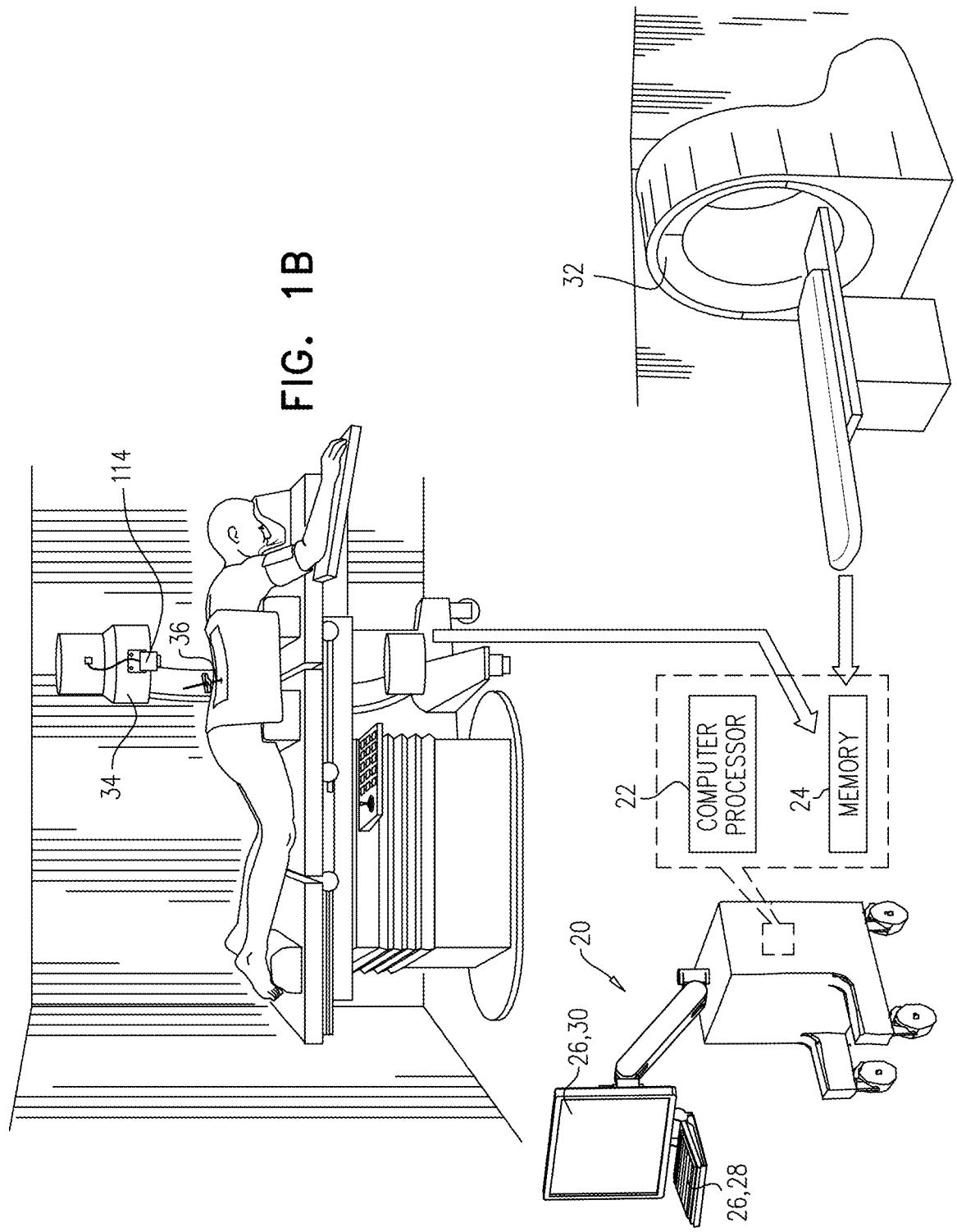
FIG. 1B is a schematic illustration of a system for use with procedures that are performed on skeletal anatomy, in accordance with some applications of the present invention.

Reference is now made to FIG. 1B, which is a schematic illustration of a system 20 for use with procedures that are performed on skeletal anatomy, in accordance with some applications of the present invention. For some applications, the system is used for a procedure that is performed on one or more vertebrae, or other portions of the spine. However, the scope of the present invention includes applying any of the apparatus and methods described herein to procedures performed on other portions of a subject's skeletal anatomy, mutatis mutandis. Such procedures may include joint (e.g., shoulder, elbow, wrist, knee, hip, and/or ankle) replacement, joint repair, fracture repair (e.g., femur, tibia, and/or fibula), a procedure that is performed on a rib (e.g., rib removal, or rib resection), and/or other interventions in which 3D image data are acquired prior to the intervention and 2D images are acquired during the intervention.

System 20 typically includes a computer processor 22, which interacts with a memory 24, and one or more user interface device 26. Typically, the user interface devices include one or more input devices, such as a keyboard 28 (as shown), and one or more output devices, e.g., a display 30, as shown. Inputs to, and outputs from, the computer processor that are described herein are typically performed via the user interface devices. For some applications, the computer processor as well as the memory and the user interface devices, are incorporated into a single unit, e.g., a tablet device, an all-in-one computer, and/or a laptop computer.

For some applications, the user interface devices include a mouse, a joystick, a touchscreen device (such as a smartphone or a tablet computer) optionally coupled with a stylus, a touchpad, a trackball, a voice-command interface, a hand-motion interface, and/or other types of user interfaces that are known in the art. For some applications, the output device includes a head-up display and/or a head-mounted display, such as Google Glass® or a Microsoft HoloLens®. For some applications, the computer processor generates an output on a different type of visual, text, graphics, tactile, audio, and/or video output device, e.g., speakers, headphones, a smartphone, or a tablet computer. For some applications, a user interface device acts as both an input device and an output device. For some applications, computer processor 22 generates an output on a computer-readable medium (e.g., a non-transitory computer-readable medium), such as a disk or a portable USB drive. For some applications, the computer processor comprises a portion of a picture archiving and communication system (PACS), and is configured to receive inputs from other components of the system, e.g., via memory 24. Alternatively or additionally, the computer processor is configured to receive an input on a computer-readable medium (e.g., a non-transitory computer-readable medium), such as a disk or a portable USB drive. It is noted that, for some applications, more than one computer processor is used to perform the functions described herein as being performed by computer processor 22.

Typically, 3D image data are acquired before the subject is in the operating room for the procedure, or when the subject is in the operating room, but before an intervention has commenced. For example, 3D CT image data of the portion of the skeletal anatomy upon which the procedure is to be performed (and/or neighboring portions of the anatomy) may be acquired using a CT scanner 32. Alternatively or additionally, 3D MRI image data of the portion of the skeletal anatomy upon which the procedure is to be performed (and/or neighboring portions of the anatomy) may be acquired using an MRI scanner. For some applications, 3D x-ray data are acquired. Typically, the 3D image data are transferred to memory 24, and are retrieved from the memory by computer processor 22. It is noted that for illustrative purposes, FIG. 1B shows the CT scanner, the C-arm, and system 20 together with one another. However, in accordance with the above description, for some applications, the CT scanner is not disposed in the same room as system 20, and/or C-arm 34.

During the procedure, real time 2D images are acquired by a radiographic imaging device, e.g., a C-arm 34 (as shown), which acquires 2D x-ray images. For some applications, such 2D images are acquired by an imaging device (such as an o-arm or a 3D x-ray c-arm) situated in the operating room and also capable of generating 3D images. For example, such imaging device may be used for generating 3D image data at the beginning of the intervention in order to image the baseline anatomy in 3D, and then again at the latter part of the intervention in order to evaluate its outcomes (such as how well implants were positioned), and in between be used similarly to a regular c-arm in order to generate 2D during the intervention. For some applications, such device fulfils both the roles of the 3D CT and the 2D c-arm, as such roles are described throughout this document with respect to embodiments of the present invention.

For some applications, the 2D images are captured in real time by a frame grabber of system 20 that is connected to an output port of the C-arm. Alternatively or additionally, system 20 and the C-arm are connected to one another via a PACS network (or other networking arrangement, wired or wireless) to which system 20 and C-arm 34 are connected, and the 2D images are transferred, once acquired, to system 20 via the PACS network (e.g., via memory 24). Alternatively or additionally, the C-arm sends image files, for example in DICOM format, directly to system 20 (e.g., via memory 24).

Typically, the interventional part of a procedure that is performed on skeletal anatomy, such as the spine, commences with the insertion of a tool, such as a Jamshidi™ needle 36 which is typical for minimally-invasive (or less-invasive) surgery. A Jamshidi™ needle typically includes an inner tube and an outer tube. The Jamshidi™ needle is typically inserted to or towards a target location, at which point other tools and/or implants are inserted using the Jamshidi™ needle. Typically, in open surgery, for lower-diameter tools and/or implants, the inner tube of the Jamshidi™ needle is removed, and the tool and/or implant is inserted via the outer tube of the Jamshidi™ needle, while for larger-diameter tools and/or implants, the tool and/or implant is inserted by removing the inner tube of the Jamshidi™ needle, inserting a stiff wire through the outer tube, removing the outer tube, and then inserting the tool and/or implant along the stiff wire. For minimally-invasive surgery, the aforementioned steps (or similar steps thereto) are typically performed via small incisions. Alternatively, for more-invasive or open surgery, the tool inserted may be, for example, a pedicle finder and/or a pedicle marker.

It is noted that, in general throughout the specification and the claims of the present application, the term "tool" should be interpreted as including any tool or implant that is inserted into any portion of the skeletal anatomy during a procedure that is performed upon the skeletal anatomy. Such tools may include flexible, rigid and/or semi-rigid probes, and may include diagnostic probes, therapeutic probes, and/or imaging probes. For example, the tools may include Jamshidi™ needles, other needles, k-wires, pedicle finders, pedicle markers, screws, nails, other implants, implant delivery probes, drills, endoscopes, probes inserted through an endoscope, tissue ablation probes, laser probes, balloon probes, injection needles, tissue removal probes, drug delivery probes, stimulation probes, dilators, etc. Typically, such procedures include spinal stabilization procedures, such as vertebroplasty (i.e., injection of synthetic or biological cement in order to stabilize spinal fractures), kyphoplasty (i.e., injection of synthetic or biological cement in order to stabilize spinal fractures, with an additional step of inflating a balloon within the area of the fracture prior to injecting the cement), fixation (e.g., anchoring two or more vertebrae to each other by inserting devices such as screws into each of the vertebrae and connecting the screws with rods), fixation and fusion (i.e., fixation with the additional step of an implant such as a cage placed in between the bodies of the vertebrae), biopsy of suspected tumors, tissue ablation (for example, RF or cryo), injection of drugs, and/or endoscopy (i.e., inserting an endoscope toward a vertebra and/or a disc, for example, in order to remove tissue (e.g., disc tissue, or vertebral bone) that compresses nerves).

Figure 2:
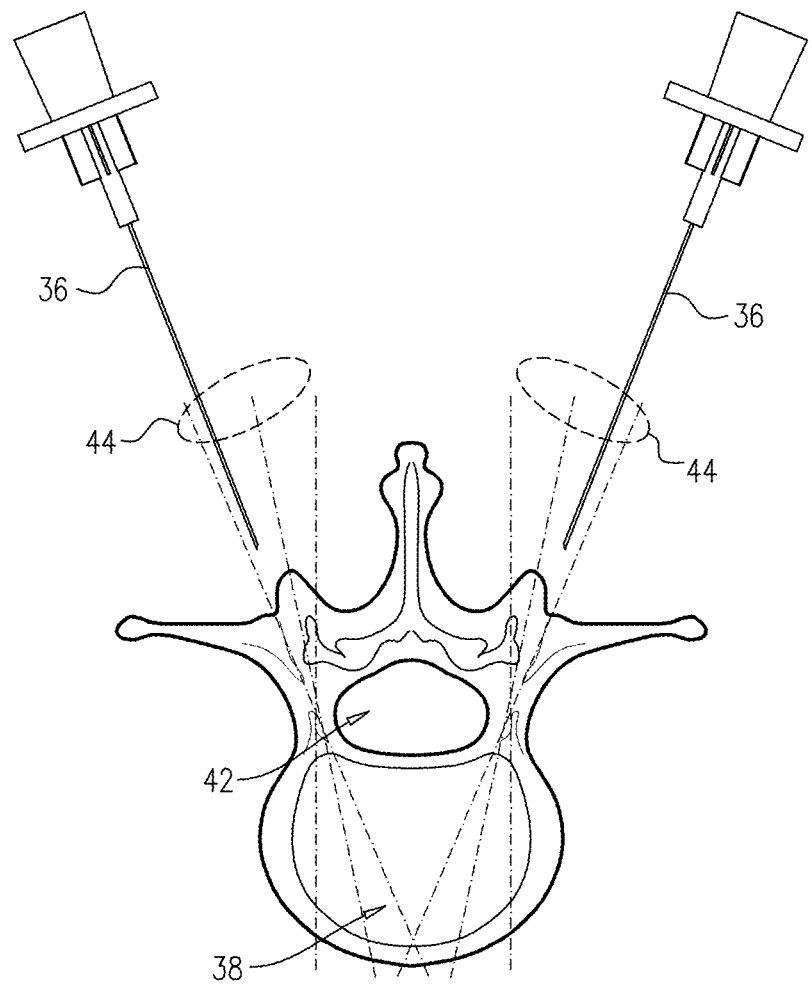
FIG. 2 is a schematic illustration of two tools (e.g., Jamshidi™ needles) being inserted into a vertebra and the desired insertion windows for the insertion of such tools, as used in prior art techniques.

Reference is now made to FIG. 2, which is a schematic illustration of two Jamshidi™ needles 36 being inserted into a vertebra 38, as used in prior art techniques. Typically, a spinal intervention aimed at a vertebral body is performed with tools being aimed at 10-11 o'clock and 1-2 o'clock insertion windows with respect to the subject's spine. Tool insertion into a vertebra should avoid the spinal cord 42, and additionally needs to avoid exiting the vertebra from the sides, leaving only two narrow insertion windows 44, on either side of the vertebra. As described hereinbelow with reference to FIGS. 3A-4B, typically the most important images for determining the locations of the insertion windows are those derived from 3D image data, and are not available from the real time 2D images that are typically acquired during the intervention.

Figure 3A:
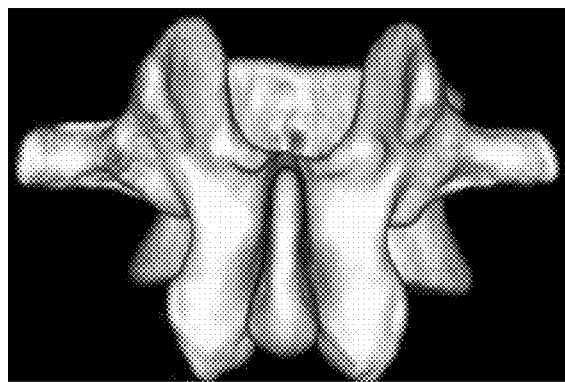
FIGS. 3A and 3B show a 3D CT image of a vertebra (FIG. 3A), as well as a 2D axial slice that is derived from the 3D CT image (FIG. 3B), as used in prior art techniques.
Figure 3B:
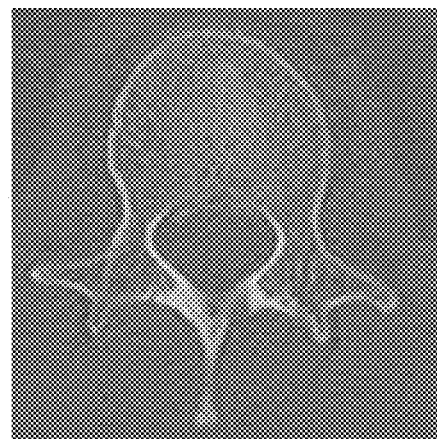
Figure 4A:
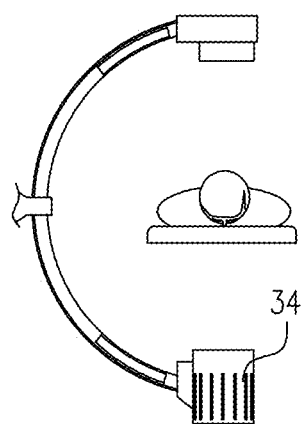
FIGS. 4A and 4B are schematic illustrations showing a C-arm being used to acquire an anteroposterior ("AP") 2D radiographic image and a resultant AP image (FIG. 4A), and the C-arm being used to acquire a lateral 2D radiographic image and a resultant lateral image (FIG. 4B), as used in prior art techniques.
Figure 4A:
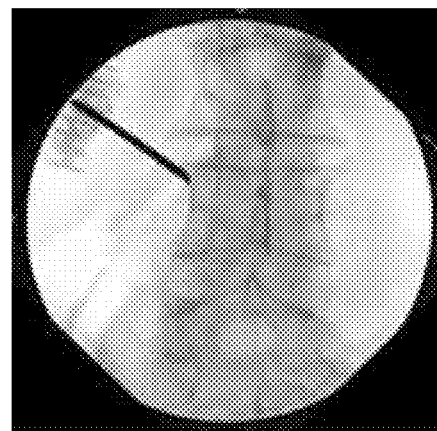
Figure 4B:
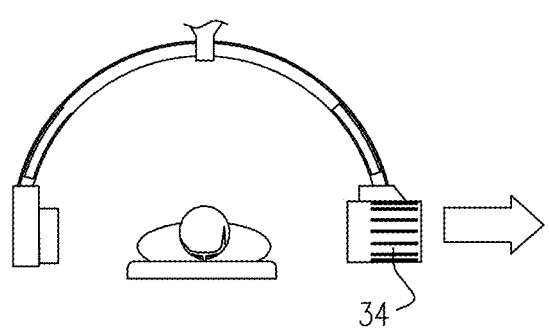
Figure 4B:
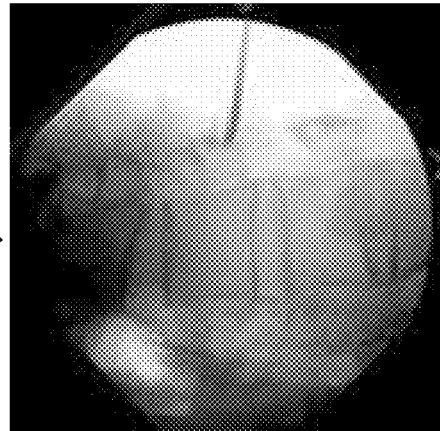

Reference is now made to FIGS. 3A and 3B, which are schematic illustrations of a 3D CT image of a vertebra (FIG. 3A), as well as a 2D axial slice that is derived from the 3D CT image (FIG. 3B), such images being used in prior art techniques. Reference is also made to FIGS. 4A and 4B, which show C-arm 34 being used to acquire an anterior-posterior ("AP") 2D radiographic image and a resultant AP image (FIG. 4A), and C-arm 34 being used to acquire a lateral 2D radiographic image and a resultant lateral image (FIG. 4B), as used in prior art techniques.

As may be observed, the view of the vertebra that is important for determining the entry point, insertion direction, and insertion depth of the tool is shown in the axial 2D image slice of FIG. 3B. By contrast, the 2D radiographic images that are acquired by the C-arm are summations of 3D space, and do not show cross-sectional views of the vertebra. Furthermore, due to the anatomy of the human body, such summations would not have been valuable if and when acquired from an axial angle (from the head, or from the toes) because it would not be possible to discern specifically the spinal portion being operated upon. As described hereinabove, Computer Aided Surgery (CAS) systems typically make use of CT and/or MRI images, generated before the subject has been placed in the operating room, or once the subject has been placed in the operating room but typically before an intervention has commenced. However, such procedures are typically more expensive than non-CAS procedures (such non-CAS procedures, including open procedures, mini-open procedures, and minimally-invasive procedures), limit tool selection to those fitted with location sensors as described above, and typically require such tools to be individually identified and calibrated at the beginning of each surgery.

In accordance with some applications of the present invention, the intra-procedural location of a tool is determined with respect to 3D image data (e.g., a 3D image, a 2D cross-section derived from 3D image data, and/or a 2D projection image derived from 3D image data), in a non-CAS procedure (e.g., in an open, mini-open and/or minimally-invasive procedure). The techniques described herein are typically practiced without requiring the fitting of location sensors (such as infrared transmitters or reflectors, or magnetic or electromagnetic sensors) to the tool or to the subject, and without requiring identification and/or calibration of tools prior to the procedure. The techniques described herein are typically practiced without requiring the fitting of any radiopaque marker to the tool, rather they rely on the existing radio-opacity of the tool for its identification in the x-ray images. The techniques described herein are typically practiced without requiring knowledge of the precise geometry and/or the dimensions of the tool for its identification in the x-ray images. The techniques described herein typically do not require tracking the location of the subject's body or the applicable portion of the subject's body, and do not assume any knowledge of the location coordinates of the subject's body in some reference frame. The techniques described herein typically do not require location sensors that rely upon tracking technologies (e.g., electromagnetic or IR tracking technologies) that are not typically used in an orthopedic operating room when not using CAS systems. Further typically, the techniques described herein are practiced without requiring knowledge of any precise parameters of any individual pose of the 2D radiographic imaging device (e.g., C-arm 34), and typically without requiring poses of the 2D radiographic imaging device (e.g., C-arm 34) to be tracked relative to each other, and/or relative to the position of the subject. For some applications, 2D radiographic images (e.g., 2D x-ray images) are acquired from two or more views, by moving a radiographic imaging device to respective poses between acquisitions of the images of respective views. Typically, a single x-ray source is used for acquisition of the 2D x-ray images, although, for some applications, multiple sources are used. In general, where views of the 2D radiographic imaging device are described herein as being AP, lateral, oblique, etc., this should not be interpreted as meaning that images must be acquired from precisely such views, rather acquiring images from generally such views is typically sufficient. Typically, the techniques described herein are tool-neutral, i.e., the techniques may be practiced with any applicable tool and typically without any modification and/or addition to the tool.

It is noted that although some applications of the present invention are described with reference to 3D CT imaging, the scope of the present invention includes using any 3D imaging, e.g., MRI, 3D x-ray imaging, 3D ultrasound imaging, and/or other modalities of 3D imaging, mutatis mutandis. Such imaging may be performed prior to, at the commencement of, and/or at some point during, an intervention. For example, the 3D imaging may be performed before the subject has been placed within the operating room, when the subject is first placed within the operating room, or at some point when the subject is in the operating room, but prior to the insertion of a given tool into a given target portion, etc. Similarly, although some applications of the present invention are described with reference to 2D radiographic or x-ray imaging, the scope of the present invention includes using any 2D imaging, e.g., ultrasound and/or other modalities of 2D imaging, mutatis mutandis. Although some applications of the present invention are described with reference to procedures that are performed on skeletal anatomy and/or vertebrae of the spine, the scope of the present invention includes applying the apparatus and methods described herein to other orthopedic interventions (e.g., a joint (e.g., shoulder, knee, hip, and/or ankle) replacement, joint repair, fracture repair (e.g., femur, tibia, and/or fibula), a procedure that is performed on a rib (e.g., rib removal, or rib resection), vascular interventions, cardiovascular interventions, neurovascular interventions, abdominal interventions, diagnostic interventions, therapeutic irradiations, and/or interventions performed on other portions of a subject, including interventions in which 3D image data are acquired prior to the intervention and 2D images are acquired during the intervention, mutatis mutandis.

Reference is now made to FIGS. 5A-D, which are schematic illustration of sets 50 of radiopaque markers 52 which are typically placed in the vicinity of a skeletal portion, e.g., spine, of a subject, either in contact with or not in contact with the body of the subject, in accordance with some applications of the present invention. For some applications, sets 50 of radiopaque markers 52 includes a support 53 having a series of discretely identifiable support-affixed radiopaque markers 52, such that the series of discretely identifiable support-affixed radiopaque markers 52 appear in radiographic images of the skeletal portion. For some applications, the series of markers 52 is a series of sequential discretely identifiable support-affixed radiopaque markers along a longitudinal axis of support 53. For some applications, the sets of markers are disposed on a drape disposed on the applicable portion of the subject's body, for example, an incision drape attached upon the applicable portion, as shown. The drape is typically sterile and disposable. For some applications, the set of markers includes an authentication and/or an anti-counterfeiting element, such as RFID, bar code(s), etc.

Typically, sets 50 of markers 52 are attached, e.g., by an adhesive disposed on a surface of the marker, e.g., an adhesive disposed on support 53, to a surface of the subject in a vicinity of a site, e.g., skeletal portion, at which an intervention is to be performed, and such that at least some of the markers appear in 2D radiographic images that are acquired of the intervention site from typical imaging views for such an intervention. For example, for a procedure that is performed on the subject's vertebra(e) and particularly within one or more vertebral bodies, the markers are typically placed on the subject's back in a vicinity of the site of the spinal intervention, such that at least some of the markers appear in 2D radiographic images that are acquired of the intervention site from AP imaging views, and potentially from additional imaging views as well. For some applications, the markers are placed on the subject's side in a vicinity of the site of the spinal intervention, such that at least some of the markers appear in 2D radiographic images that are acquired of the intervention site from a lateral imaging view. For some applications, the markers are placed on the subject's back, such that at least some of the markers are level with the subject's sacrum.

For some applications, known dimensions of, or distances between (e.g., markers spaced at 1 cm from other another), radiopaque markers 52 are used in scaling 2D x-ray images comprising portions of the marker set prior to the registration of such 2D images with a 3D data set. Such registration is further described hereinbelow. Typically, and as known in the art, scaling of the images to be registered, when performed prior to the actual registration, facilitates the registration.

For some applications, the set of markers comprises an arrangement wherein portions thereof are visible from different image views. For some applications, such arrangement facilitates for the surgeon the intra-procedural association of elements, including anatomical elements such as a vertebra, seen in a first x-ray image acquired from one view, for example AP, with the same elements as seen in a second x-ray image acquired from a second view, for example lateral. For some applications, such association is performed manually by the surgeon referring to the radiopaque markers and identifying markers that have a known association with one another in the x-ray images, e.g., via matching of alphanumeric characters or distinct shapes. Alternatively or additionally, the association is performed automatically by computer processor 22 of system 20 by means of image processing.

Using known techniques, such association between images, for example of a particular vertebra seen on those images, often requires inserting a tool into or near to, or placing a tool upon, a vertebra of interest such that the tool identifies that vertebra in both images.

According to embodiments of the present invention, association between images acquired from different views (for example AP and lateral, or AP and oblique, or lateral and oblique) is facilitated by any of the following techniques:

For some applications, a marker set 50 comprise 3D radiopaque elements of different identifiable shapes that may be identified from multiple views. In such case, a same 3D element is typically identifiable from multiple viewing angles. Consequently, a same vertebra situated at, near or relative to such 3D elements may be identified in images acquired from different viewing angles.

For some applications, a radiopaque marker set 50 comprises at least one 2D object, e.g., segment (for example, label element, or foldable tabs 54 having at least one tab-affixed radiopaque marker 52') that when unfolded is visible from a first image view (e.g., most views except for lateral, e.g., AP), and when folded away from the body of the subject, e.g., upwards, is visible from both the first image view and a second image view that is different from the first image view by at least 10 degrees, e.g., at least 20 degrees, e.g., at least 30 degrees (e.g., lateral). Typically, the 2D foldable segments, e.g., tabs, have no adhesive disposed on them. For some applications a fold line of tab(s) 54 is parallel to the longitudinal axis of the support. For some applications, the surgeon may fold upwards at any given moment only those one or more foldable 2D segments, e.g., tabs 54 that he or she wishes to be visible from the lateral direction. For example, the surgeon may fold the 2D foldable segments subsequently to acquiring the radiographic image from the first view and prior to acquiring the radiographic image from the second view. Alternatively, the 2D foldable segment may be folded prior to the start of the procedure. Typically, such foldable arrangement also facilitates manufacturing the markers by printing radiopaque ink on support 53, e.g., a flat surface or sheet.

For some applications, such as is shown in FIG. 5B, radiopaque marker set 50 comprises elements that may be converted (for example by folding) from 2D (for example a flat printed marker) to 3D such that in the 3D form an element is identifiable concurrently from multiple angles. For example, the at least one 2D foldable segment, e.g., tab 54 may be converted to a 3D element 54' when folded away from the surface of the subject such that 3D element 54' appears in radiographic images acquired from at least the first and second image views, e.g., from both AP and lateral image views. For some applications, the at least one 2D foldable segment, e.g., tab 54 is shaped to define at least one slit, e.g., at least two slits, that facilitates the 2D foldable segment converting to 3D element 54'.

Figure 5C:
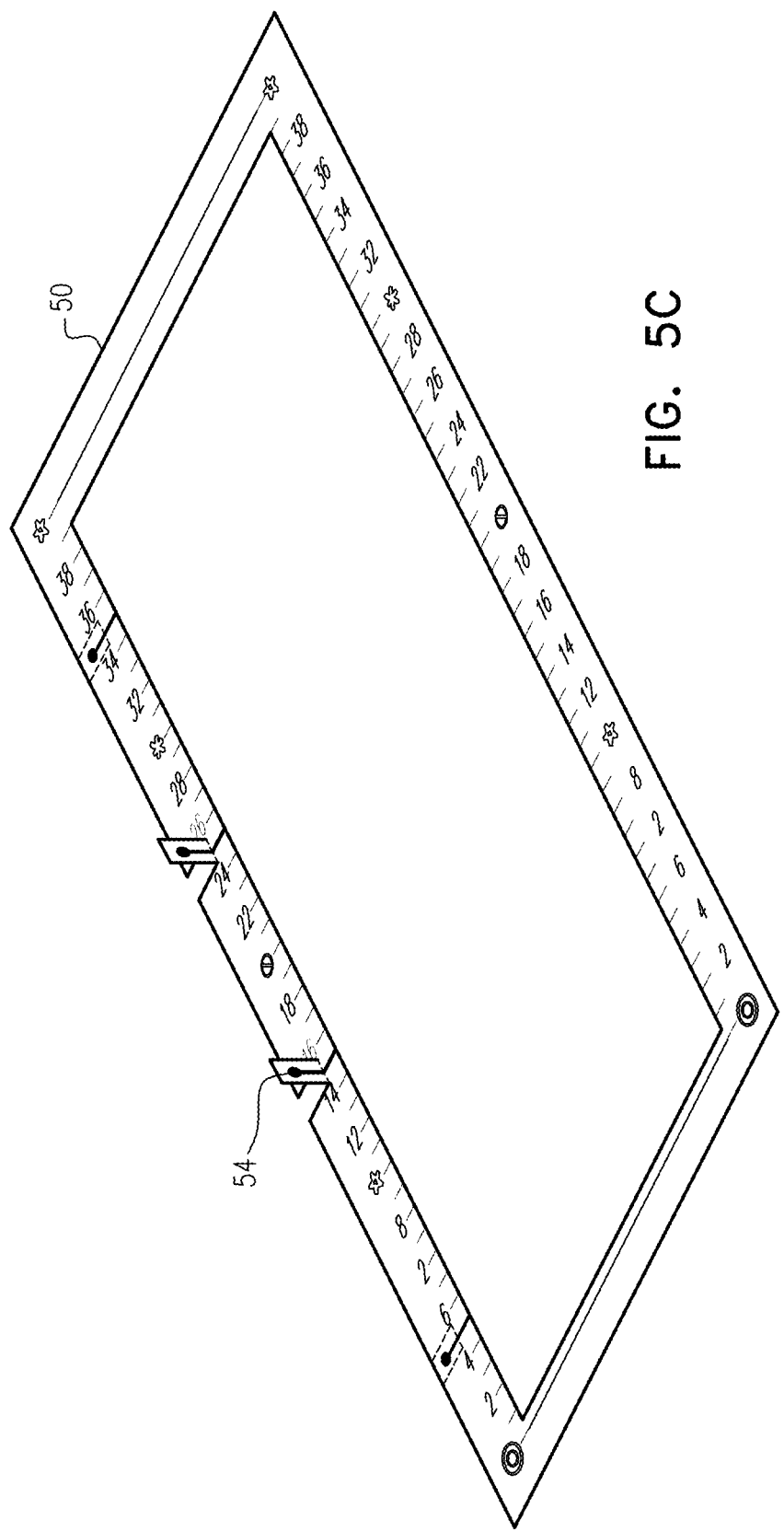

For some applications, radiopaque marker set 50 is in the form of a frame-like label, such as is shown in FIG. 5C, in which certain 2D elements, e.g., segments or tabs 54, when unfolded, are visible from a top view, and when folded are visible from both a top view and a side view, in accordance with some applications of the present invention. Typically, such arrangement also facilitates the manufacturing of the marker which can be done by printing the radiopaque ink on a flat surface.

Figure 5D:
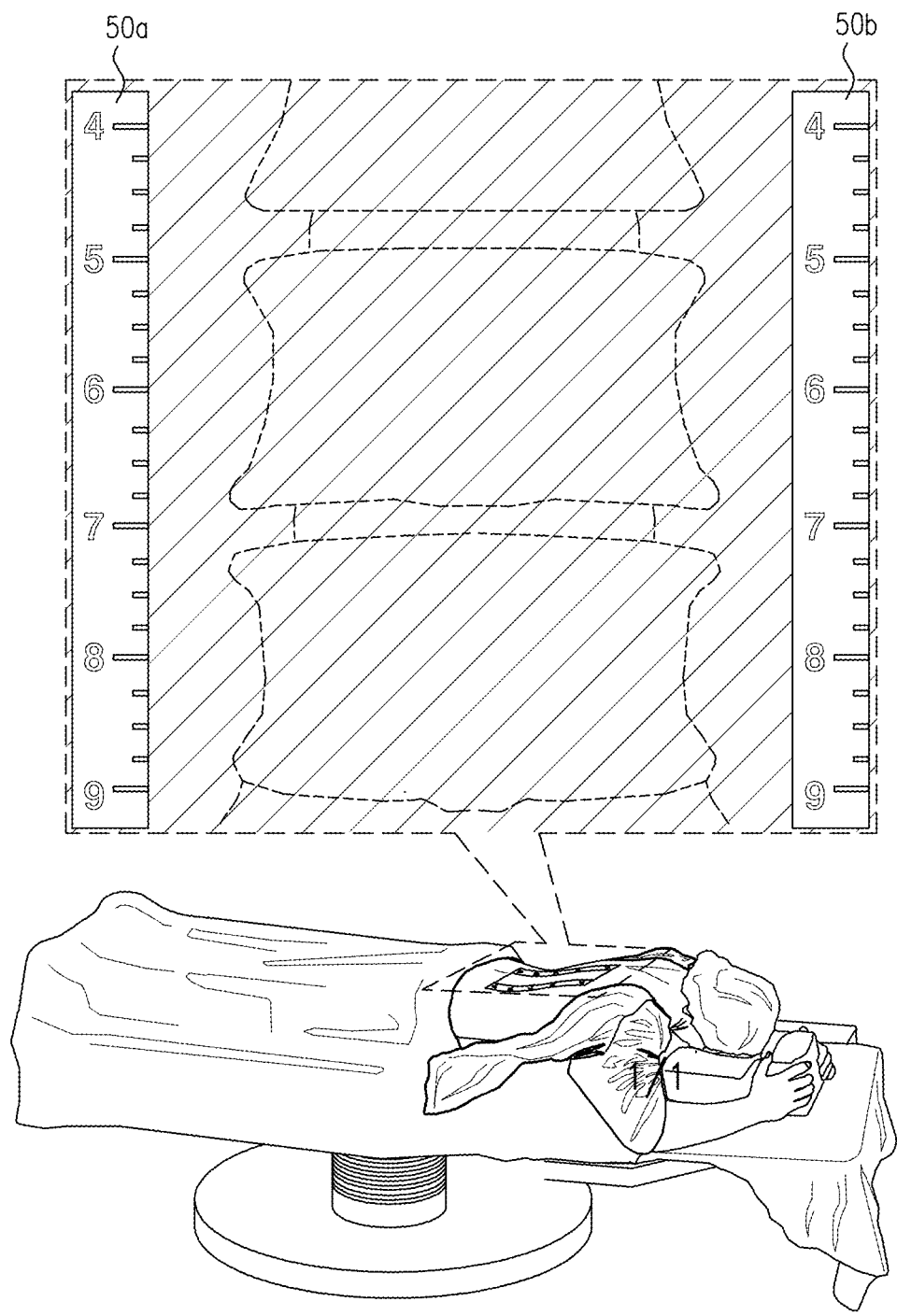
Figure 5E:
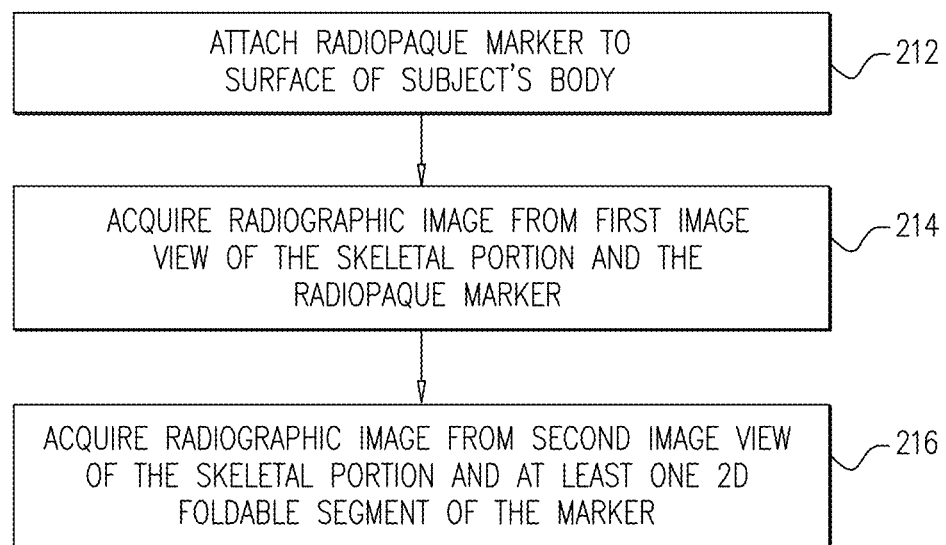
FIG. 5E is a flowchart showing steps that are typically performed using a set of radiopaque markers, in accordance with some applications of the present invention.

Reference is now made to FIG. 5E. Typically, as depicted by the flow chart in FIG. 5E, at least one radiopaque marker 52, e.g., set 50 of markers 52, is attached to a surface of the subject in the vicinity of the skeletal portion, e.g., spine (step 212), a radiographic image is acquired from a first image view of the skeletal portion and the radiopaque marker 52 (step 214), and a radiographic image is acquired from a second image view (step 216) of the skeletal portion and the at least one 2D foldable segment, e.g., tab 54, when the 2D foldable segment is folded away from the surface of the subject. Typically, the second image view is different from the first image view by at least 10 degrees, e.g., at least 20 degrees, e.g., at least 30 degrees. After acquiring the first and second radiographic images, a given skeletal portion, e.g., a given vertebra of a spine, that appears in the radiographic images of the skeletal portion from the first image view may be associated with the given skeletal portion in the radiographic images of the skeletal portion from the second image view, by identifying the at least one folded 2D segment in the radiographic images acquired from the first and second image views.

Typically, surgery on skeletal anatomy commences with attaching a sterile surgical drape, typically an incision drape, at and around the surgical site. In the case of spinal surgery, the surgical approach may be anterior, posterior, lateral, oblique, etc., with the surgical drape placed accordingly. For such applications, sets 50 of markers 52 are typically placed above the surgical drape. Alternatively, sets of markers are placed on the subject's skin (e.g., if no surgical drape is used). For some applications, sets of markers are placed under the subject's body, on (e.g., attached to) the surgical table, and/or such that some of the markers are above the surgical table in the vicinity of the subject's body. For some applications, a plurality of sets of markers are used. For example, multiple sets of markers may be placed adjacently to one another. Alternatively or additionally, one or more sets of markers may be placed on the subject's body such that at least some markers are visible in each of a plurality of x-ray image views, e.g., on the back or stomach and/or chest for the AP or PA views, and on the side of the body for the lateral view. For some applications, a single drape with markers disposed thereon extends, for example, from the back to the side, such that markers are visible in both AP and lateral x-ray image views.

For some applications, a first marker set 50a and second marker set 50b are placed on the subject's body such that, at each (or most) imaging view applied during the procedure for the acquisition of images, at least one of the first and second markers (or a portion thereof) is visible in the acquired images. For example, such as is shown in FIG. 5D, in the case of spinal procedures with a dorsal approach, first and second marker sets 50a and 50b may be placed at the left and right sides of the patient's spine, respectively, and directionally along the spine.

For some applications, only a first set of markers is placed on the subject's body, typically at a position (e.g., along the spine) that enables it to be visible from each (or most) imaging view applied during the procedure for the acquisition of images.

For some applications, a first marker set 50a and a second marker set 50b are each modular. For example, a marker in the form of a notched ruler, may comprise several ruler-like modules. Typically, the number of modules to be actually applied to the subject's body is related to the overall size of the subject, to the location of the targeted vertebra(e) relative to the anatomical reference point (e.g., sacrum) at which placement of the marker sets begins, or to a combination thereof. For example, a target vertebra in the lumbar spine may require one module, a target vertebra in the lower thoracic spine may require two modules, a target vertebra in the upper thoracic spine may require three modules, etc.

Typically, the sets of markers are positioned on either side of the subject's spine such that even in oblique x-ray image views of the intervention site (and neighboring portions of the spine), at least radiopaque markers belonging to one of the sets of markers are visible. Further typically, the sets of markers are positioned on either side of the subject's spine such that even in zoomed-in views acquired from the direction of the tool insertion, or in views that are oblique (i.e., diagonal) relative to the direction of tool insertion, at least radiopaque markers belonging to one of the sets of markers are visible. Typically, the sets of radiopaque markers are placed on the subject, such that the radiopaque markers do not get in the way of either AP or lateral x-ray images of vertebrae, such that the radiopaque markers do not interfere with the view of the surgeon during the procedure, and do not interfere with registration of 2D and 3D image data with respect to one another (which, as described hereinbelow, is typically based on geometry of the vertebrae).

For some applications, the sets of markers as shown in FIG. 5C are used in open-surgery procedures where a large central incision is made along the applicable portion of the spine. For such procedures, a relatively large central window is required for performing the procedure between the two sets of markers. For some applications, the sets of markers as shown in FIG. 5C are used in less invasive, or minimally invasive, surgery as well.

Radiopaque markers 52 are typically in the form of markings (e.g., lines, notches, numbers, characters, shapes) that are visible to the naked eye (i.e., the markings are able to be seen without special equipment) as well as to the imaging that is applied. Typically, the markers are radiopaque such that the markers are visible in radiographic images. Further typically, markers that are placed at respective locations with respect to the subject are identifiable. For example, as shown in FIGS. 5A and 5B respective radiopaque alphanumeric characters are disposed at respective locations. For some applications, markers placed at respective locations are identifiable based upon other features, e.g., based upon the dispositions of the markers relative to other markers. Using a radiographic imaging device (e.g., C-arm 34), a plurality of radiographic images of the set of radiopaque markers are acquired, respective images being of respective locations along at least a portion of the subject's spine and each of the images including at least some of the radiopaque markers.

For some applications, all markings in the marker set are visible both in the x-ray images (by virtue of being radiopaque) and to the naked eye (or optical camera). For some applications, some elements of the marker set are not radiopaque, such that they are invisible in the x-ray images and yet visible to the naked eye (or camera). For example, a central ruler placed on the subject's body may have notches or markings that correspond directly to those of one or both sets of markers that are to the side(s), and yet unlike the latter sets of markers it is not radiopaque. For some applications, when the marker set is placed dorsally, such a ruler facilitates for the surgeon the localization of specific spinal elements (e.g., vertebrae) when looking at the subject's back and yet does not interfere with the view of those same spinal elements in the x-ray images.

The marker set may include a series of discretely identifiable, e.g., distinct, radiopaque symbols (or discernible arrangements of radio-opaque markers), such as is shown in FIG. 5A. For some applications the series of markers may be a series of sequential discretely identifiable radiopaque markers. For some applications, such symbols assist in the stitching of the individual x-ray images into the combined images, by providing additional identifiable registration fiducials for matching a portion of one image with portion of another image in the act of stitching the two images together.

For some applications, sets 50 of markers 52, and/or a rigid radiopaque jig are used to facilitate any one of the following functionalities:
  Vertebra level verification, as described hereinbelow.
  Arriving at a desired vertebra intra-procedurally, without requiring needles to be stuck into the patient, and/or counting along a series of non-combined x-rays.
  Displaying a 3D image of the spine that includes indications of vertebra thereon, using vertebral level verification.
  Determining the correct incision site(s) prior to actual incision(s).
  Identifying changes in a pose of the 2D imaging device (e.g., the x-ray C-arm) and/or a position of the patient. Typically, if the position of the 2D imaging device relative to the subject, or the position of the subject relative to the 2D imaging device, has changed, then in the 2D images there would be a visible change in the appearance of the markers 52 relative to the anatomy within the image. For some applications, in response to detecting such a change, the computer processor generates an alert. Alternatively or additionally, the computer processor may calculate the change in position, and account for the change in position, e.g., in the application of algorithms described herein. Further alternatively or additionally, the computer processor assists the surgeon in returning the 2D imaging device to a previous position relative to the subject. For example, the computer processor may generate directions regarding where to move an x-ray C-arm, in order to replicate a prior imaging position, or the computer processor may facilitate visual comparison by an operator.
  Providing a reference for providing general orientation to the surgeon throughout a procedure.
  Providing information to the computer processor regarding the orientation of image acquisition and/or tool insertion, e.g., anterior-posterior ("AP") or posterior-anterior ("PA"), left lateral or right lateral, etc.
  Generating and updating a visual roadmap of the subject's spine, as described in further detail hereinbelow.

For some applications, at least some of the functionalities listed above as being facilitated by use of sets 50 of markers 52, and/or a rigid jig are performed by computer processor 22 even in the absence of sets 50 of markers 52, and/or a rigid jig, e.g., using techniques as described herein. Typically, sets 50 of markers 52, and/or a rigid jig are used for level verification, the determination of a tool entry point or an incision site, performing measurements using rigid markers as a reference, identifying changes in a relative pose of the 2D imaging device (e.g., the x-ray C-arm) and of the subject, and providing general orientation. All other functionalities of system 20 (such as registration of 2D images to 3D image data and other functionalities that are derived therefrom) typically do not necessarily require the use of sets 50 of markers 52, and/or a rigid jig. The above-described functionalities may be performed automatically by computer processor 22, and/or manually.

Applications of the present invention are typically applied, in non-CAS (the term "non-CAS" also refers to not in the current form of CAS at the time of the present invention) spinal surgery, to one or more procedural tasks including, without limitation:
  Applying pre-operative 3D visibility (e.g., from CT and/or MRI), or 3D visibility gained via image acquisition within the operating room, during the intervention. It is noted that 3D visibility provides desired cross-sectional images (as described in further detail hereinbelow), and is typically more informative and/or of better quality than that provided by intraoperative 2D images. (It is noted that, for some applications, intraoperative 3D imaging is performed.)
  Confirming the vertebra(e) to be operated upon.
  Determining the point(s) of insertion of one or more tools.
  Determining the direction of insertion of one or more tools.

Monitoring tool progression, typically relative to patient anatomy, during insertion.

Reaching target(s) or target area(s).

Exchanging tools while repeating any of the above steps.

Determining tool/implant position within the anatomy, including in 3D.

Generating and updating a visual roadmap of the subject's spine, as described in further detail hereinbelow.

Figure 6:
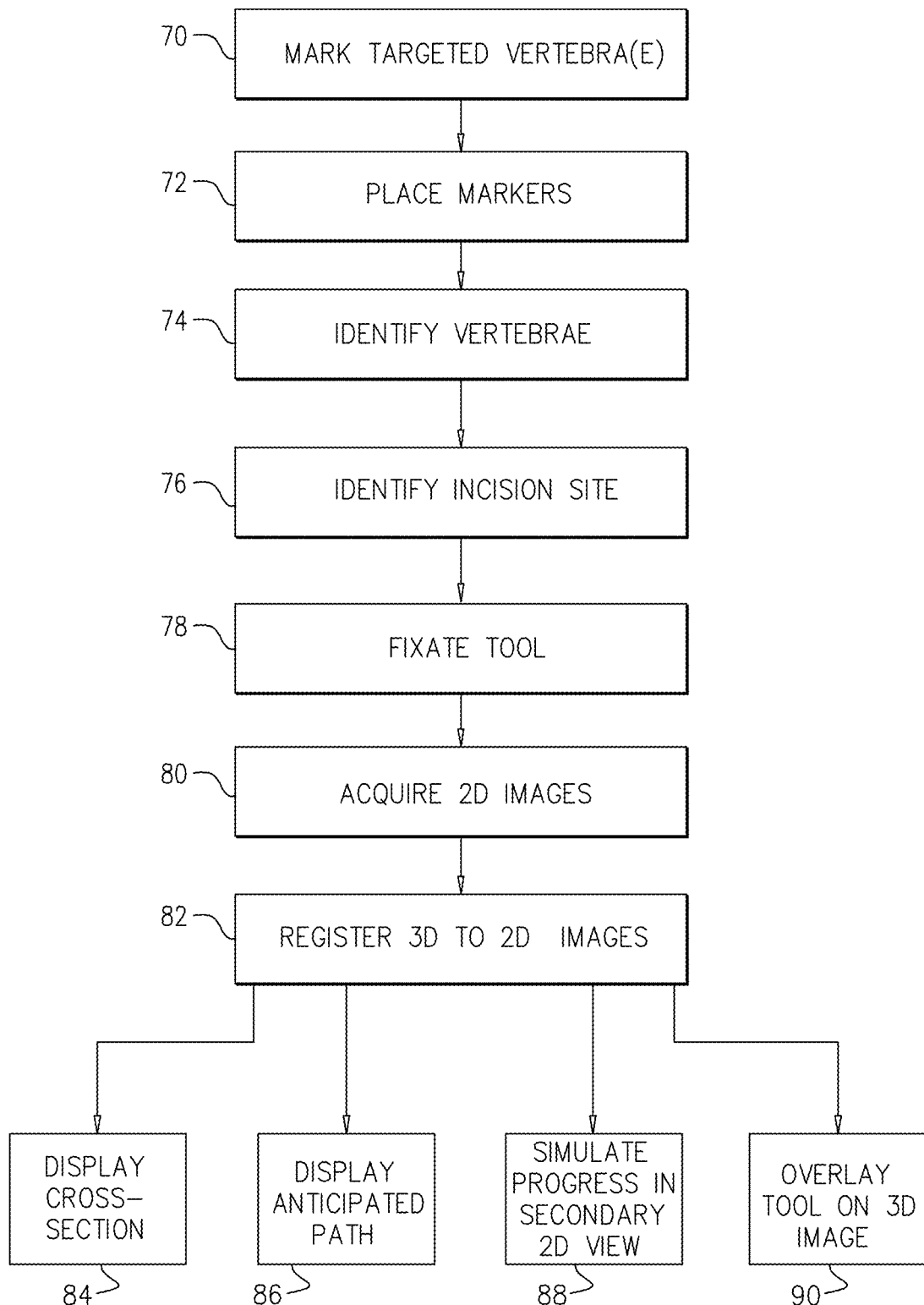
FIG. 6 is a flowchart showing steps that are typically performed using the system of FIG. 1B, in accordance with some applications of the present invention.

Reference is now made to FIG. 6, which is a flowchart showing steps that are typically performed using system 20, in accordance with some applications of the present invention. It is noted that some of the steps shown in FIG. 6 are optional, and some of the steps may be performed in a different order to that shown in FIG. 6. In a first step 70, targeted vertebra(e) are marked by an operator with respect to 3D image data (e.g., a 3D image, a 2D cross-section derived from 3D image data, and/or a 2D projection image derived from 3D image data) of the subject's spine. For some applications, in a second step 72, sets 50 of markers 52 are placed on the subject, underneath the subject, on the surgical table, or above the surgical table in a vicinity of the subject. For some applications, step 72 is performed prior to step 70. Typically, in a third step 74, vertebrae of the spine are identified in order to verify that the procedure is being performed with respect to the correct vertebra (a step which is known as "level verification"), using radiographic images of the spine and the markers to facilitate the identification, or alternatively, using registration of 2D x-ray images with the 3D image data, as further described hereinbelow. In a fourth step 76, an incision site, e.g., a skin-level incision site, (typically in the case of minimally-invasive or less-invasive surgery) or a tool entry point, e.g., a skeletal-portion-level entry point, (typically in the case of open surgery) is determined. Throughout this document, the term "incision site" (or "site of incision") refers to the site of making an incision of limited size, typically in the course of minimally-invasive and less-invasive surgery, while the term "entry point" (or "point of entry") typically refers to a point at which a tool enters a targeted skeletal element such as a vertebra. However, the two terms may be also used interchangeably when describing certain applications of the present invention, or for example an incision site may be referred to as a skin-level insertion point. For some applications, in a fifth step 78, the first tool in the sequence of tools (which in less-invasive surgery is often a needle, e.g., a Jamshidi™ needle) is typically inserted into the subject (e.g., in the subject's back), and is slightly fixated in the vertebra.

For some applications, in step 78 a tool (which in more-invasive surgery is often a pedicle finder) is not yet inserted but rather is positioned relative to a vertebra, wherein such vertebra is often partially exposed at such phase, either manually or using a holder device that is typically fixed to the surgical table. Such holder device typically ensures that the subsequent acquisition in step 80 of two or more 2D radiographic images prior to actual tool insertion are with the tool at a same position relative to the vertebra. For some applications, motion of the applicable portion of the subject in between the acquisition of the two or more images is detected by means of a motion detection sensor as described later in this document. For some applications, if motion is detected that the acquisition of pre-motion images may be repeated.

In a sixth step 80, two or more 2D radiographic images are acquired from respective views that typically differ by at least 10 degrees, e.g., at least 20 degrees (and further typically by 30 degrees or more), and one of which is typically from the direction of insertion of the tool. Typically, generally-AP and generally-lateral images are acquired. Alternatively or additionally, images from different views are acquired. In a seventh step 82, computer processor 22 of system 20 typically registers the 3D image data to the 2D images, as further described hereinbelow.

Subsequent to the registration of the 3D image data to the 2D images additional features of system 20 as described in detail hereinbelow may be applied by computer processor 22. For example, in step 84, the computer processor drives display 30 to display a cross-section derived from the 3D image data at a current location of the tip of a tool as identified from a 2D image, and, optionally, to show a vertical line on the cross-sectional image indicating a line within the cross-sectional image somewhere along which the tip of the tool is currently disposed.

It is noted, that, as described in further detail hereinbelow, for some applications, in order to perform step 84, the acquisition of one or more 2D x-ray images of a tool at a first location inside the vertebra is from only a single x-ray image view, and the one or more 2D x-ray images are registered to the 3D image data by generating a plurality of 2D projections from the 3D image data, and identifying a 2D projection that matches the 2D x-ray images of the vertebra. In response to registering the one or more 2D x-ray images acquired from the single x-ray image view to the 3D image data, the computer processor drives a display to display a cross-section derived from the 3D image data at a the first location of a tip of the tool, as identified from the one or more 2D x-ray images, and optionally to show a vertical line on the cross-sectional image indicating a line within the cross-sectional image somewhere along which the first location of the tip of the tool is disposed. Typically, when the tip of the tool is disposed at an additional location with respect to the vertebra, further 2D x-ray images of the tool at the additional location are acquired from the same single x-ray image view, or a different single x-ray image view, and the above-described steps are repeated. Typically, for each location of the tip of the tool to which the above-described technique is applied, 2D x-ray images need only be acquired from a single x-ray image view, which may stay the same for the respective locations of the tip of the tool, or may differ for respective locations of the tip of the tool. Typically, two or more 2D x-rays are acquired from respective views, and the 3D image data and 2D x-ray images are typically registered to the 3D image data (and to each other) by identifying a corresponding number of 2D projections of the 3D image data that match respective 2D x-ray images. In step 86, the computer processor drives display 30 to display the anticipated (i.e., extrapolated) path of the tool with reference to a target location and/or with reference to a desired insertion vector. In step 88, the computer processor simulates tool progress within a secondary 2D imaging view, based upon observed progress of the tool in a primary 2D imaging view. In step 90, the computer processor overlays an image of the tool, a representation thereof, and/or a representation of the tool path upon the 3D image data (e.g., a 3D image, a 2D cross-section derived from 3D image data, and/or a 2D projection image derived from 3D image data), the location of the tool or tool path having been derived from current 2D images.

Figure 7:
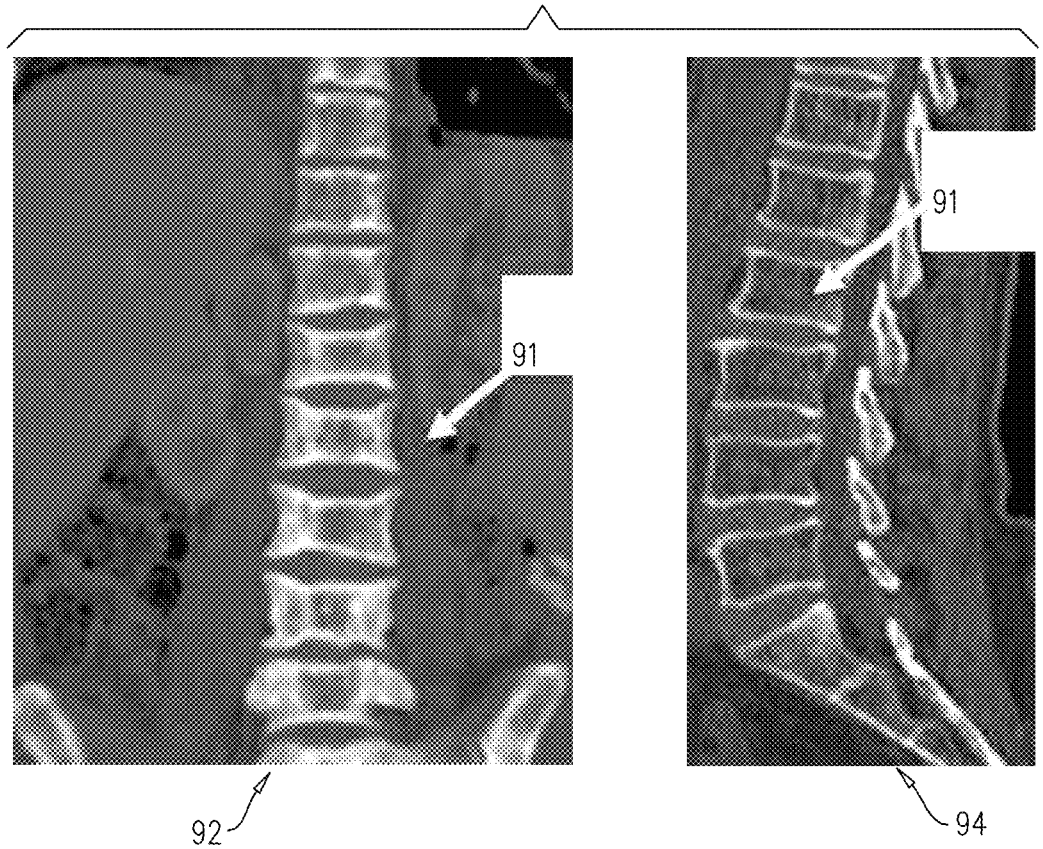
FIG. 7 shows a vertebra designated upon cross-sectional images of a subject's spine that are derived from 3D image data, in accordance with some applications of the present invention.

Reference is now made to FIG. 7, which shows a vertebra 91 designated upon a coronal cross-sectional image 92 and upon a sagittal cross-sectional image 94 of a subject's spine, the cross-sectional images being derived from 3D image data, in accordance with some applications of the present invention. For some applications, such images are the Preview images that are often generated at the beginning of a 3D scan. For some applications, such images are derived from the 3D scan data, such as by using a DICOM Viewer. As described hereinabove with reference to step 70 of FIG. 6, typically prior to the subject being placed into the operating room, or while the subject is in the operating room but before an intervention has commenced, an operator marks the targeted vertebra(e) with respect to the 3D image data (e.g., a 3D image, a 2D cross-section derived from 3D image data, and/or a 2D projection image derived from 3D image data). For some applications, in response to the operator marking one vertebra, the computer processor designates additional vertebra(e). For some applications, the operator marks any one of, or any combination of, the following with respect to the 3D image data: a specific target within the vertebra (such as a fracture, a tumor, etc.), desired approach directions/vectors for tool insertion as will be further elaborated below, and/or desired placement locations of implants (such as pedicle screws). For some applications, the operator marks the targeted vertebra with respect to a 2D x-ray image that has a sufficiently large field of view to encompass an identifiable portion of the anatomy (e.g., the sacrum) and the targeted vertebra(e). For some applications, more than one targeted vertebra is marked, for example vertebrae that are to be fixated to and/or fused to one another, and for some applications, two or more vertebra(e) that are not adjacent to one another are marked.

For some applications, the computer processor automatically counts the number of vertebrae on the image from an identifiable anatomical reference (e.g., the sacrum) to the marked target vertebra(e). It is then known that the targeted vertebra(e) is vertebra N from the identifiable anatomical reference (even if the anatomical labels of the vertebra(e) are not known). For some applications, the vertebra(e) are counted automatically using image-processing techniques. For example, the image-processing techniques may include shape recognition of anatomical features (of vertebrae as a whole, of traverse processes, and/or of spinous processes, etc.). Or, the image-processing techniques may include outer edge line detection of spine (in a 2D image of the spine) and then counting the number of bulges along the spine (each bulge corresponding to a vertebra). For some applications, the image-processing techniques include techniques described in US 2010-0161022 to Tolkowsky, which is incorporated herein by reference. For some applications, the vertebra(e) are counted manually by the operator, starting with the vertebra nearest the anatomical reference and till the targeted vertebra(e).

Referring to step 72 of FIG. 6 in more detail, for some applications, in which a procedure is performed on a given vertebra of the subject's spine, one or more sets 50 of radiopaque markers 52 are placed upon or near the subject, such that markers that are placed at respective locations with respect to the subject are identifiable, e.g., as shown in FIGS. 5A-C. For example, as shown in FIGS. 5A and 5B respective radiopaque alphanumeric characters are disposed at respective locations. For some applications, markers placed at respective locations are identifiable based upon other features, e.g., based upon the dispositions of the markers relative to other markers. Using a radiographic imaging device (e.g., C-arm 34), a plurality of radiographic images of the set of radiopaque markers are acquired, respective images being of respective locations along at least a portion of the subject's spine and each of the images including at least some of the radiopaque markers. Using computer processor 22, locations of the radiopaque markers within the radiographic images are identified, by means of image processing. At least some of the radiographic images are combined with respect to one another based upon the identified locations of the radiopaque markers within the radiographic images. Typically, such combination of images is similar to stitching of images. However, the images are typically not precisely stitched such as to stitch portions of the subject's anatomy in adjacent images to one another. Rather, the images are combined with sufficient accuracy to be able to determine a location of the given vertebra N within the combined radiographic images.

For some applications, based upon the combined radiographic images, the computer processor automatically determines a location of the given vertebra (e.g., the previously-marked targeted vertebra) within the combined radiographic images. For some applications, the computer processor automatically determines location of the given vertebra within the combined radiographic images by counting the number of vertebrae on said image from an identifiable anatomical reference (e.g., the sacrum). For some applications, the counting is performed until the aforementioned N. For some applications, the counting is performed until a value that is defined relative to the aforementioned N. For some applications, the vertebra(e) are counted automatically using image-processing techniques. For example, the image-processing techniques may include shape recognition of anatomical features (of vertebrae as a whole, of traverse processes, and/or of spinous processes, etc.). Or, the image-processing techniques may include outer edge line detection of spine (in a 2D image of the spine) and then counting the number of bulges along the spine (each bulge corresponding to a vertebra). For some applications, the image-processing techniques include techniques described in US 2010-0161022 to Tolkowsky, which is incorporated herein by reference. For some applications, the computer processor facilitates manual determination of the location of the given vertebra within the combined radiographic images by displaying the combined radiographic images. For some applications, based upon the combined radiographic images, the operator manually determines, typically by way of counting vertebrae upon the combined images starting at the anatomical reference, a location of the given vertebra (e.g., the previously-marked targeted vertebra) within the combined radiographic images.

For some applications, the marker sets as observed in the stitched x-ray images are overlaid, typically automatically and by means of image processing, upon the corresponding CT images of the spine or of the applicable spinal portions. For some applications, that facilitates subsequent matching by the user between corresponding skeletal elements in the stitched x-ray and in the CT images.

Figure 8A:
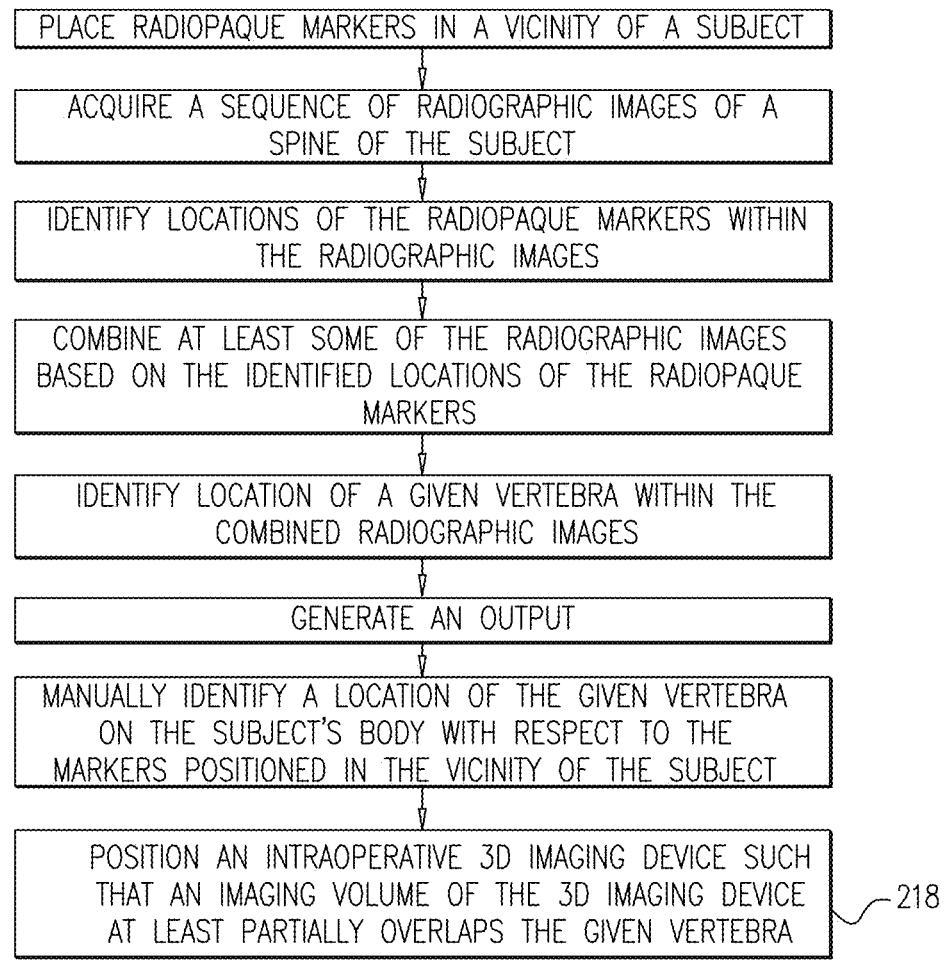
FIG. 8A is a flow chart showing a method for level verification with an additional step of positioning an intraoperative 3D imaging device, in accordance with some applications of the present invention.

Reference is now made to FIG. 8A, which is a flow chart showing the abovementioned method for level verification with the additional step 218 of positioning an intraoperative 3D imaging device. Based upon the location of the given vertebra within the combined radiographic images, a location of the given vertebra in relation to the set of radiopaque markers that is placed on or near the subject is determined. An intraoperative 3D imaging device can then be positioned such that an imaging volume of the 3D imaging device at least partially overlaps the given vertebra.

It is noted that in the absence of sets 50 of markers 52, the typical methodology for determining the location of a given vertebra includes acquiring a series of x-rays along the patient's spine from the sacrum, and sticking radiopaque needles into the subject in order to match the x-rays to one another. Typically, in each x-ray spinal image only 3-4 vertebrae are within the field of view, and multiple, overlapping images must be acquired, such as to enable human counting of vertebra using the overlapping images. This technique may also involve switching back and forth between AP and lateral x-ray images. This method is often time-consuming and radiation-intensive.

A known clinical error is wrong-level surgery, as described, for example, in "Wrong-Site Spine Surgery: An Underreported Problem? AAOS Now," American Association of Orthopedic Surgeons, March 2010. That further increases the desire for facilitating level verification by applications of the present invention, as described herein.

Figure 8B:
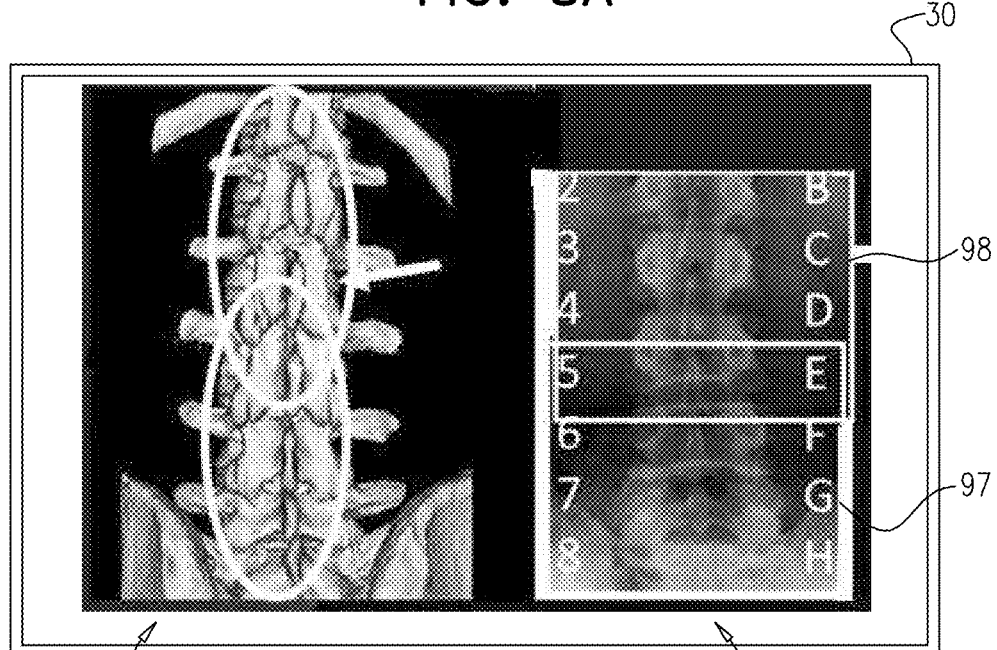
FIG. 8B shows an example of a 3D CT image of a subject's spine displayed alongside a combined radiographic image of the subject's spine, in accordance with some applications of the present invention.

Reference is now made to FIG. 8B which shows an example of a 3D CT image 95 of a subject's spine displayed alongside a combined radiographic image 96 of the subject's spine, in accordance with some applications of the present invention. In accordance with some applications of the present invention, set 50 of markers 52 is placed upon or near the subject, such that the bottom of the set of markers is disposed over, or in the vicinity of, the sacrum. (and in particular the upper portion thereof, identifiable in the x-ray images). A sequence of x-ray images from generally the same view as one another are acquired along the spine, typically, but not necessarily, with some overlap between adjacent images. Typically, the specific pose of the x-ray C-arm when acquiring each of the images is not known, the C-arm is not tracked by a tracker nor are its exact coordinates relative to the subject's body (and more specifically the applicable portion thereof) known. The sequence of x-ray images is typically acquired from a generally-AP view, but may also be acquired from a different view, such as a generally-lateral view. Using computer processor 22, locations of the radiopaque markers within the radiographic images are identified, by means of image processing. At least some of the radiographic images are combined with respect to one another based upon the identified locations of the radiopaque markers within the radiographic images. For example, combined radiographic image 96 is generated by combining (a) a first x-ray image 97 acquired from a generally-AP view and which starts at the subject's sacrum and which includes markers H-E of the right marker set and markers 8-5 of the left marker set with (b) second x-ray image 98 acquired from a generally similar view to the first view (but one which is not exactly the same) and which includes markers E-B of the right marker set and markers 5-2 of the left marker set. As noted previously, the aforementioned markers may be alphanumeric, or symbolic, or both.

(It is noted that in FIG. 8B the alphanumeric markers appear as white in the image. In general, the markers may appear as generally white or generally black, depending on (a) the contrast settings of the image (e.g., do radiopaque portions appear as white on a black background, or vice versa), and (b) whether the markers are themselves radiopaque, or the markers constitute cut-outs from a radiopaque backing material, as is the case, in accordance with some applications of the present invention.)

Typically, the combination of images is similar to stitching of images. However, the images are often not precisely stitched such as to stitch portions of the subject's anatomy in adjacent images to one another. Rather, the images are combined with sufficient accuracy to facilitate counting vertebrae along the spine within the combined image. The physical location of a given vertebra is then known by virtue of it being adjacent to, or in the vicinity of, or observable in the x-ray images relative to, a given one of the identifiable markers. It is noted that in order to combine the radiographic images to one another, there is typically no need to acquire each of the images from an exact view (e.g., an exact AP or an exact lateral view), or for there to be exact replication of a given reference point among consecutive images. Rather, generally maintaining a given imaging direction, and having at least some of the markers generally visible in the images is typically sufficient.

As described hereinabove, for some applications, the computer processor automatically counts (and, for some applications, labels, e.g., anatomically labels, and/or numerically labels) vertebrae within the combined radiographic images in order to determine the location of the previously-marked target vertebra(e), or other vertebra(e) relative to the previously marked vertebra. Alternatively, the computer processor drives the display to display the combined radiographic images such as to facilitate determination of the location of the previously-marked target vertebra(e) by an operator. The operator is able to count to the vertebra within the combined radiographic images, to determine, within the combined images, which of the radiopaque markers are adjacent to or in the vicinity of the vertebra, and to then physically locate the vertebra within the subject by locating the corresponding physical markers.

Figure 8C:
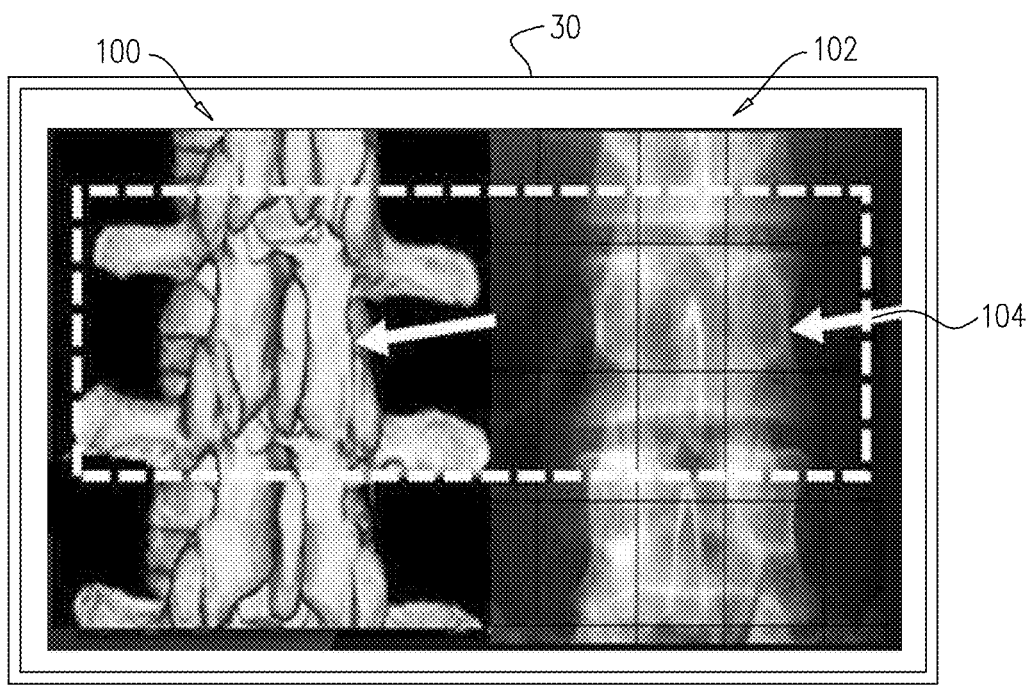
FIG. 8C shows the designated vertebra indicated on a 3D CT image and on a 2D x-ray image, the CT image and x-ray image being displayed alongside one another, in accordance with some applications of the present invention.
Figure 8D:
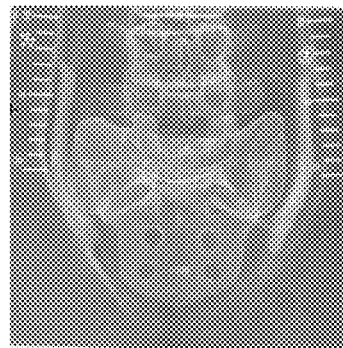
FIGS. 8D-8I, show an example of generating a combined spinal image from four individual x-ray images that were acquired sequentially along the spine, in accordance with some applications of the present invention.
Figure 8E:
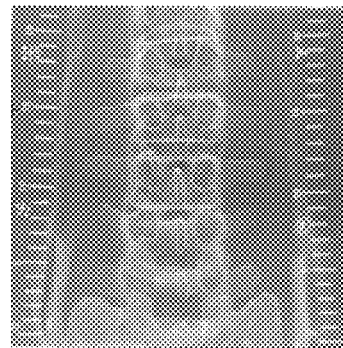
Figure 8F:
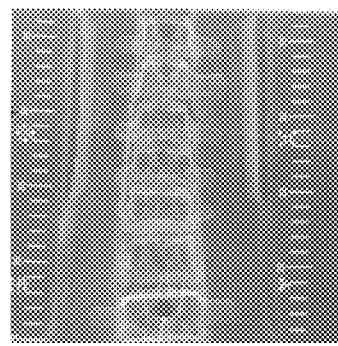
Figure 8G:
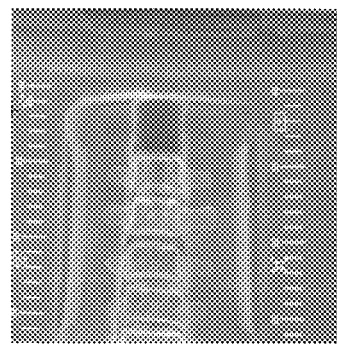
Figure 8H:
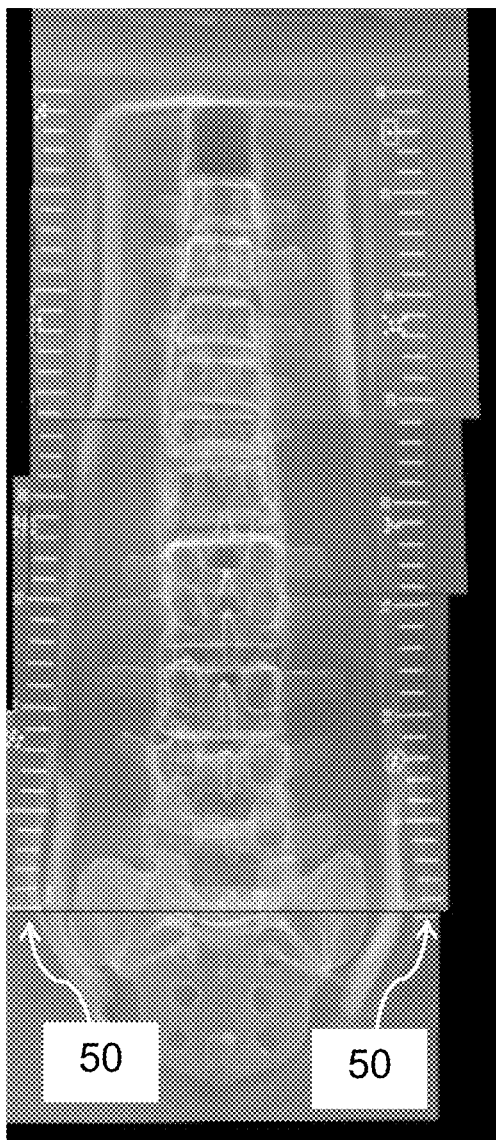
Figure 8I:
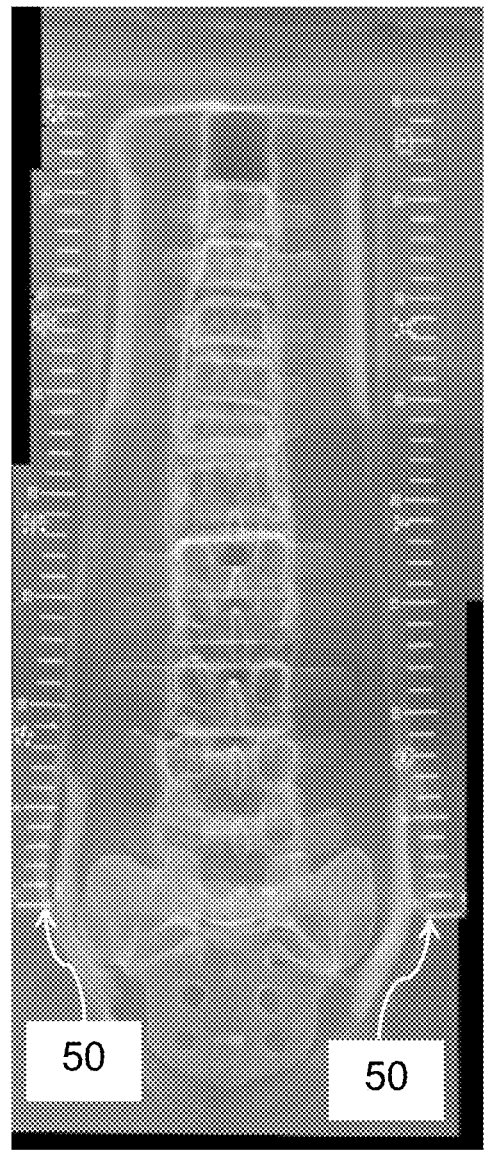

Reference is now made to FIG. 8C, which shows an example of a 3D CT image 100 of the subject's spine displayed alongside a 2D radiographic image 102 of the subject's spine, in accordance with some applications of the present invention. As shown, markers 52 appear on the combined radiographic image. As shown, vertebra 91, which was identified by an operator with respect to the 3D image data (as described hereinabove with reference to FIG. 8A), has been identified within the 2D radiographic image using the above-described techniques, and is denoted by cursor 104.

For some applications, a spinal CT image data (in 3D or a 2D slice) matching the viewing direction from which the x-ray images were acquired is displayed concurrently with the stitched x-ray images. For example, in the case of x-ray images acquired from a generally-AP direction, a coronal CT view is displayed. For some applications, the x-ray images, or the stitched x-ray image, are interconnected with the CT image such that when the user (or the system) selects a vertebra on the x-ray, the same vertebra is indicated/highlighted on the CT image, or vice versa. For some applications, such connection is generated by registering one or more DRRs of the spine as a whole, or of the corresponding spinal section, or of one or more individual vertebrae, with the x-ray images or stitched image. For some applications, such connection is generated by other means of image processing, including in accordance with techniques described hereinabove in the context of counting vertebrae.

For some applications, generation of the combined image includes blending the edges of individual x-ray images from which the combined image is generated, typically resulting in a more continuous-looking combined image.

Reference is now made to FIGS. 8D-I, which show, in accordance with applications of the present invention, an example of generating a combined spinal image from four individual x-ray images, shown respectively in FIGS. 8D-G, that were acquired sequentially along the spine, with each individual x-ray image showing a portion of the spine. Marker sets 50, each comprising a numbered radio-opaque ruler coupled with identifiable arrangements of radio-opaque elements, are placed along both sides of the spine. A portion of one or both marker sets 50 is visible in each of the x-ray images in FIGS. 8D-G. The combined image shown in FIG. 8H was generated by stitching the four x-ray images with the help of marker sets 50 and in accordance with techniques described hereinabove. For generating the combined image shown in FIG. 8I, blending was applied to corresponding edges of x-ray images of FIGS. 8D-G.

For some applications, 2D x-ray images of the subject's spine, or of a portion thereof, are stitched into a combined image, or are related spatially to one another without actually stitching them, by using 3D image data of the subject's spine (or of a portion thereof) as a "bridge," and as described hereinbelow.

For some applications, the 3D image data comprises all of the spinal portions visible in the x-ray images. For some applications, the 3D image data comprises only some of the spinal portions visible in the x-ray images.

For some applications, a plurality of 2D x-ray images are acquired, respective images being of respective locations along at least a portion of the subject's spine. For some applications, all images are acquired from a similar viewing angle, for example an angle that is approximately AP. For some applications, images are acquired from different viewing angles.

For some applications, some or all of the images are acquired with some overlap between consecutive two images with respect to the skeletal portion visible in each of them. For some applications, some or all of the images are acquired with small gaps (typically a portion of a vertebra) between consecutive two images with respect to the skeletal portion visible in each of them.

For some applications, the images are stitched to one another, typically without using radiopaque markers, and while using the subject's 3D image data, to provide a combined image of the spine or of a portion thereof, by a computer processor that performs the following:
  i. Each newly-acquired x-ray image is registered with 3D image data of the subject's spine, using Digitally Reconstructed Radiographs (DRRs) as described by embodiments of the present invention.
  ii. As a result, vertebrae visible in each x-ray image become associated with corresponding vertebrae in the 3D image data.
  iii. As a result, for example: vertebrae that are visible, in whole or in part, in both x-ray images, are identified as being the same vertebrae; alternatively or additionally, vertebrae that are visible in any two images relating to neighboring portions of the spine, are identified with respect to their anatomical positions relative to one another.
  iv. The two x-ray images are now stitched such that vertebrae (or portions of vertebrae) visible in each of the images are now overlaid upon one another, or the images are placed along one another in a manner that represents the subject's anatomy, all in accordance with the positions of those vertebrae along the subject's spine.

Alternatively of additionally, the vertebrae visible in each of the x-ray images are marked as such upon the 3D image data. For some applications, the vertebrae visible in each x-ray image may be related to, or marked on, a sagittal view, or a sagittal cross-section, of the 3D image data. For some applications, the vertebrae visible in each x-ray image may be marked on a coronal view, or a coronal cross-section, of the 3D image data.

For example, if vertebrae L5, L4, L3 and L2 are visible in a first x-ray image, and vertebra L2, L1, T12 and T11 are visible in a second x-ray image:
  The first x-ray image and the second x-ray image, typically if acquired from similar views, are stitched to one another with vertebra L2 (or a portion thereof) being the overlapping section, typically creating a combined image;
  Alternatively, the first x-ray image and the second x-ray image, typically if acquired from non-similar views, are displayed relative to one another such that vertebra L2 (or a portion thereof) is at a parallel position in both;
  Alternatively, the first x-ray image and the second x-ray image are displayed as related to a sagittal view, or a sagittal cross-section, of the 3D image data for vertebra L5 through T11, such that the first x-ray image is related, typically visually, to vertebrae L5 through L2 and the second x-ray image is related, typically visually, to vertebrae L2 through T11;
  Alternatively, the first x-ray image and the second x-ray image are displayed as related to a coronal view, or a coronal cross-section, of the 3D image data for vertebra L5 through T11, such that the first x-ray image is related, typically visually, to vertebrae L5 through L2 and the second x-ray image is related, typically visually, to vertebrae L2 through T11.

Alternatively, for example, if vertebrae L5, L4, L3 and L2 are visible in a first x-ray image, and vertebra L1, T12, T11 and T10 are visible in a second x-ray image:
  The first x-ray image and the second x-ray image are displayed relative to one another such that vertebra L2 in the first x-ray image is adjacent to vertebra L1 in the second x-ray image;
  The first x-ray image and the second x-ray image are displayed within a combined image, relative to one another such that vertebra L2 in the first x-ray image is adjacent to vertebra L1 in the second x-ray image within the combined image;
  Alternatively, the first x-ray image and the second x-ray image are displayed as related to a sagittal view, or a sagittal cross-section, of the 3D image data for vertebra L5 through T10, such that the first x-ray image is related, typically visually, to vertebrae L5 through L2, and the second x-ray image is related, typically visually, to vertebrae L1 through T10;
  Alternatively, the first x-ray image and the second x-ray image are displayed as related to a coronal view, or a coronal cross-section, of the 3D image data for vertebra L5 through T11, such that the first x-ray image is related, typically visually, to vertebrae L5 through L2 and the second x-ray image is related, typically visually, to vertebrae L1 through T10.

For some applications, the techniques described hereinabove are further applied for level verification, optionally in combination with other techniques described herein.

Figure 32:
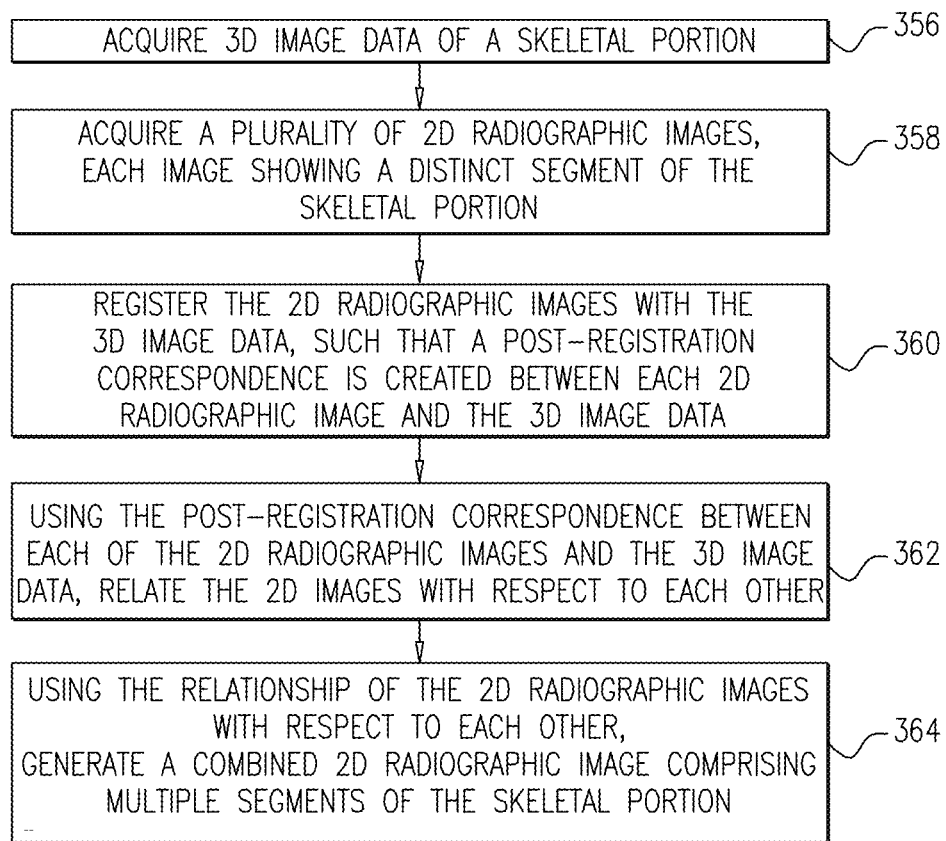
FIG. 32 is a flow chart showing a method for image stitching, in accordance with some applications of the present invention.

Thus, reference is now made to FIG. 32, which is a flow chart showing a method for image stitching, in accordance with some applications of the present invention, and comprising the following steps:
  (i) acquiring 3D image data of a skeletal portion (step 356),
  (ii) acquiring a plurality of 2D radiographic images, each image showing a distinct segment of the skeletal portion (step 358)
  (iii) registering the 2D radiographic images with the 3D image data, such that a post-registration correspondence is created between each 2D radiographic image and the 3D image data (step 360),
  (iv) using the post-registration correspondence between each of the 2D radiographic images and the 3D image data, relating the 2D images with respect to each other (step 360), and (v) using the relationship of the 2D radiographic images with respect to each other, generating a combined 2D radiographic image comprising multiple segments of the skeletal portion (step 362).

Figure 9A:
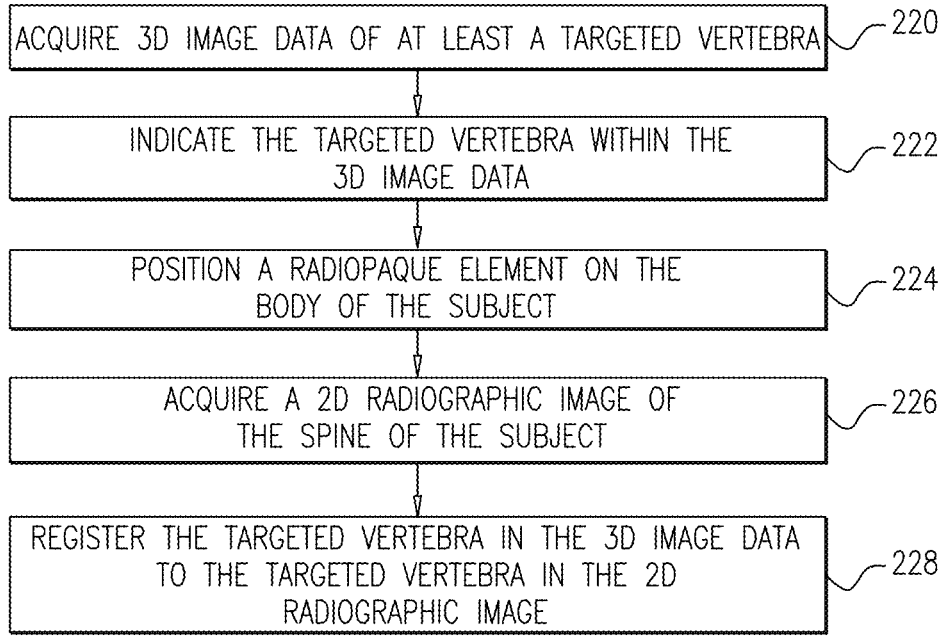
FIGS. 9A and 9B are flow charts showing another method for performing level verification, in accordance with some applications of the present invention.
Figure 9B:
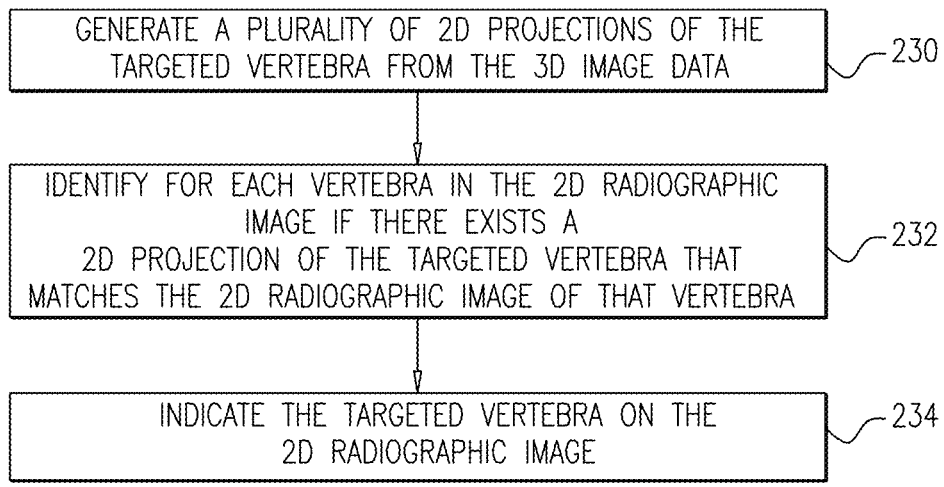

Reference is now made to FIGS. 9A-B, which are flow charts showing another method for performing "level verification," in accordance with some applications of the present invention. After acquiring 3D image data of at least a target vertebra (step 220), using at least one computer processor, the targeted vertebra is indicated within the 3D image data (step 222). A radiopaque element that is typically also visible to the naked eye, e.g., the tip of a surgical tool, such as a scalpel, or set 50 of radiopaque markers 52, is positioned on the body of the subject (step 224) with respect to the spine such that the radiopaque element appears in 2D radiographic images that acquired of the spine (step 226). Computer processor 22 then identifies the targeted vertebra in the 2D radiographic image by registering the targeted vertebra in the 3D image data to the targeted vertebra in the 2D radiographic image (step 228). As shown by the flowchart in FIG. 9B, to do the registration, computer processor 22 attempts to register each vertebra that is visible in the 2D radiographic image to the targeted vertebra in the 3D image data until a match is found by generating a plurality of 2D projections of the targeted vertebra from the 3D image data (step 230) and for each vertebra that is visible in the 2D radiographic image, identifying if there exists a 2D projection of the targeted vertebra that matches the 2D radiographic image of that vertebra (step 232). Once the targeted vertebra has been identified it is indicated on the 2D radiographic image (step 234) such that a location of the targeted vertebra is now identified with respect to radiopaque element.

It should also be noted that level verification using embodiments of the present invention is also useful for correctly positioning a 3D imaging device (such as an O-arm or a 3D x-ray device), situated within the operating room, relative to the subject's body and prior to an actual 3D scan. A common pre-operative CT or MRI device is, according to the specific scan protocol being used, typically configured to scan along an entire body portion such as a torso. For example, such scan may include the entire lumbar spine, or the entire thoracic spine, or both. In contrast, the aforementioned 3D imaging devices available inside some operating rooms, at the time of the present invention, have a very limited scan area, typically a cubical volume whose edges are each 15-20 cm long. Thus, correct positioning of such 3D imaging device prior to the scan relative to the subject's spine, and in particular relative to the targeted spinal elements, is critical for ensuring that the targeted vertebra(e) are indeed scanned. For some applications, level verification using aforementioned embodiments of the present invention yields an indication to the operator of those visible elements of the marker set, next to which the 3D imaging device should be positioned for scanning the spinal segment desired to be subsequently operated upon, such that an imaging volume of the 3D imaging device at least partially overlaps the targeted vertebra. For some applications, in the operating room, the targeted vertebra(e) are level-verified using embodiments of the present invention and then the 3D imaging device is positioned such that its imaging volume (whose center is often indicated by a red light projected upon the subject's body, or some similar indication) coincides with the targeted vertebra(e). For example, if the marker set is a notched ruler placed on the subject's body along the spine, then using embodiments of the present invention the operator may realize that the 3D imaging device should be positioned such that its red light is projected on the subject's body at a level that is in between notches #7 and #8 of the ruler.

For some applications, when a vertebra is selected in an x-ray image (acquired at any phase of the medical procedure) or a combined x-ray image, a 3D image of the same vertebra is displayed automatically. For some applications, the 3D vertebral image auto-rotates on the display. For some applications, the 3D vertebral image is displayed with some level of transparency, allowing the user to observe tools inserted in the vertebra, prior planning drawn on the vertebra, etc. the selection of the vertebra may be by the user or by the system. The autorotation path (i.e., the path along which the vertebra rotates) may be 2D or 3D, and may be system-defined or user-defined. The level of transparency may be system-defined or user-defined. The same applies not only to vertebrae, but also to other spinal or skeletal elements.

For some applications, based upon counting and/or labeling of the vertebrae in the combined radiographic image, computer processor 22 of system 20 counts and/or labels vertebrae within the 3D image data (e.g., a 3D image, a 2D cross-section derived from 3D image data, and/or a 2D projection image derived from 3D image data). For some applications, the computer processor drives the display to display the labeled vertebrae while respective corresponding 2D images are being acquired and displayed. Alternatively or additionally, the computer processor drives the display to display the labeled vertebrae when the combined radiographic image has finished being generated and/or displayed. It is noted that, typically, the computer processor counts, labels, and/or identifies vertebrae on the 3D image data and on the 2D radiographic images without needing to determine relative scales of the 3D image data and 2D images. Rather, it is sufficient for the computer processor to be able to identify individual vertebrae at a level that is sufficient to perform the counting, labeling, and/or identification of vertebrae.

It is noted that the above-described identification of vertebrae that is facilitated by markers 52 is not limited to being performed by the computer processor at the start of an intervention. Rather, the computer processor may perform similar steps at subsequent stages of the procedure. Typically, it is not necessary for the computer processor to repeat the whole series of steps at the subsequent stages, since the computer processor utilizes knowledge of an already-identified vertebra, in order to identify additional vertebrae. For example, after identifying and then performing a procedure with respect to a first vertebra, the computer processor may utilize the combined radiographic image to derive a location of a further target vertebra (which may be separated from the first vertebra by a gap), based upon the already-identified first vertebra. For some applications, in order to derive the location of a further target vertebra, the computer processor first extends the combined radiographic image (typically, using the markers in order to do so, in accordance with the techniques described hereinabove).

Figure 10:
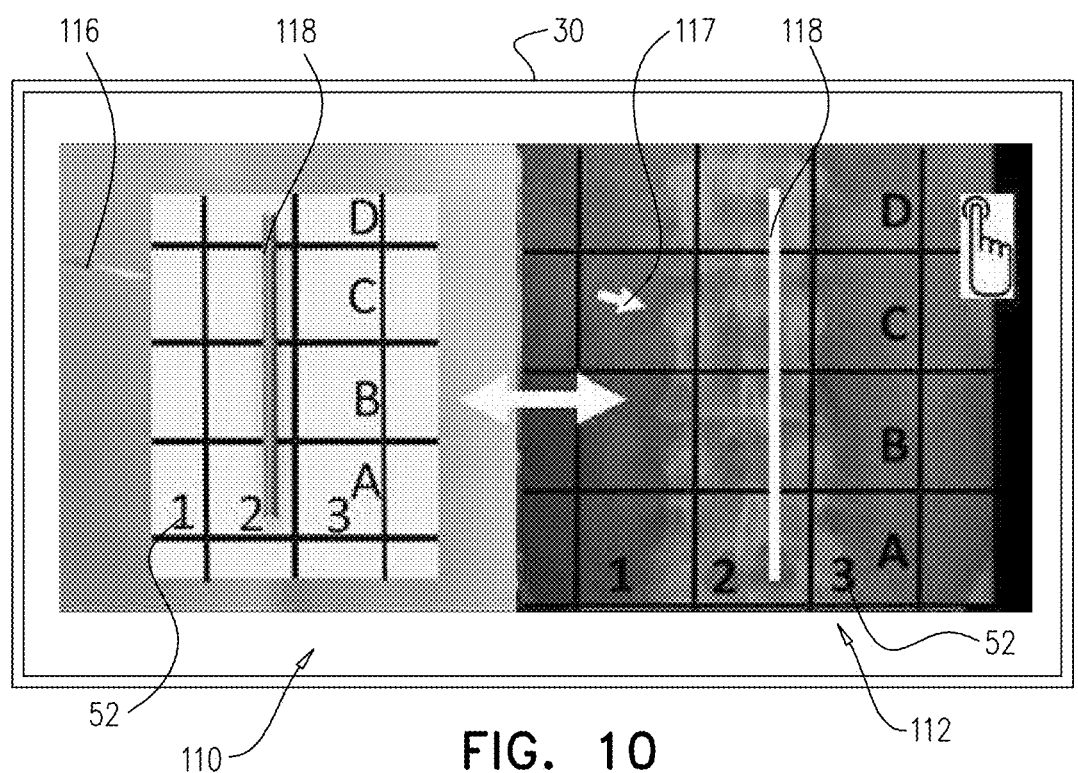
FIG. 10 shows an example of an optical image displayed alongside a 2D radiographic image, in accordance with some applications of the present invention.

Reference is now made to FIG. 10, which shows an example of an optical image 110 displayed alongside a 2D radiographic (e.g., x-ray) image 112, in accordance with some applications of the present invention. As described with reference to step 76 of FIG. 6, subsequent to identifying a target vertebra along the subject's spine, typically, the operator determines a desired site for an incision or tool insertion. For some applications, in order to facilitate the determination of the incision site or tool insertion site, an optical camera 114 is disposed within the operating room such that the optical camera has a generally similar viewing angle to that of the 2D radiographic imaging device. For example, the camera may be disposed on x-ray C-arm 34, as shown in FIG. 1. Alternatively or additionally, the camera may be disposed on a separate arm, may be handheld, may be the back camera of a display such as a tablet or mini-tablet device, and/or may be held by another member of the operating room staff. For some applications, the camera is placed on the surgeon's head. Typically, for such applications, the surgeon uses a head-mounted display.

For some applications, a 2D radiographic image 112 of a portion of the subject's body is acquired in a radiographic imaging modality, using the 2D radiographic imaging device (e.g., C-arm 34), and an optical image 110 of the subject's body is acquired in optical imaging modality, using optical camera 114 (shown in FIG. 1). Computer processor 22 of system 20 identifies radiopaque markers (e.g., markers 52) in the radiographic image and in the optical image, by means of image processing. By way of example, in FIG. 10, radiopaque gridlines and alphanumeric radiopaque markers associated with the radiopaque gridlines are visible in both the radiographic and the optical image. Based upon the identification of the radiopaque markers in the radiographic image and in the optical image, the computer processor bidirectionally maps the radiographic image and the optical image with respect to one another. It is noted that acquisition of the radiographic image and the optical image from generally-similar views (but not necessarily identical views) is typically sufficient to facilitate the bidirectional mapping of the images to one another, by virtue of the radiopaque markers that are visible in both of the images.

For some applications, the radiographic image and the optical image are fused with one another and displayed as a joint image. For some applications, any of the images is adjusted (e.g. scaled, distorted, etc.), typically according to elements of the marker set observed in both images, prior to such fusion. For some applications, only the x-ray image is displayed to the operator, with the location of the tool (e.g., knife) positioned upon the subject identified from the optical image and marked upon the x-ray image.

As shown in FIG. 10, for some applications, the computer processor drives display 30 to display the radiographic image and the optical image separately from one another, upon one or more displays. Subsequently, in response to receiving an input indicating a location in a first one of the radiographic and the optical images, the computer processor generates an output indicating the location in the other one of the radiographic and the optical images. For example, in response to a line or a point being marked on 2D x-ray image 112, the computer processor indicates a corresponding lines or points overlaid on the optical image 110. Similarly, in response to a line or a point being marked on optical image 110, the computer processor indicates a corresponding lines or points overlaid on the 2D x-ray image 112. Further similarly, in response to a line or a point being marked on, or an object such as a k-wire or incision knife laid upon, the subject's body (e.g., back in the case of a planned dorsal tool insertion) as seen in a then-current optical image 110, the computer processor identifies such line, point or object (or applicable portion thereof) and indicates a corresponding lines or points overlaid on the 2D x-ray image 112. For some applications, a line or point is drawn on the subject's body (e.g., on the subject's back in the case of a planned dorsal tool insertion) using radiopaque ink.

Traditionally, in order to determine the location of an incision site, a rigid radiopaque wire (such as a K-wire) is placed on the subject's back at a series of locations, and the x-rays are taken of the wire at the locations, until the incision site is determined. Subsequently, a knife is placed at the determined incision site, and a final x-ray image is acquired for verification. By contrast, in accordance with the technique described herein, initially a single x-ray image may be acquired and bidirectionally mapped to the optical image. Subsequently the wire is placed at a location, and the corresponding location of the wire with respect to the x-ray image can be observed (using the bidirectional mapping) without requiring the acquisition of a new x-ray image. Similarly, when an incision knife is placed at a location, the corresponding location of an applicable portion of the knife (typically, its distal tip) with respect to the x-ray image can be observed (using the bidirectional mapping) without requiring the acquisition of a new x-ray image. Alternatively or additionally, a line can be drawn on the x-ray image (e.g., a vertical line that passes along the vertebral centers, anatomically along the spinous processes of the vertebrae) and the corresponding line can be observed in the optical image overlaid on the patient's back.

It should be noted however that for some applications, and in the absence of an optical camera image of the subject, the marker set that is visible both in the x-ray images and upon the subject's body serves as a joint reference for when identifying insertion points or incision sites by the surgeon. Typically, such identification is superior with respect to time, radiation, iterations, errors, etc., compared with current practices (such as in common non-CAS surgical settings) prior to the present invention.

For some applications, a surgeon places a radiopaque knife 116 (or another radiopaque tool or object) at a prospective incision site (and/or places a tool at a prospective tool insertion location) and verifies the location of the incision site (and/or tool insertion location) by observing the location of the tip of the knife (or portion of another tool) with respect to the x-ray (e.g., via cursor 117), by means of the bi-directional mapping between the optical image and the x-ray image. For some applications, the functionalities described hereinabove with reference to FIG. 10, and/or with reference other figures, are performed using markers (which are typically sterile), other than markers 52. For example, a radiopaque shaft 118, ruler, radiopaque notches, and/or radiopaque ink may be used.

Figure 11:
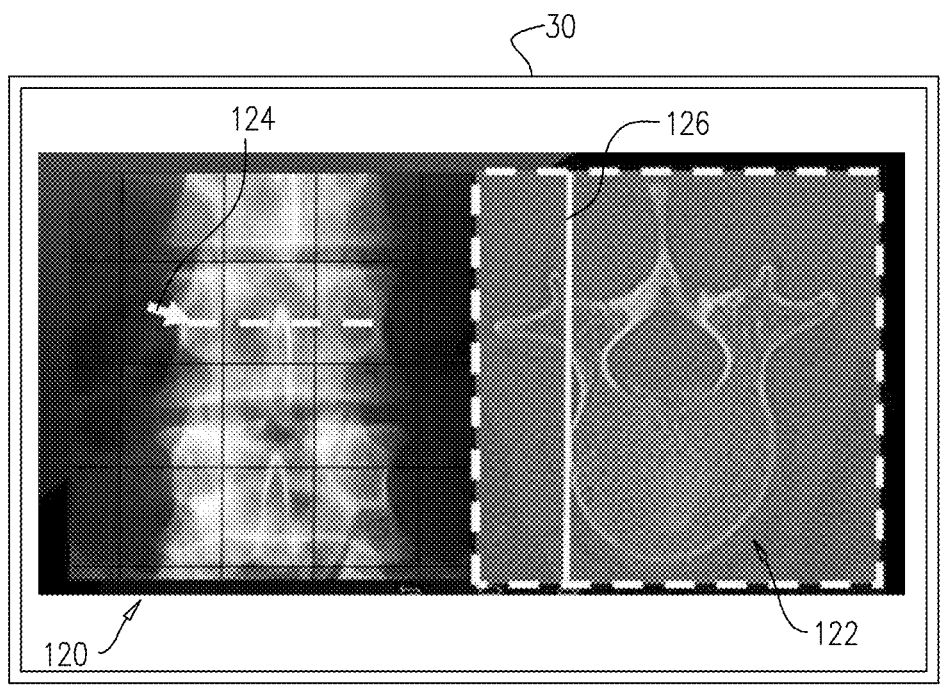
FIG. 11 shows an example of a 2D radiographic (e.g., x-ray) image displayed alongside a cross-sectional image of a subject's vertebra that is derived from 3D image data of the vertebra, in accordance with some applications of the present invention.

Reference is now made to FIG. 11, which shows an example of a 2D radiographic (e.g., x-ray) image 120 displayed alongside a cross-sectional image 122 of a subject's vertebra that is derived from a 3D image data of the vertebra, in accordance with some applications of the present invention. For some applications, even prior to registering the 2D images to the 3D image data (as described hereinbelow), the following steps are performed. X-ray image 120 of a given view the subject's spine (e.g., AP, as shown) is acquired. A point is indicated upon the image, e.g., the point indicated by cursor 124 in FIG. 11. Computer processor 22 of system automatically identifies the end plates of the vertebra and calculates the relative distance of indicated point from end plates. (It is noted that the computer processor typically does not calculate absolute distances in order to perform this function.) From the 3D (e.g., CT) image of the same vertebra, the computer processor generates and displays a cross-section of a given plane (which is typically axial) at the indicated location (e.g. image 122). For some applications, upon the cross-section, the computer processor drives the display to show a line 126 (e.g., a vertical line) within the cross-section, the line indicating that the indicated location falls somewhere along the line. For some applications, the line is drawn vertically upon an axial cross-section of the vertebra as shown. The computer processor determines where to place the line according to distance of the indicated point from left and right edges of the vertebra, and/or according to the position of the indicated point relative to visible features (e.g., spinous process, traverse processes, pedicles) in the x-ray image. Typically, the cross-sectional image with the line, and coupled with the surgeon's tactile feel of how far from the vertebra the skin is (and/or deriving such information from a 3D image), assists the surgeon in calculating the desired insertion angle of a tool.

Referring again to step 78 of FIG. 6, the first tool in the sequence of tools (which is typically a needle, e.g., a Jamshidi™ needle, for less invasive surgery, or a pedicle finder for more open surgery) is inserted into the subject (e.g., in the subject's back), and is slightly fixated in the vertebra. Subsequently, in step 80 of FIG. 6, two or more 2D radiographic images are acquired from respective views that typically differ by at least 10 degrees, e.g., at least 20 degrees, e.g., 30 degrees, and one of which is typically from the direction of insertion of the tool. Common combinations of such views include AP and left or right lateral, AP with left or right oblique, left oblique with left lateral, and right oblique with right lateral. It is noted that for some applications, 2D radiographic images of the tool and the vertebra are acquired from only a single x-ray image view.

Reference is now made to FIGS. 12A-J which are schematic illustrations and a flowchart of a method for determining a designated, e.g., planned, point 235 for skin-level or skeletal-portion-level incision/entry. For some applications, step 70 of FIG. 6 comprises not only marking targeted vertebra(e), but also planning the paths for tool insertion, including determining the intended site(s) of entering the patient's body with the tool, typically at skin-level or at a skeletal-portion-level, e.g., spine-level.

For some applications, the determination of intended incision/entry site, i.e., designated point 235, includes the following steps for each targeted vertebra, with each step either performed manually by the operator or automatically. (It is noted that some of the steps are optional, and that some of the steps may be performed in a different order to that listed below.)

Figures 13A, 13B:
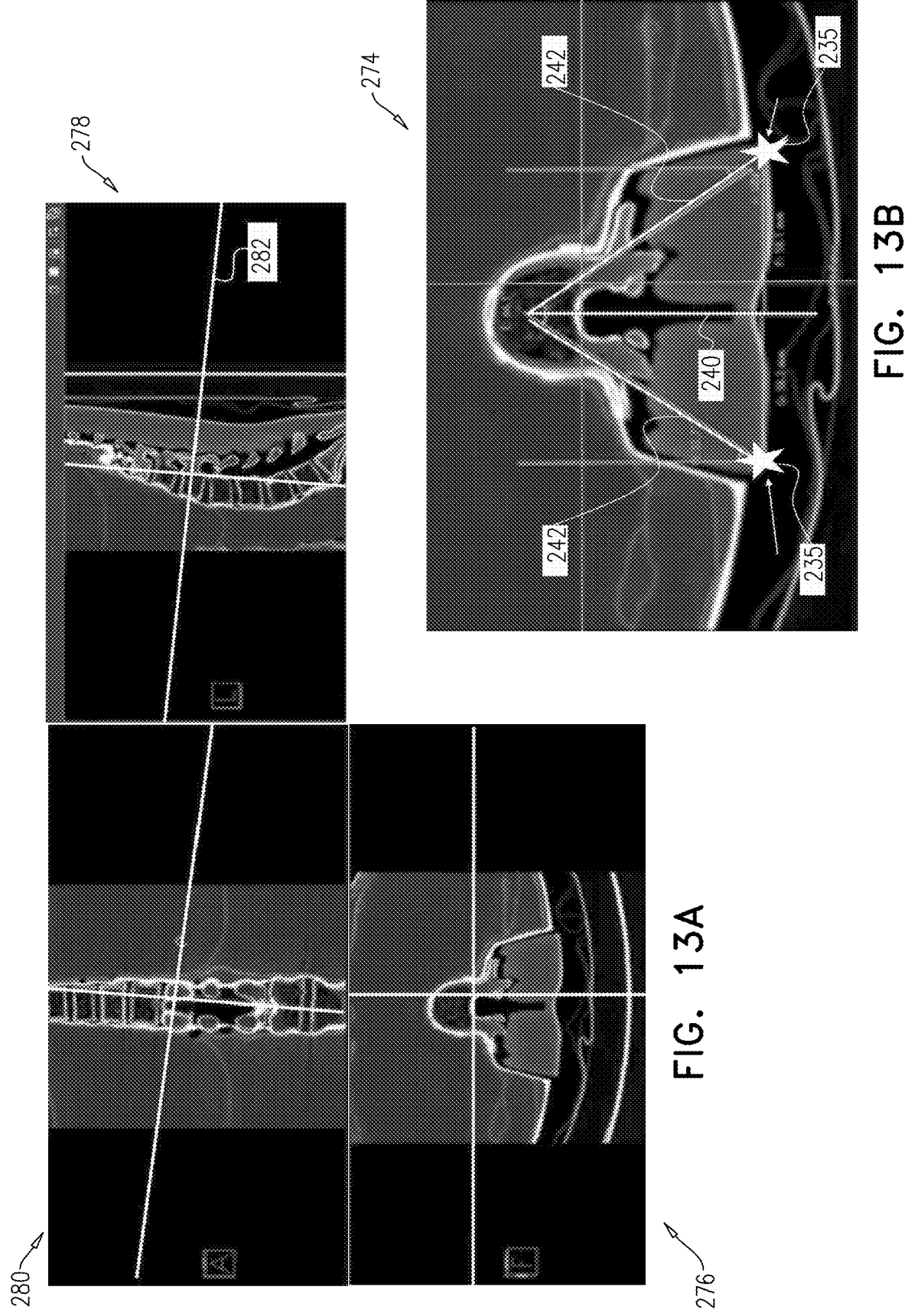
FIGS. 13A and 13B show an example of planning incision or tool insertion sites upon 3D scan data of a skeletal portion of the body, in accordance with some applications of the present invention.

1. For each targeted vertebra, 3D scan data of the vertebra is acquired and loaded (step 236 in FIG. 12B).
2. Scan data is displayed and viewed, typically at the coronal, sagittal and axial planes (such as is shown in FIG. 13A). Typically, the viewer software automatically ties (which can also be thought of as "links" or "associates") the three views to one another, such that manipulating the viewing in one plane effects corresponding changes in the views in the other planes. Optionally, a 3D reconstructed view is added.
3. The viewing planes are adjusted such that the vertebra is typically viewed in the axial view from a direction that is axial relative to the specific vertebra (as opposed to being axial to the longitudinal axis of the spine as a whole, since each vertebra may have its own angle relative to the longitudinal axis of the spine as a whole).
4. Vertebral axial cross-sections are leafed through.
5. An axial cross-section 238 most suitable for tool insertion is selected. In other words, an axial cross-section that would typically be the cross-section on which, during actual tool insertion, the longitudinal centerline of the tool would ideally reside, and thus where currently the planned approach vector would reside. For the planned insertion of pedicle screws, that would typically be an axial cross-section where the pedicles are relatively large and thus suitable for screw insertion, and further typically the largest for that vertebra. (In some cases, that may be a different cross section for each of the two pedicles of a same vertebra of the subject.) For some applications, the insertion plane for the specific vertebra, or pedicle within the vertebra, is selected in the sagittal view and then the axial view is auto-aligned with that direction.
6. Pedicle length and width are measured for later section of the specific tool or implant that will be used.
7. A generally-vertical line 240 is drawn upon such axial cross-section, through the spinous process and all the way to the skin. (Appropriate window-level values, such that the skin is visible, are typically used when viewing the image data.)
8. Diagonal tool-insertion lines 242 are drawn upon axial cross-section 238 through the pedicle, and typically both pedicles of the vertebra, from inside the vertebral body to skin level and potentially further beyond outside the subject's body. Intersection points 244 of such lines 242 with the skin are identified, i.e., at least one skin-level incision point or skeletal-portion-level entry point is designated within the body of the subject (step 250 in FIG. 12B). For some applications, intersection points 244 are identified at both sides of the vertebra. Alternatively, for some applications, only one diagonal tool-insertion line 242 is drawn upon axial cross-section 238, corresponding to one side of the vertebra, and one intersection point 244 of line 242 with the skin is identified.
9. (As noted previously, the two lines may reside on different planes and thus different cross-sections.) Typically, each line 242 begins at skin level and ends at the designated target within the vertebral body. Typically, each line 242 includes a skin-level starting point, and entry point into the pedicle, an exit point from the pedicle, or any combination thereof
10. Horizontal distances D1 and D2 of each of the intersection points to the vertical line marking the spinous process are measured and noted on the image.
11. Insertion angles (coronal, axial) for each tool-insertion line, at the skin-level intersection point, are measured and noted on the image.
12. Tool (and/or implant) representations are placed along one or more insertion lines in order to select optimal tool sizes (for example, the lengths and diameters of pedicle screws to be inserted).
13. The aforementioned intersection points, e.g., skin-level points (and potentially also the lines, angles and distances) are associated and stored with the 3D scan data for that vertebra (step 252 in FIG. 12B). The skin-level entry points or incision sites are typically stored as 3D coordinates within such 3D scan data.

For some applications and pursuant to the above, in step 76 of FIG. 6 the aforementioned 3D scan data for the vertebra, including the additional planning information and in particular the designated point(s) 235, i.e., skin-level incision site(s) or skeletal-portion-level, e.g., spin-level entry point(s), is registered with an x-ray image 246, typically from an AP view, that includes the same vertebra, using techniques such as DRRs that are further described in subsequent sections of this document. As a result, the designated point(s) 235, i.e., skin-level entry points or incision sites, are now displayed upon x-ray image 246. For some applications, using embodiments of the present invention as described above for step 76, one or more points 235' are subsequently auto-marked on a camera image 248 of the subject's back and displayed to the operator.

Figure 12A:
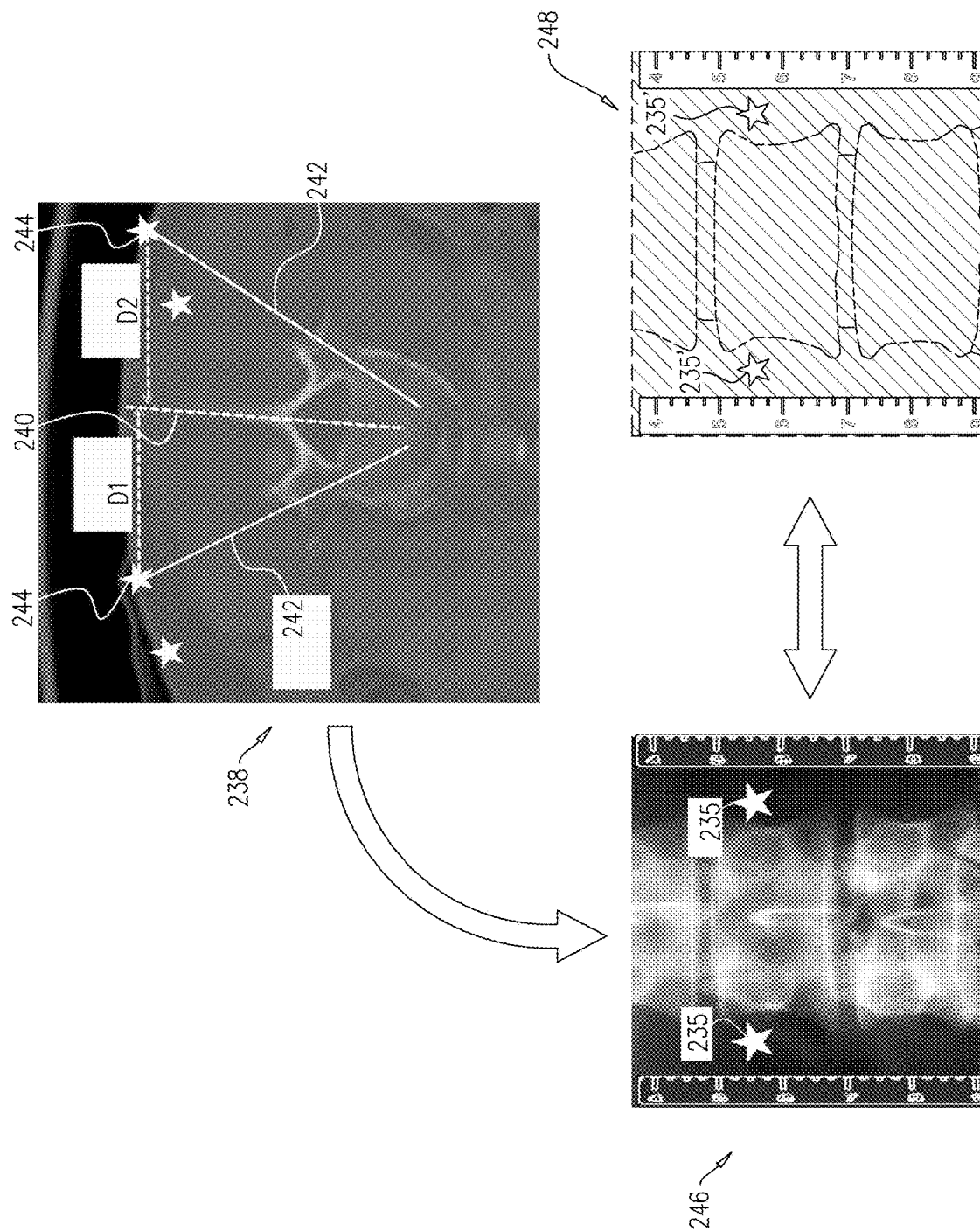
FIG. 12A shows an example of an identification upon the subject of a previously-planned skin-level incision point, in accordance with some applications of the present invention.
Figure 12B:
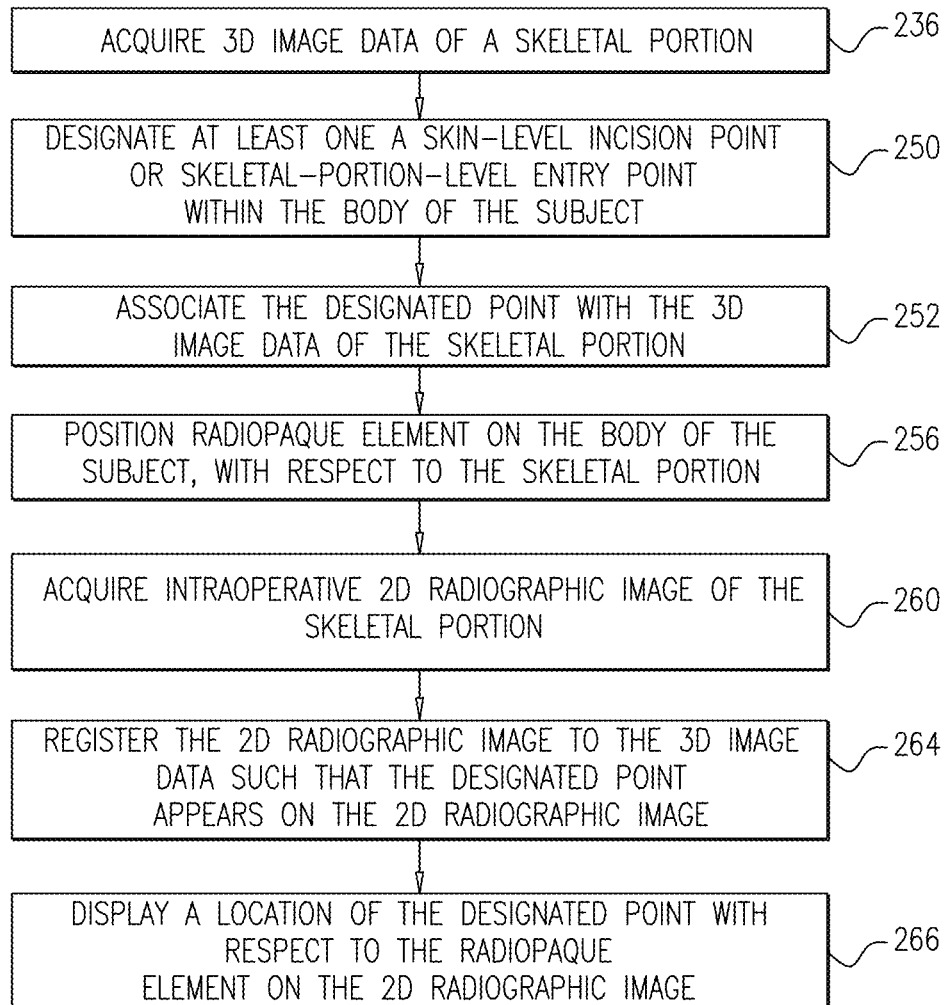
FIG. 12B is a flowchart of a method for determining a designated, e.g., planned, point for skin-level or skeletal-portion-level incision/entry, in accordance with some applications of the present invention.
Figure 12D:
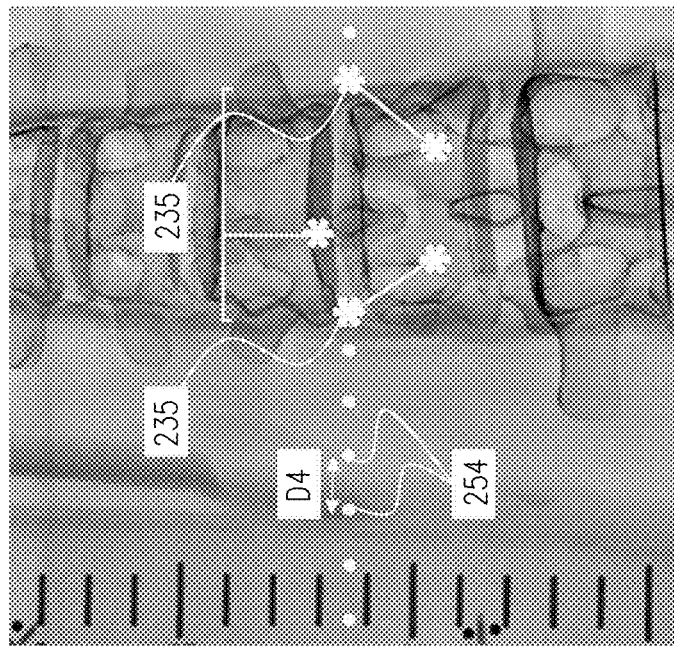
FIGS. 12C-12J show a method for determining a designated, e.g., planned, point for skin-level or skeletal-portion-level incision/entry, in accordance with some applications of the present invention.
Figure 12C:
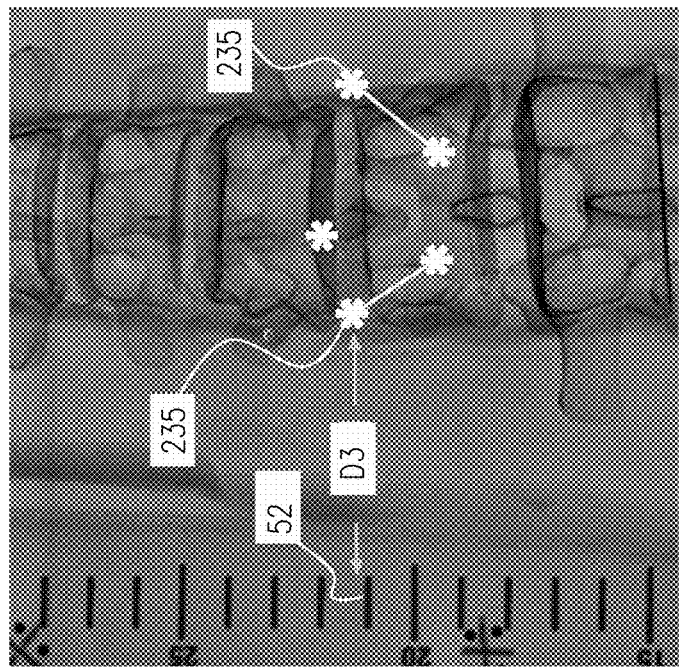

For some applications, such as is shown in FIG. 12C, a distance D3 of an incision site, e.g., designated point 235, from one or more (typically-nearest) elements, e.g., markers 52, of the marker set 50 is measured, manually or automatically, and is measured and displayed on the x-ray image to facilitate physical determination of the incision site (for example, the incision site may be 6 cm horizontally to the right from marker number 21 on the left ruler-like marker set). For some applications, such as is shown in FIG. 12D, distance D3 is displayed not numerically but by markings 254 (e.g., notches) that are overlaid on the x-ray image and are spaced at known intervals D4, for example 1 cm, from one another.

For some applications, a camera image is not available, and the operator estimates, or measures physically, the locations of points 235' on the subject's back relative to the marker set that is (a) placed on the subject's back and (b) also visible in the x-ray image. For some applications, based on the location of the designated point with respect to the radiopaque element on the 2D radiographic image, the operator labels a location of the designated point on the subject's body.

Figure 12E:
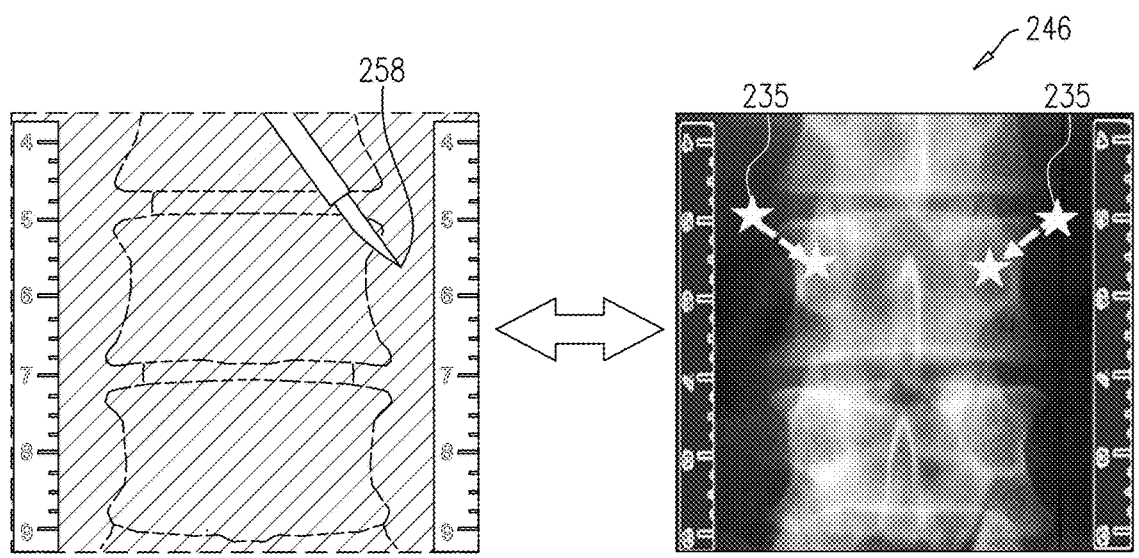
Figure 12F:
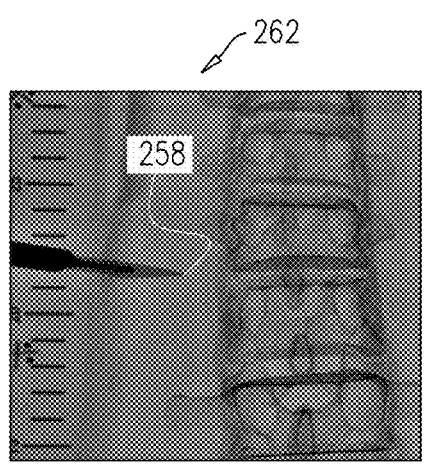
Figure 12G:
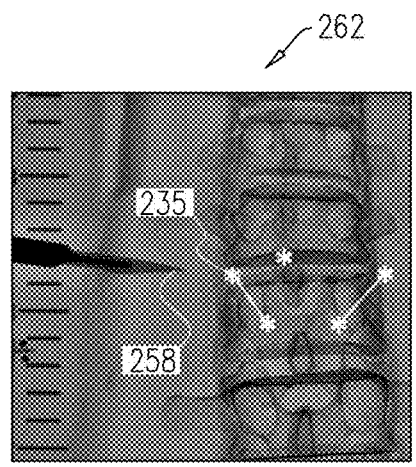
Figure 12H:
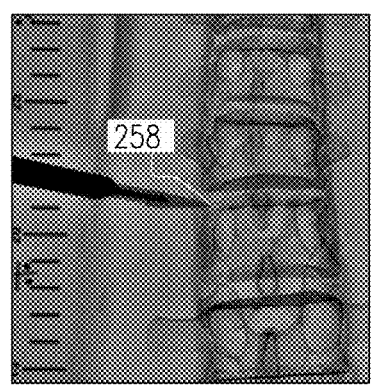
Figure 12I:
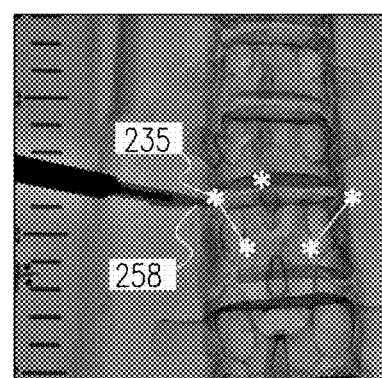

For some applications, such as is shown in FIG. 12E, visual identification of previously-planned skin-level incision sites, as well as the desired direction of insertion towards each corresponding vertebral entry point upon the subject, may be performed with no measurements from the aforementioned planning provided upon the x-ray image. In step 256 of FIG. 12B the operator places a radiopaque element 258, such as the tip of a radiopaque tool, such as an incision knife, at the estimated location of point 235' on the subject's back (using point(s) 235 in x-ray image 246 as a guide). In step 260 of FIG. 12B, the operator acquires an intraoperative x-ray image 262 (FIG. 12F), typically the same AP as before. In step 264 the intraoperative x-ray image 262 is registered to the 3D image data such that the prior 3D planning data is auto-registered to x-ray image 262 (FIG. 12G) and both point(s) 235 and radiopaque element 258, e.g., the knife's tip, are thus displayed in second x-ray image 262 (step 266). The operator can now tell whether the knife is placed correctly, or whether another iteration is required. FIGS. 12H-I show a second iteration after the operator has moved radiopaque element 258, e.g., the knife's tip, closer to point 235.

Figure 12J:
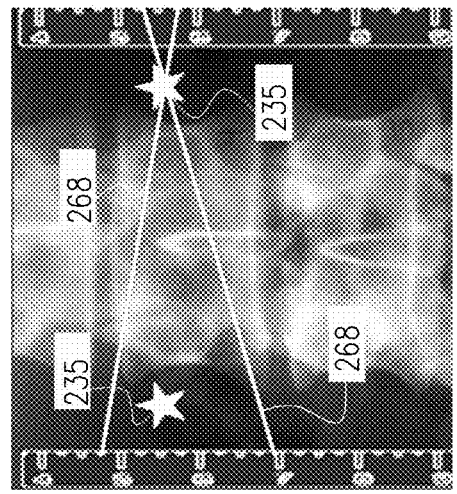
Figure 12J:
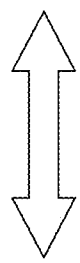
Figure 12J:
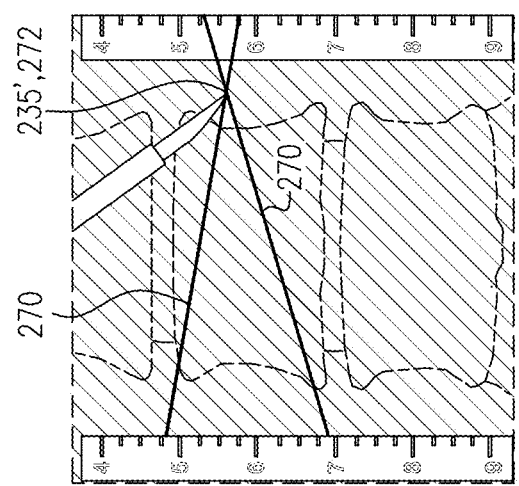

For some applications, such as is shown in FIG. 12J, in the absence of a current optical camera image of the subject, any of points 235 is further indicated upon the registered x-ray image as an intersection of two virtual lines 268 drawn relative to corresponding portions of the market set. For some applications, the lines are generated automatically. For some applications, the lines are drawn manually by the operator. Using marker sets 50 as a reference, the operator can now replicate the two virtual lines by laying long objects 270 (e.g., K-wires, rulers, etc.) on the subject and marking the point 272 of intersection. Consequently, the intersection of the K-wires indicates the planned skin-level insertion point 235' on the subject.

Figure 12K:
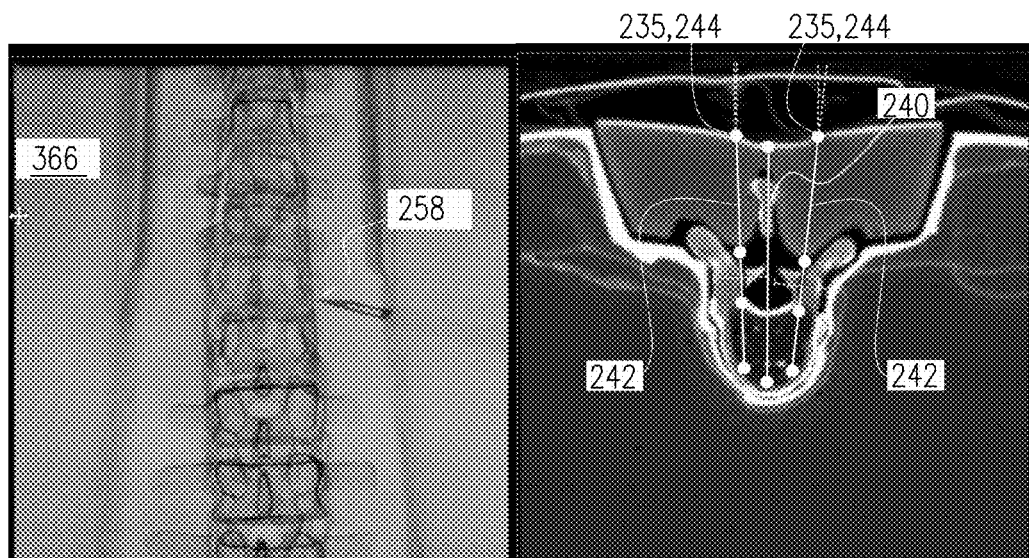
FIGS. 12K-P show a method for determining a designated, e.g., planned, point for skin-level or skeletal-portion-level incision/entry, in accordance with some applications of the present invention.
Figure 12L:
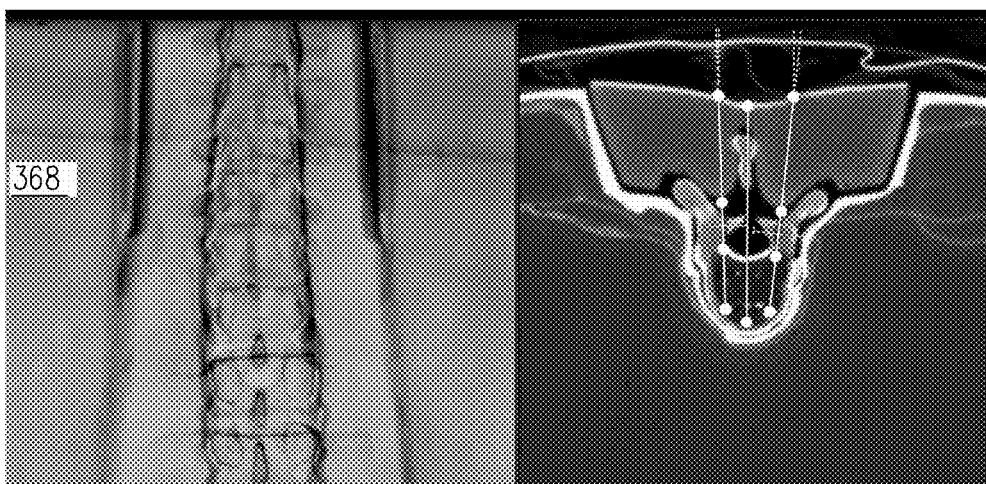
Figure 12M:
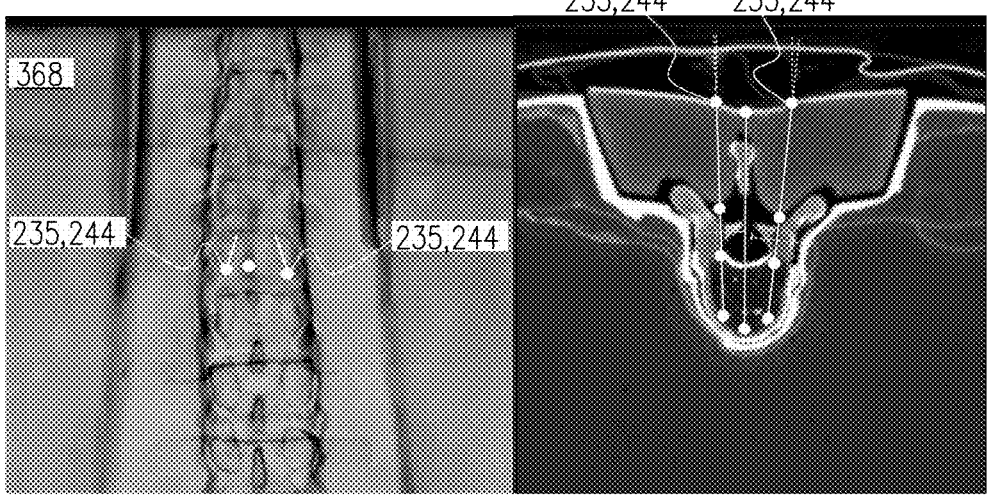

Reference is now made to FIGS. 12K-P, which depict a method for identification of an incision site with respect to radiopaque element 258, in accordance with some applications of the present invention. For some applications, a first x-ray image 366 is acquired after positioning radiopaque element 258, e.g., the tip of a radiopaque tool, at an estimated location on the subject's back (FIG. 12K). On the left side of FIG. 12K, 3D image data for the target vertebra is displayed along with the 3D planning data containing generally-vertical line 240, diagonal tool-insertion line(s) 242, and intersection point(s) 244 corresponding to designated point(s) 235 which correspond to the incision site(s). FIG. 12L shows a DRR 368, generated from the 3D image data, that matches x-ray image 366. The same planning data as shown in FIG. 12K is shown again side-by-side with DRR 368 in FIG. 12L. The planning data is then associated with, e.g., projected onto, DRR 368. For some applications, such as is shown in FIG. 12M, the planning data including intersection point(s) 244 corresponding to designated point(s) 235 may be displayed on DRR 368. Alternatively, the association between the planning data and DRR 368 is maintained within computer processor 22.

Figure 12N:
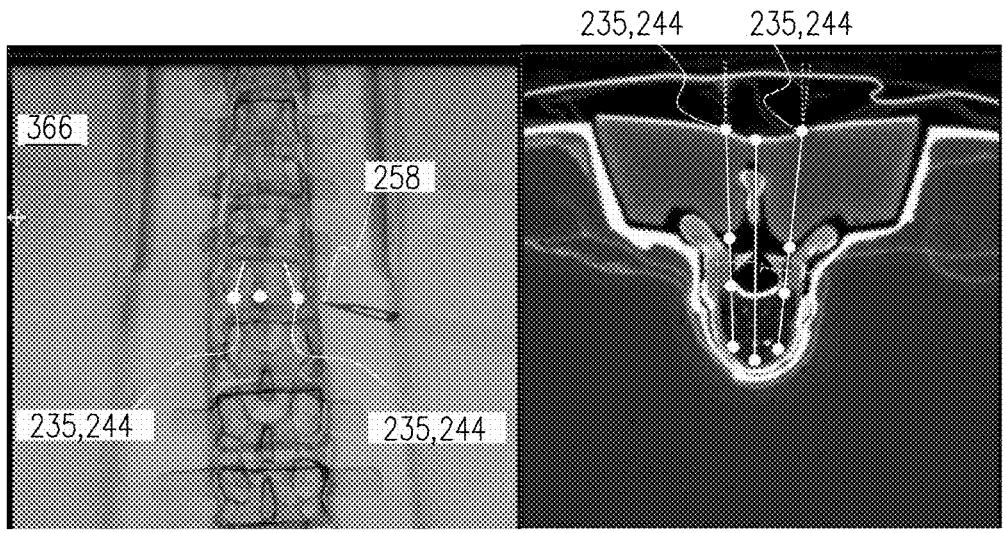
Figure 12O:
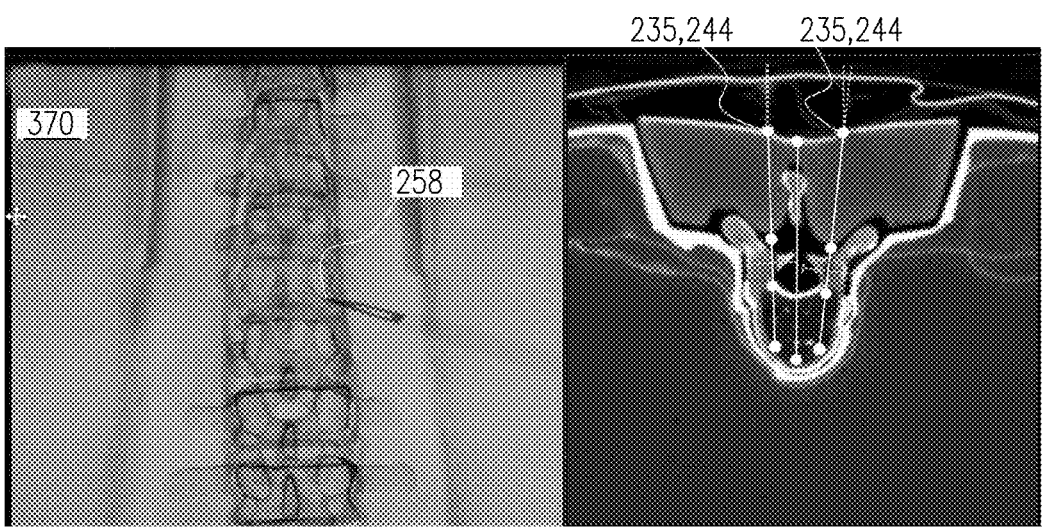
Figure 12P:
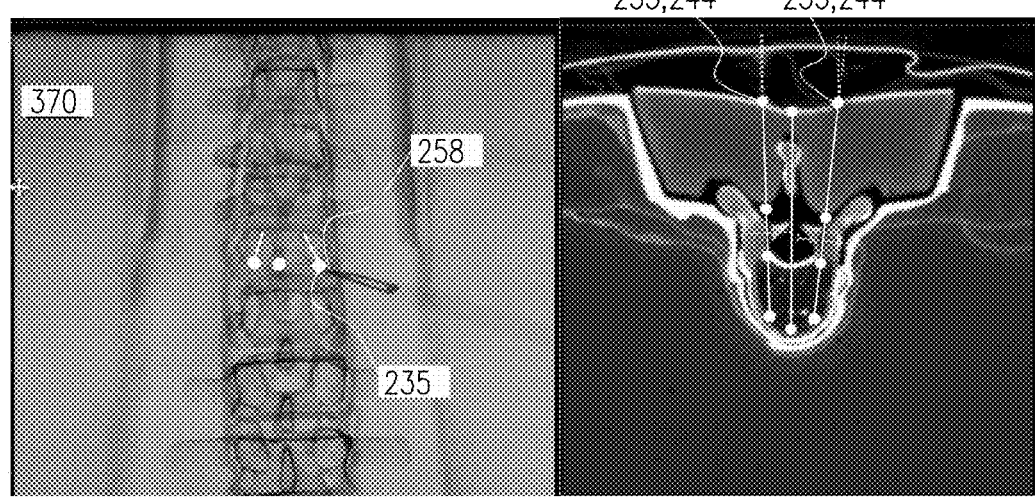

FIG. 12N shows the planning data now projected onto x-ray image 366 (x-ray image 366 matching DRR 368), such that the planning data including intersection point(s) 244 corresponding to designated point(s) 235 is now visible relative to radiopaque element 258, e.g., the tip of the radiopaque tool. If radiopaque element 258 is not in the correct position, as is the case shown in FIG. 12N, radiopaque element 258 is moved and a second x-ray image 370 acquired. FIG. 12O shows the second x-ray image 370 side-by-side with the planning data. As shown in FIG. 12P, the planning data is then projected onto second x-ray image 370 using the same steps as described with reference to FIGS. 12L-N. Radiopaque element 258, such as the tip of the operating tool, can now be seen on target at designated point 235.

Reference is now made to FIGS. 13A-B, which show an example of planning tool insertion sites at skin level, as described hereinabove, upon the 3D scan data, in accordance with embodiments of the present invention. FIG. 13A depicts generation and selection of an appropriate vertebral cross section 274 (FIG. 13B) that meets the aforementioned criteria, from the 3D scan data of a spine phantom with such data viewed in all three planes as described above (axial view 276, coronal view 278, and sagittal view 280). For example, it should be noted that the line 282 in the sagittal view indicates the vertebra is sliced axially in an axial direction that is relative to the targeted vertebra itself (as opposed to being axial to the longitudinal axis of the spine as a whole). FIG. 13B depicts generally vertical spinous-process line 240, two diagonal insertion lines 242, and two skin-level insertion points 235, all generated in accordance with embodiments of the present invention as described above with reference to FIG. 12A.

It should be noted that embodiments described hereinbelow are also useful for identifying the insertion point into a vertebra in the case of more-invasive or open surgery, wherein the applicable portion of a vertebra is visible via an incision, or exposed. For some applications, such determination of insertion points is performed according to the following steps for each targeted vertebra, with each step performed manually by the operator or automatically. (It is noted that some of the steps are optional, and that some of the steps may be performed in a different order to that listed below.)

1. For each targeted vertebra, 3D scan data of the vertebra is loaded.
2. Scan data is displayed and viewed, typically at the coronal, sagittal and axial planes. Typically, the viewer software automatically ties the three views to one another, such that manipulating the viewing in one plane effects corresponding changes in the views in the other planes. Optionally, a 3D reconstructed view is added.

3. The viewing planes are adjusted such that the vertebra is typically viewed in the axial view from an axial direction that is relative to the specific vertebra (as opposed to being axial to the longitudinal axis of the spine as a whole, since each vertebra has its own typical angle relative to the longitudinal axis of the spine as a whole).
4. Vertebral axial cross-sections are leafed through.
5. An axial cross-section most suitable for tool insertion is selected. In other words, that would typically be the cross-section on which, during actual tool insertion, the longitudinal center line of the tool would ideally reside, and where the currently planned approach vector would reside. For the planned insertion of pedicle screws, that would typically be an axial cross-section where the pedicles are relatively large and thus suitable for screw insertion, and further typically the largest for that vertebra. (In some cases, that may be a different cross section for each of the two pedicles of the vertebra within the subject.)
6. A generally-vertical line is drawn upon such axial cross-section, through the spinous process and all the way to the skin (Appropriate window-level values, such that the skin is visible, are used.)
7. Diagonal tool-insertion lines are drawn upon such axial cross-section through the pedicle, and typically both pedicles of the vertebra, from inside the vertebral body to the applicable boarder of the vertebra and potentially further beyond outside the subject's body. Intersection points of such lines with the skin, typically at both sides of the vertebra, are identified.
8. Horizontal distances of each of the intersection points to the vertical line marking the spinous process are measured and noted on the image.
9. Insertion angles (coronal, axial) for each tool-insertion line, at the vertebral-border intersection point, are measured and noted on the image.
10. Tool representations are placed along one or more insertion lines in order to select optimal tool sizes (for example, the lengths and diameters of pedicle screws to be inserted).
11. The aforementioned entry points (and potentially also angles, lines, distances) are associated and stored with the 3D scan data for that vertebra. The skin-level entry points or incision sites are typically stored as 3D coordinates within such 3D scan data.

Such steps may be followed by any of the embodiments previously described for skin-level insertion, by which the entry points from the 3D data set are registered to the applicable x-ray image, displayed upon that x-ray image, and used for determining point(s) of entry into the vertebra during surgery.

For some applications, both the incision sites at the skin level, and the entry points into the vertebra at the vertebra's applicable edge, are calculated in the 3D data, then registered to, and displayed upon, the 2D x-ray image, and then used for determining the skin-level incision site and the direction of tool entry through that site, typically in accordance with techniques described hereinabove. For some applications, the distance of the incision site from one or more (typically-nearest) elements of the marker set is measured manually or automatically and displayed to facilitate physical determination of the incision site and/or entry point.

For some applications, planning in its various forms as described hereinabove also comprises marking an out-of-pedicle point along the planned insertion path. An out-of-pedicle point is at or near a location along the planned path where the object being inserted along the path exits the pedicle and enters the vertebral body.

For some applications, one or more of the following points are marked along the planned insertion path: incision at skin level, entry into the vertebra, out-of-pedicle, target, or any other point.

Figure 14A:
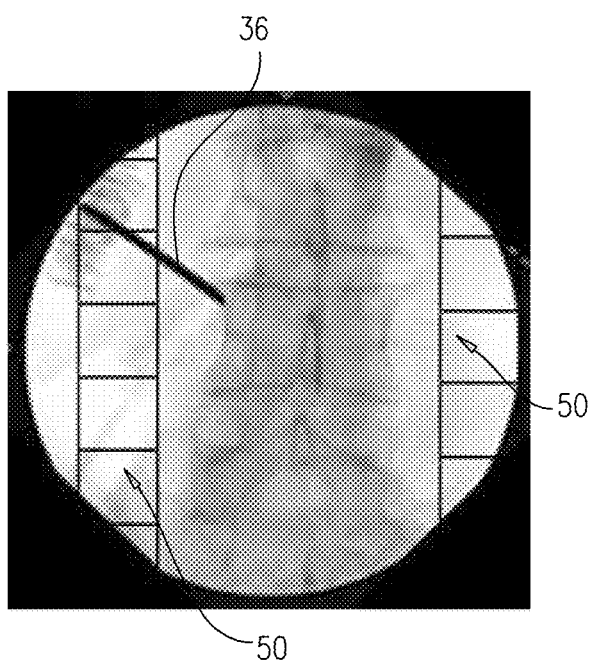
FIGS. 14A and 14B show examples of respectively AP and lateral x-ray images of a Jamshidi™ needle being inserted into a subject's spine, in accordance with some applications of the present invention.
Figure 14B:
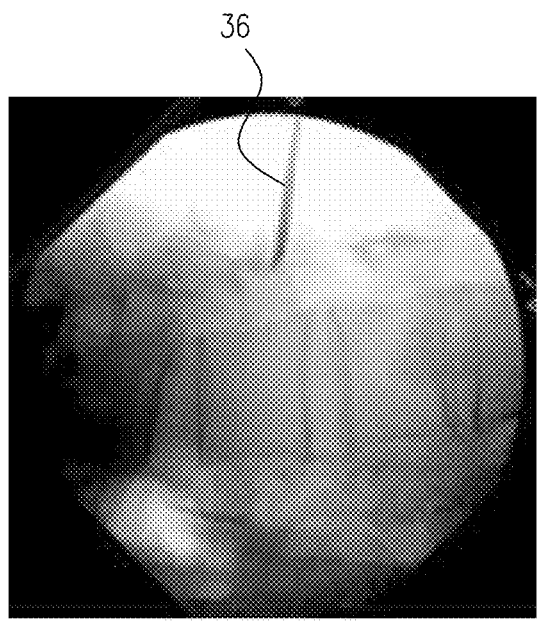

Reference is now made to FIGS. 14A and 14B, which show examples of respectively AP and lateral x-ray images of an elongated tool (such as a Jamshidi™ needle) 36 being inserted into a subject's spine, in accordance with some applications of the present invention. As shown, sets 50 of markers 52 typically appear at least in the AP image.

Figure 15A:
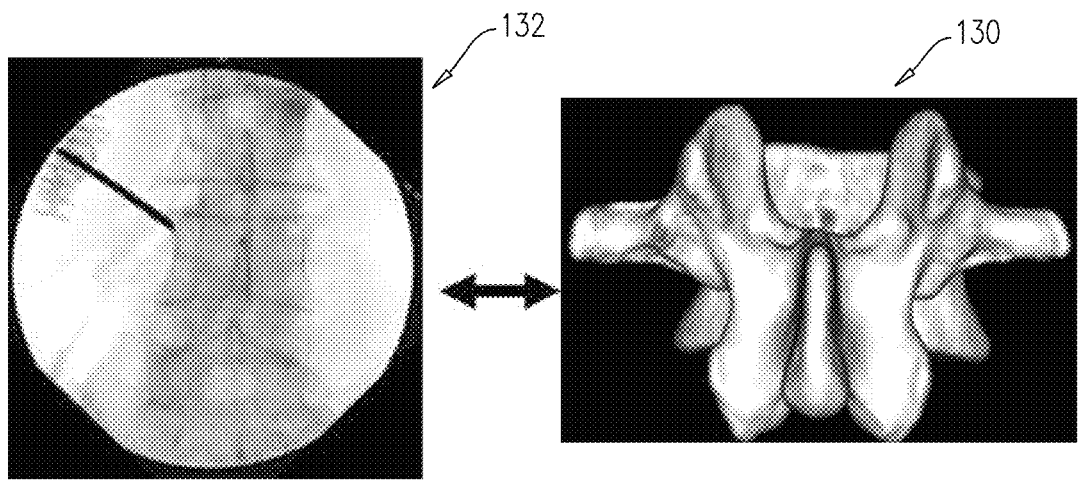
FIGS. 15A and 15B show examples of correspondence between respective views of a 3D image of a vertebra, with corresponding respective first and second x-ray images of the vertebra, in accordance with some applications of the present invention.
Figure 15B:
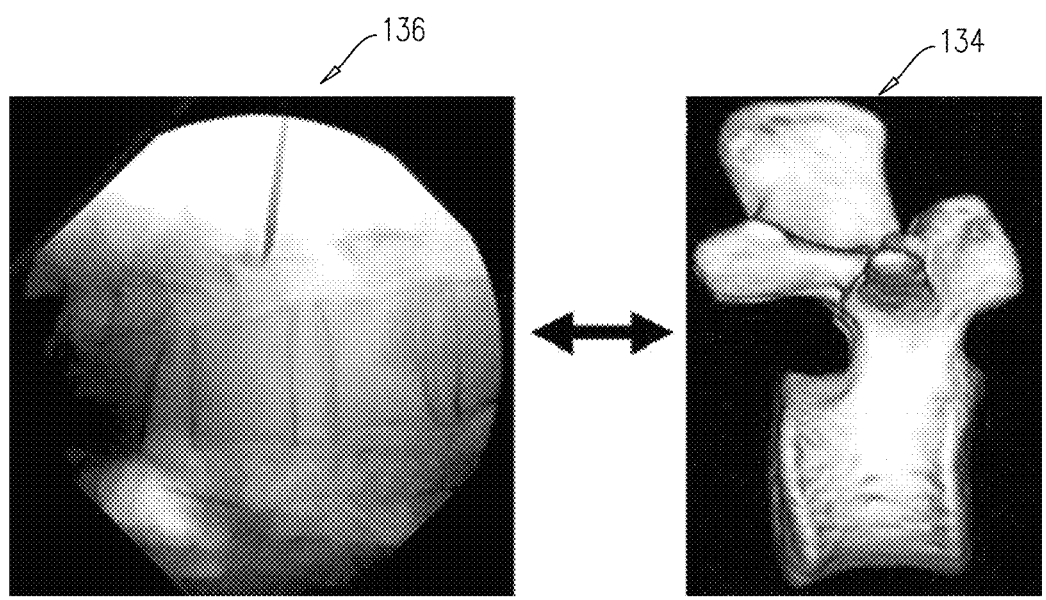

Reference is now made to FIGS. 15A and 15B, which show examples of correspondence between views of a 3D image of a vertebra, with, respectively, first and second 2D x-ray images 132 and 136 of the vertebra, in accordance with some applications of the present invention. In FIG. 15A the correspondence between a first view 130 of a 3D image of a vertebra with an AP x-ray image of the vertebra is shown, and in FIG. 15B the correspondence between a second view 134 of a 3D image of a vertebra with a lateral x-ray image of the vertebra is shown.

Figure 16:
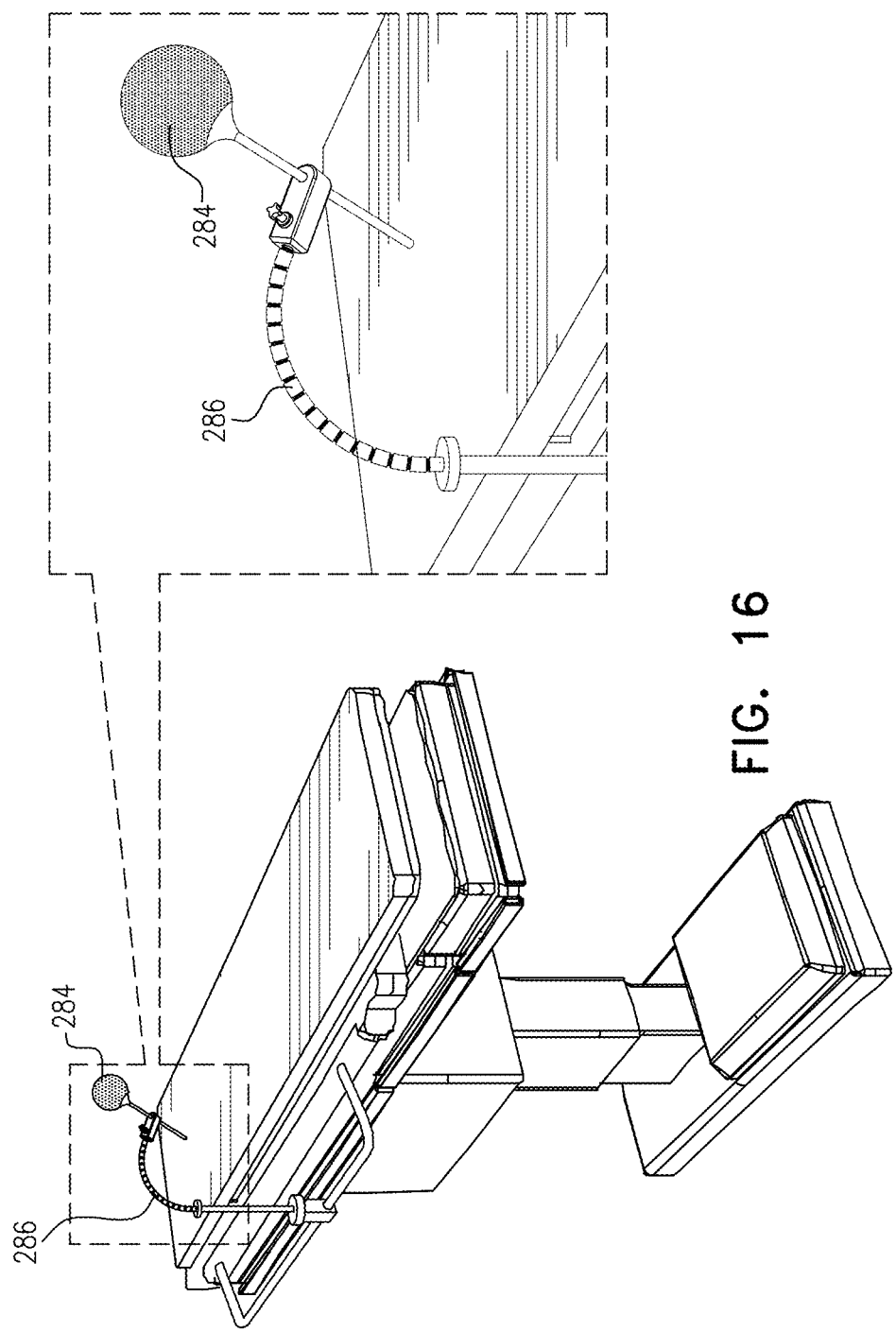
FIG. 16 is a schematic illustration showing tool gripped by an adjustable tool holder, with the tool holder fixed to the rail of a surgical table, in accordance with some applications of the present invention.

Reference is made to FIG. 16, which shows an example of a surgical tool 284 gripped by an adjustable tool holder 286, with the tool holder fixed to the rail of a surgical table. For some applications, subsequent to the fixation of the tool in the subject's vertebra, the 3D image data and 2D images are registered to each other, in accordance with step 82 of FIG. 6. For some applications, tool 284 is not fixated into the vertebra, but rather it is positioned relative to the vertebra. An example for a tool fixated in a vertebra is a needle inserted into a vertebra in a less-invasive surgery performed through a small incision, while an example for a tool 284 positioned relative to a vertebra but not inserted yet would be a pedicle finder aimed relative to the vertebra in the course of a more invasive surgery performed through a large incision. For some applications, tool 284 is attached to tool holder 286 that can maintain tool 284 in a consistent position during the acquisition of one or more x-ray images. For some applications, such holder 286 is attached to the surgical table, or to a separate stand, or to a robotic arm, or any combination thereof.

For some applications, holder 286 to which the tool is attached also comprises one or more angle gauges, typically digital. In such cases, the aforementioned insertion angles previously measured in the planning phase may be applied when aiming the tool at the vertebra. For some applications, application of the angles is manual by the operator of the holder. For some applications, and when holder 286 is robotic, application of the angles is automated and mechanized. For some applications, it is assumed that the applicable portion of the subject is positioned completely horizontally.

However, it is noted that the registration of the 3D image data and the 2D images to each other may be performed even in the absence of a tool within the images, in accordance with the techniques described hereinbelow.

For some applications and when a tool is present in the 2D images but not present in the 3D images, the visibility of a tool or a portion thereof is reduced (or eliminated altogether) by means of image processing from the 2D images prior to their registration with the 3D image data. After registration is completed, 2D images with the tool present, i.e., as prior to the aforementioned reduction or elimination, are added to (utilizing the then-known registration parameters), or replace, the post-reduction or elimination 2D images, within the registered 2D-3D data, according to the registration already achieved with the post-reduction or elimination 2D images. For some applications, regions in the 2D image comprising a tool or a marker set are excluded when registering the 2D images with the 3D data. For some applications, the aforementioned techniques facilitate registration of the 2D images with the 3D data set because all include at the time of their registration to one another only (or mostly) the subject's anatomy, which is typically the same, and thus their matches to one another need not (or to a lesser extent) account for elements that are included in the 2D images but are absent from the 3D data set. For some applications, the reduction or elimination of the visibility of the tool or a portion thereof is performed using techniques and algorithmic steps as described in US Patent Application 2015-0282889 to Cohen (and Tolkowsky), which is incorporated herein by reference. The same applies to a reduction of elimination of the visibility of previously-placed tools, such as implants (e.g., pedicle screws, rods, cages, etc.), in any of the images, such as prior to image registration.

Typically, the 3D image data and 2D images are registered to each other by generating a plurality of 2D projections from the 3D image data and identifying respective first and second 2D projections that match the first and second 2D x-ray images of the vertebra, as described in further detail hereinbelow. (For some applications, 2D x-ray images from more than two 2D x-ray image views are acquired and the 3D image data and 2D x-ray images are registered to each other by identifying a corresponding number of 2D projections of the 3D image data that match respective 2D x-ray images.) Typically, the first and second 2D x-ray images of the vertebra are acquired using an x-ray imaging device that is unregistered with respect to the subject's body, by (a) acquiring a first 2D x-ray image of the vertebra (and at least a portion of the tool) from a first view, while the x-ray imaging device is disposed at a first pose with respect to the subject's body, (b) moving the x-ray imaging device to a second pose with respect to the subject's body, and (c) while the x-ray imaging device is at the second pose, acquiring a second 2D x-ray image of at least the portion of the tool and the skeletal portion from a second view.

For some applications, the 3D imaging that is used is CT imaging, and the following explanation of the registration of the 3D image data to the 2D images will focus on CT images. However, the scope of the present invention includes applying the techniques describe herein to other 3D imaging modalities, such as MRI and 3D x-ray, mutatis mutandis.

X-ray imaging and CT imaging both apply ionizing radiation to image an object such as a body portion or organ. 2D x-ray imaging generates a projection image of the imaged object, while a CT scan makes use of computer-processed combinations of many x-ray images taken from different angles to produce cross-sectional images (virtual "slices") of the scanned object, allowing the user to see inside the object without cutting. Digital geometry is used to generate a 3D image of the inside of the object from a large series of 2D images.

Figure 17A:
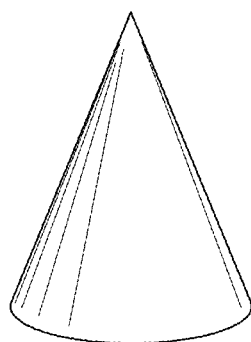
FIGS. 17A, 17B, and 17C are schematic illustrations that demonstrate the relationship between a 3D image of an object (FIG. 17A) and side-to-side (FIG. 17B) and bottom-to-top (FIG. 17C) 2D projection images of the object, such a relationship being utilized, in accordance with some applications of the present invention.
Figure 17B:
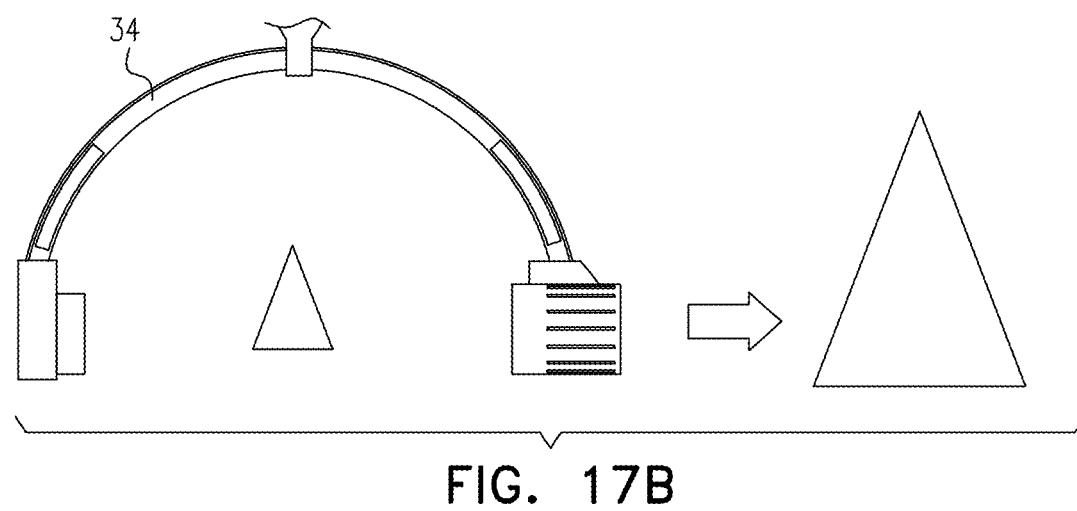
Figure 17C:
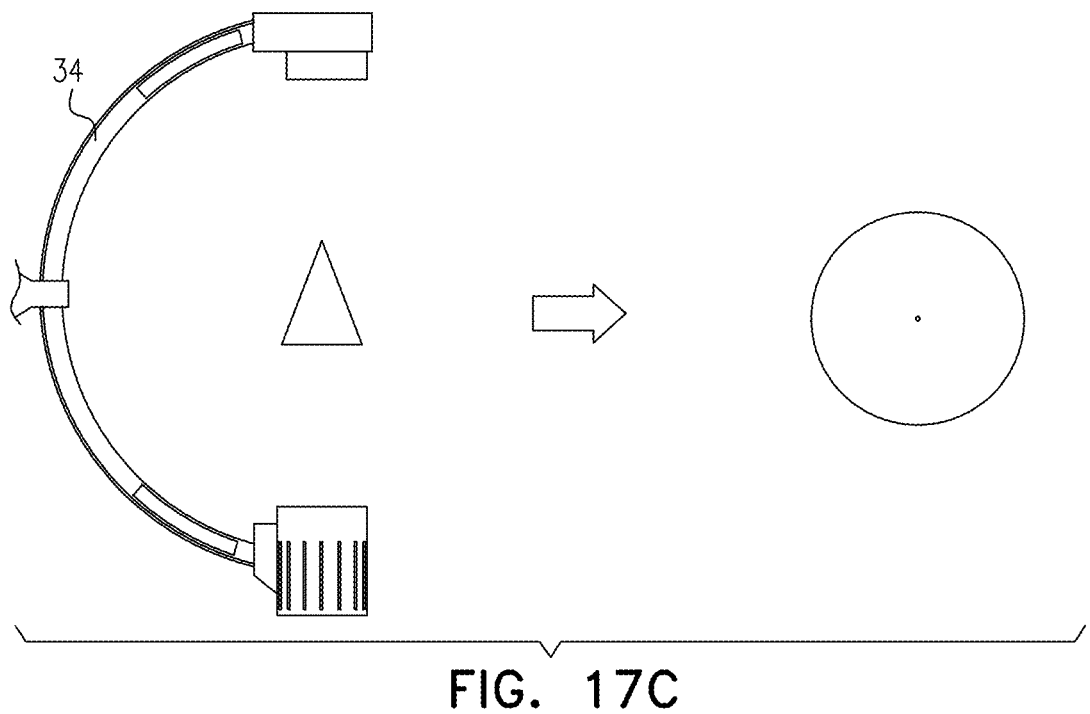

Reference is now made to FIGS. 17A, 17B, and 17C, which demonstrate the relationship between a 3D image of an object (which in the example shown in FIG. 17A is a cone) and side-to-side (FIG. 17B) and bottom-to-top (FIG. 17C) 2D images of the object, such relationship being utilized, in accordance with some applications of the present invention. As shown, for the example of the cone, the bottom-to-top 2D image (which is analogous to an AP x-ray image of an object acquired by C-arm 34, as schematically indicated in FIG. 17C) is a circle, while the side-to-side image (which is analogous to a lateral x-ray image of an object, acquired by C-arm 34, as schematically indicated in FIG. 17C) is a triangle. It follows that, in the example shown, if the circle and the triangle can be registered in 3D space to the cone, then they also become registered to one another in that 3D space. Therefore, for some applications, 2D x-ray images of a vertebra from respective views are registered to one another and to 3D image data of the vertebra by generating a plurality of 2D projections from the 3D image data, and identifying respective first and second 2D projections that match the 2D x-ray images of the vertebra.

In the case of 3D CT images, the derived 2D projections are known as Digitally Reconstructed Radiographs (DRRs). If one considers 3D CT data and a 2D x-ray image of the same vertebra, then a simulated x-ray camera position (i.e., viewing angle and viewing distance) can be virtually positioned anywhere in space relative to a 3D image of the vertebra, and the corresponding DRR that this simulated camera view would generate can be determined. At a given simulated x-ray camera position relative to the 3D image of the vertebra, the corresponding DRR that this simulated camera view would generate is the same as the 2D x-ray image. For the purposes of the present application, such a DRR is said to match an x-ray image of the vertebra. Typically, 2D x-ray images of a vertebra from respective views are registered to one another and to 3D image data of the vertebra by generating a plurality of DRRs from 3D CT image data, and identifying respective first and second DRRs (i.e., 2D projections) that match the 2D x-ray images of the vertebra. By identifying respective DRRs that match two or more x-ray images acquired from respective views, the x-ray images are registered to the 3D image data, and, in turn, the x-ray images are registered to one another via their registration to the 3D image data.

For some applications, and due to the summative nature of x-ray imaging, an x-ray image of a given vertebra may also, depending on the x-ray view, comprise elements from a neighboring vertebra. In such case, those elements may be accounted for (by way of elimination or inclusion) during the act of 2D-3D registration, and in accordance with embodiments of the present invention. For some applications, such accounting for is facilitated by 3D segmentation and reconstruction of the given (targeted) vertebra that is the focus of the then-current registration process.

For some applications, x-ray images are enhanced using the corresponding DRRs from the 3D data set. For some applications, newly-acquired x-ray images are enhanced by corresponding DRRs that were generated prior to that in the act of registering previously-acquired x-ray images to the same 3D data set. For some applications, the newly-acquired and the previously-acquired x-ray images are acquired from the same poses of the x-ray c-arm relative to the subject. For some applications, the newly-acquired and the previously-acquired x-ray images are combined with one another for the purpose of image enhancement.

For some applications, in order to register the 2D images to the 3D image data, additional registration techniques are used in combination with the techniques described herein. For example, intensity based methods, feature based methods, similarity measures, transformations, spatial domains, frequency domains, etc., may be used to perform the registration.

For some applications, and wherein the 3D image set was acquired in the operating room, the 3D image set also comprises applicable portions of marker set(s) 50, such that the marker set serves as an additional one-or-more registration fiducial in between the 2D images and the 3D data set.

Typically, by registering the x-ray images to the 3D image data using the above-described technique, the 3D image data and 2D x-ray images are brought into a common reference frame to which they are all aligned and scaled. It is noted that the registration does not require tracking the subject's body or a portion thereof (e.g., by fixing one or more location sensors, such as an IR light, an IR reflector, an optical sensor, or a magnetic or electromagnetic sensor, to the body or body portion, and tracking the location sensors).

Typically, between preprocedural 3D imaging (e.g., 3D imaging performed prior to entering the operating room, or prior to performing a given intervention) and intraprocedural 2D imaging, the position and/or orientation of a vertebra relative to the subject's body and to neighboring vertebrae is likely to change. For example, this may be due to the patient lying on his/her back in preprocedural imaging but on the stomach or on the side for intraprocedural imaging, or the patient's back being straight in preprocedural imaging, but being folded (e.g., on a Wilson frame) in intraprocedural imaging. In addition, in some cases, due to anesthesia the position of the spine changes (e.g. sinks), and once tools are inserted into a vertebra, that may also change its positioning relative to neighboring vertebrae. However, since a vertebra is a piece of bone, its shape typically does not change between the preprocedural 3D imaging and the intraprocedural 2D imaging. Therefore, registration of the 3D image data to the 2D images is typically performed with respect to individual vertebrae. For some applications, registration of the 3D image data to the 2D images is performed on a per-vertebra basis even in cases in which segmentation of a vertebra in the 3D image data leaves some elements, such as portions of the spinous processes of neighboring vertebrae, within the segmented image of the vertebra. In addition, for some applications, registration of the 3D image data to the 2D images is performed with respect to a spinal segment comprising several vertebrae. For example, registration of 3D image data to the 2D images may be performed with respect to a spinal segment in cases in which the 3D image data were acquired when the subject was already in the operating room and positioned upon the surgical table for the intervention.

As described hereinabove, typically, during a planning stage, an operator indicates a target vertebra within the 3D image data of the spine or a portion thereof (e.g., as described hereinabove with reference to FIG. 8A). For some applications, the computer processor automatically identifies the target vertebra in the x-ray images, by means of image processing, e.g., using the techniques described hereinabove. For some applications, the registration of the 3D image data to the 2D images is performed with respect to an individual vertebra that is automatically identified, by the computer processor, as corresponding to a target vertebra as indicated by the operator with respect to the 3D image data of the spine or a portion thereof (e.g., as described hereinabove with reference to FIGS. 8B-C).

Typically, and since the registration is performed with respect to an individual vertebra, the registration is not affected by motion of the vertebra that occurs between the acquisition of the two x-ray images (e.g., due to movement of the subject upon the surgical table, motion due to respiration, etc.), since both motion of the C-arm and of the vertebra may be assumed to be rigid transformations (and thus, if both motions occur in between the acquisition of the two x-ray images, a chaining of two rigid transformations may be assumed).

As described hereinabove, typically, 2D x-ray images of a vertebra from respective views are registered to one another and to a 3D image data of the vertebra by generating a plurality of DRRs from a 3D CT image, and identifying respective first and second DRRs that match the 2D x-ray images of the vertebra. By identifying respective DRRs that match two or more x-ray images acquired from respective views, the x-ray images are registered to the 3D image data, and, in turn, the x-ray images are registered to one another via their registration to the 3D image data.

For some applications, in order to avoid double solutions when searching for a DRR that matches a given x-ray image, computer processor 22 first determines whether the x-ray image is, for example, AP, PA, left lateral, right lateral, left oblique, or right oblique, and/or from which quadrant a tool is being inserted. The computer processor may determine this automatically, e.g., by means of sets 50 of markers 52, using techniques described herein. Alternatively, such information may be manually inputted into the computer processor.

For some applications, in order to identify a DRR that matches a given x-ray image, computer processor 22 first limits the search space within which it is to search for a matching DRR, by applying the following steps. (It is noted that some of the steps are optional, and that some of the steps may be performed in a different order to that listed below.)

1. Information pertaining to the acquisition of the given x-ray images is retrieved. Typically, such information includes the angles of the different axes of the c-arm at the time of the acquisition of the image. It should be noted that such angles are typically relative to the base of the c-arm itself, not relative to the subject's body and typically not even relative to the surgical table (unless such table is integrated with the c-arm, which is less common). Additionally, such information may comprise the values of other imaging parameters (e.g., zoom level) that may be of use for limiting the search space.

For some applications, the information is included in standard (e.g., DICOM) image files generated by the x-ray system, and such files are transferred from the x-ray system to the processor, typically through a network connection.

For some applications, a capture device such as a frame grabber, which is connected to the computer that comprises processor 22, captures the screen image from the x-ray system. Typically, such capture is upon or immediately after the acquisition of the x-ray image and its display on the native x-ray screen. Such screen image typically includes not only the x-ray image but also additional (typically textual) information such as the values of the aforementioned different axes of the c-arm at the time of the acquisition of the image. For some applications, such values are read from the captured x-ray images by computer processor 22 using Optical Character Recognition (OCR).

For some applications, computer processor 22 is fitted previously with a configuration file pertaining to the model of the x-ray system with such file including instructions on the layout of the native x-ray screen including where each textual data is located, and the use by the processor of such file facilitates the identification of each desired data item (such as the angular value of a specific axis of the c-arm).

For some applications, such configuration file also includes the values of other imaging parameters characterizing the model of the x-ray system and/or the specific device, and is not limited to information that appears on the native screen of the x-ray system.

2. The angular values of the detectors of the CT scanner, relative to the table on which the subject is positioned and throughout the scan of the subject's body (or of the applicable portion thereof), are typically included in the standard (e.g., DICOM) image files generated by the scanner and loaded onto the computer that comprises processor 22.

3. For the generation of the DRRs from the CT data, the search space is narrowed to a subset that is relatively close in its viewing angles (typically relative to the scanner's table) to the angles of the axes of the c-arm during the acquisition of the x-ray image, and/or close with respect to other imaging parameters.

For some applications, for example if the subject is positioned on the back during the CT scan but on the stomach at the time the x-ray image is acquired, proper translation needs to be applied first, for example flipping the CT angles up-down and/or left-right.

For some applications, in order to identify a DRR that matches a given x-ray image, computer processor 22 first limits the search space within which it is to search for a matching DRR, by identifying the marker set or elements thereof in the x-ray image and applying prior knowledge with which it was provided of what the marker set or its elements look like from different viewing directions, or at different zoom levels, or at different camera openings, or any combination thereof. Typically, the search space is narrowed down to at or near simulated camera positions/values from which the marker set or elements thereof are known to appear in a similar manner to how they appear in the x-ray image.

For some applications, in order to identify a DRR that matches a given x-ray image, some combination of techniques described in the present application is applied.

For some applications, the registration of the 2D (e.g., x-ray) images with the 3D (e.g., CT) data is divided into a pre-processing phase and an online phase, i.e., during a medical procedure. Each of the two phases may be performed locally on a computer, or on a networked computer, or via cloud computing, or by applying any combination thereof.

Figure 30:
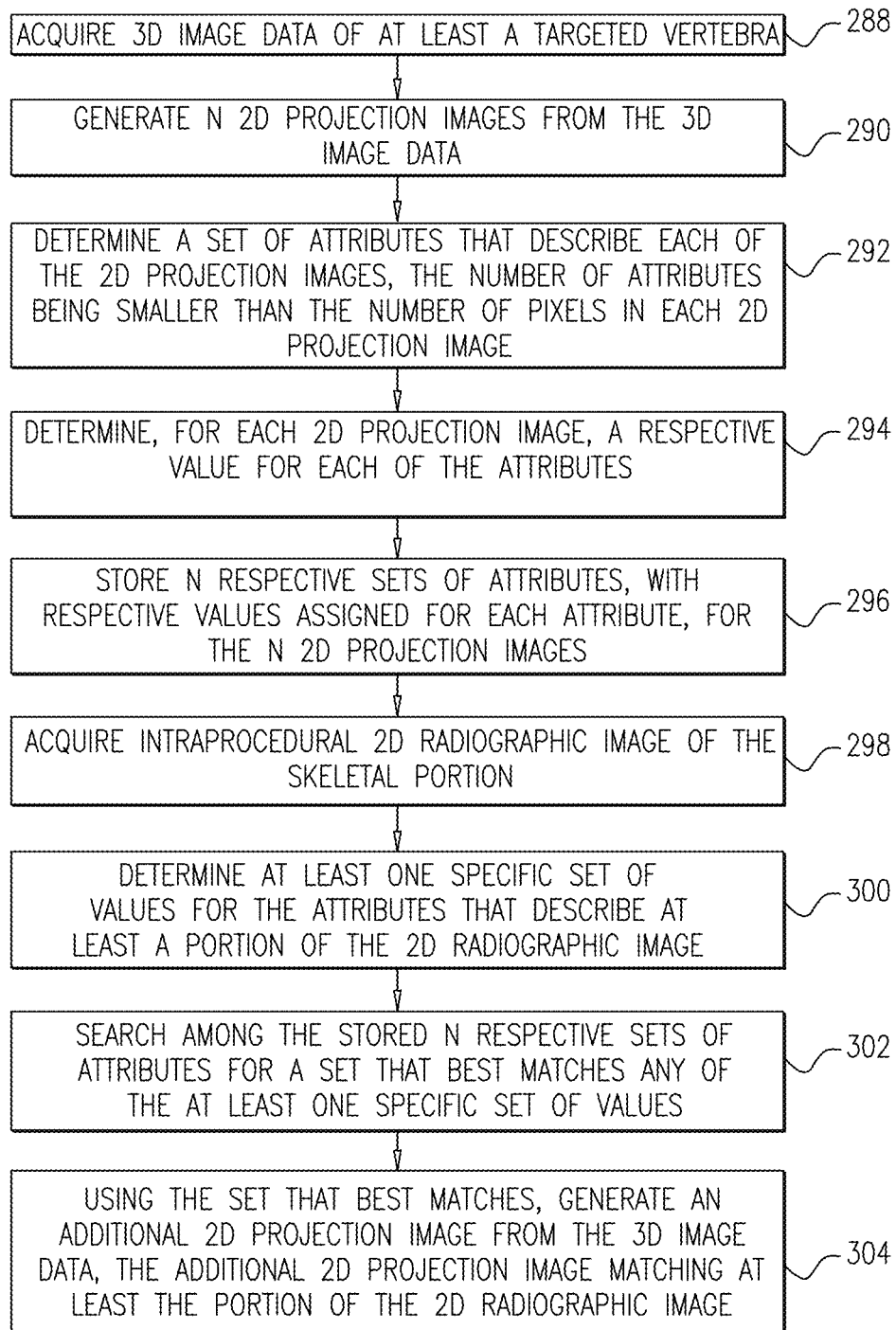
FIG. 30 is a flow chart for a method for dividing the registration into the pre-processing phase and online phase, i.e., during a medical procedure, in accordance with some applications of the present invention.

Reference is now made to FIG. 30, which is a flow chart for a method for dividing the registration into the pre-processing phase and online phase, i.e., during a medical procedure, in accordance with some applications of the present invention. For some applications, the pre-processing phases reduces the search space for the online phase. During the pre-processing phase, 3D image data of the skeletal portion is acquired (step 288), computer processor 22 is used to (i) generate N 2D projection images from the 3D image data (step 290), (ii) determine a set of attributes that describe each of the 2D projection images, the number of attributes being smaller than the number of pixels in each 2D projection image (step 292), (iii) determine for each 2D projection image a respective value for each of the attributes (step 294), and (iv) store N respective sets of attributes, with respective values assigned for each attribute, for the N 2D projection images (step 296). Thus, each data item in the original search space, in this case a DRR generated from the 3D scan data, is reduced in the pre-processing phase into a smaller number of characteristics, e.g., attributes. For some applications, after storing the N respective sets of attributes, the N 2D projection images are discarded.

During a medical procedure, i.e., in the online phase, only those characteristics then need to be matched with an x-ray image in the online phase, as follows: (i) a 2D radiographic image is acquired of the skeletal portion (step 298), (ii) computer processor 22 (*a*) determines at least one specific set of values for the attributes that describe at least a portion of the 2D radiographic image (step 300), (b) searches among the stored N respective sets of attributes for a set that best matches any of the at least one specific set of values (step 302), and (c) uses the set that best matches, to generate an additional 2D projection image from the 3D image data, the additional 2D projection image matching at least the portion of the 2D radiographic image (step 304).

Figure 31:
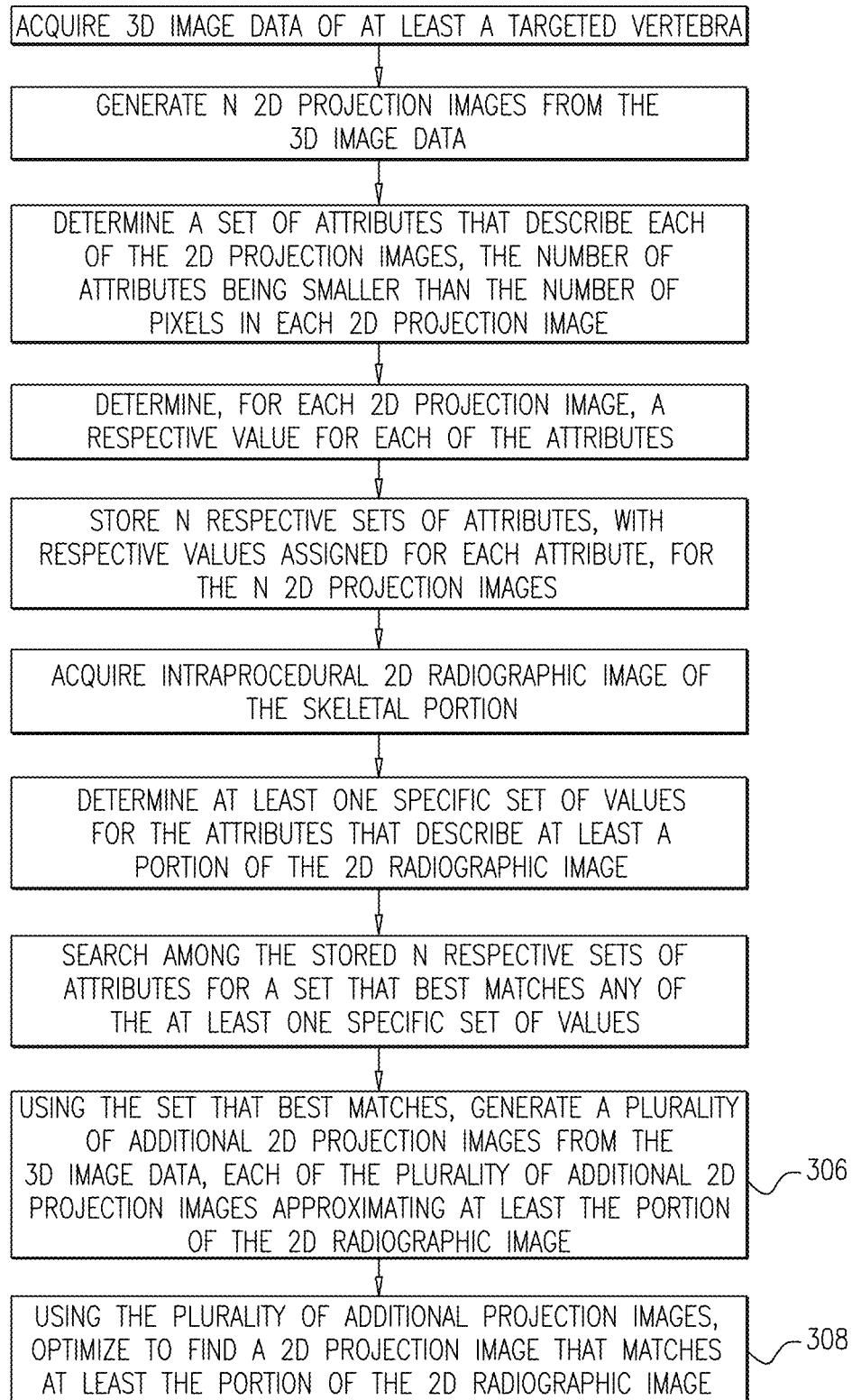
FIG. 31 is a flow chart for a method for dividing the registration into the pre-processing phase and online phase, i.e., during a medical procedure, in accordance with some applications of the present invention.

Reference is now made to FIG. 31, which is a flow chart for a method for dividing the registration into the pre-processing phase and online phase, i.e., during a medical procedure, in accordance with some applications of the present invention. For some applications, the above-described method is used for generating a first approximation and known techniques may then be used for the final match. In step 306 computer processor 22 (*a*) uses the set that best matches to generate a plurality of additional 2D projection images from the 3D image data, each of the plurality of additional projection images approximating at least the portion of the 2D radiographic image, and (b) using the plurality of additional projection images, optimizes (step 308) to find a 2D projection image that matches at least the portion of the 2D radiographic image.

For some applications, the pre-processing phase comprises the following steps (some of which are optional and the order of which may vary):

1. A targeted vertebra is marked upon the CT scan data by the user.
2. An approximate center of the vertebra, or a point of interest within the vertebra, is pointed at or calculated. It may also be marked as part of the aforementioned pre-surgery planning.
3. Several sectors, each around a common imaging angle of the x-ray that may be expected later on, during surgery (e.g., AP, left lateral, right lateral, left oblique, right oblique), are selected. For some applications, it may even be one sector comprising an entire dome, or even an entire sphere.
4. The data points within each sector typically include x-ray camera position in space, angles relative to the vertebra, distance to the vertebra or to the selected point within the vertebra, or any other applicable x-ray system parameter.
5. From each simulated x-ray system with its associated set of parameters, a DRR of the vertebra is generated, such that overall there are M DRRs.
6. Each DRR is presented as an N-dimensional vector, according to a similarity measure involved in 3D-2D registration (it is the same N for all DRRs). The coordinates of this vector are calculated from grayscale values of the DRR pixels. These calculations can include different image processing operations such as filtering, convolutions, normalization and others.
7. If there were M DRRs, then there are now M points in the said N-dimensional space.
8. Next, the M vectors are projected to a sub-space wherein the sub-space has fewer than N dimensions, let's say D dimensions. Typically, D is much smaller then N. One of the possible techniques for generating such sub-space, also known as Dimensionality Reduction techniques, is Principal Component Analysis (PCA). Other known techniques that may be applied include (See https://en.wikipedia.org/wiki/Dimensionality_reduction) Non-negative Matrix Factorization (NMF), or Kernel PCA, or Graph-based kernel PCA, or Linear discriminant analysis (LDA), or Generalized discriminant analysis (GDA), or any combination thereof.

Typically, in the new D-dimensional sub-space, there are M vectors, each corresponding to one of the M DRRs. Each of the M vectors is now reduced to a point with D coordinates in the D-dimensional subspace.

Typically, from M N-dimensional vectors representing DRRs, there has been a reduction to M points in a D-dimensional space. Therefore, the outcome is a great reduction, by several orders of magnitude, the amount of data that we shall need to search in the next phase which is the online phase.

For some applications, the online phase comprises the following steps (some of which being optional and the order of which may vary):

1. An x-ray image is acquired. A set of some or all of the values of the applicable parameters related to the x-ray source is: extracted from the display of the image, such as by means of OCR or pattern recognition; indicated by the user; deduced from analysis of the anatomy in the image; deduced from the appearance of the radio-opaque markers in the image; read from the DICOM file containing the image; received from the x-ray system; or any combination thereof
2. According to those values of those parameters, the sub-space corresponding to the same sector is searched, using the aforementioned similarity measure. Due to the aforementioned dimensionality reduction, the search can be done faster (by orders of magnitude) compared with a situation where the original N-dimensional space would have had to be searched. Typically, during this search phase there is no need to regenerate the DRRs that were generated in the pre-processing phase.
3. As a result of the search, a point in the D-dimensional subspace that best matches the current x-ray image is found. Typically, the DRR from which this point was generated is retrieved or re-generated and the x-ray image is co-registered with the CT scan of the same vertebra to obtain an initial approximation.
4. A fine-tuned 3D-2D co-registration follows. That is performed using known techniques such as CMA-ES (covariance matrix adaptation evolution strategy). A simulated x-ray source, corresponding to the actual DRR best-matching the x-ray image, is created.
5. If there is a singularity in the reconstruction in the CT data of the tool that is detected in the x-ray image, it is identified (typically automatically) and the user is prompted to change the position of the x-ray source and re-acquire an x-ray image. Examples for situations leading to a singularity include: two x-ray images acquired in a such way that planes containing the x-source and the tool projection on the x-ray detector coincide for both acquisitions a single x-ray image acquired where the tool is seen from a bull's-eye view.

For some applications, the steps of generating a plurality of DRRs from a 3D CT image, and identifying respective first and second DRRs that match the 2D x-ray images of the vertebra are aided by deep-learning algorithms.

For some applications, deep-learning techniques are performed as part of the processing of images of a subject's vertebra, as described in the following paragraphs. By performing the deep-learning techniques, the search space for DRRs of the subject's vertebra that match the x-ray images is limited, which reduces the intraprocedural processing requirement, reduces the time taken to performing the matching, and/or reduces cases of dual solutions to the matching.

For some applications, deep learning may be performed using 3D scan data only of the targeted vertebra, which typically greatly facilitates the task of building the deep-learning dataset. For some applications, during the deep-learning training phase, a large database of DRRs generated from the 3D data of the targeted vertebra, and (at least some of) their known parameters relative to vertebra, are inputted to a deep-learning engine. Such parameters typically include viewing angle, viewing distance, and optionally additional x-ray system and camera parameters. For some applications, the aforementioned parameters are exact. Alternatively, the parameters are approximate parameters. The parameters may be recorded originally when generating the DRRs, or annotated by a radiologist. Thus, the engine learns, given a certain 2D projection image, to suggest simulated camera and x-ray system viewing distances and angles that correspond to that projection image. Subsequently, the deep-learning data is fed as an input to computer processor 22 of system 20. During surgery, in order to register any of the 2D x-ray images to the 3D image data, computer processor uses the deep-learning data by inference in order to limit the search space in which DRRs of the 3D image data that match the x-ray images should be searched for. Computer processor 22 then searches for matching DRRs only within the search space that was prescribed by the deep-learning inference.

Figure 18:
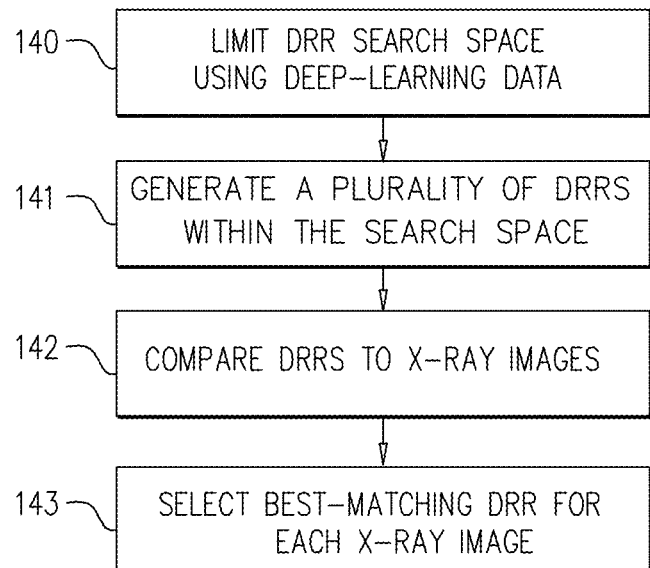
FIG. 18 is a flowchart showing steps that are performed by computer processor, in order to register 3D image data of a vertebra to two or more 2D x-ray images of the vertebra, in accordance with some applications of the present invention.

The above-described registration steps are summarized in FIG. 18, which is a flowchart showing steps that are performed by computer processor, in order to register 3D image data of a vertebra to two or more 2D x-ray images of the vertebra.

In a first step 140, the search space for DRRs that match respective x-ray images is limited, for example, using deep-learning data as described hereinabove. Alternatively or additionally, in order to avoid double solutions when searching for a DRR that matches a given x-ray image, the computer processor determines whether the x-ray images are, for example, AP, PA, left lateral, right lateral, left oblique, or right oblique, and/or from which quadrant a tool is being inserted.

In step 141, a plurality of DRRs are generated within the search space.

In step 142, the plurality of DRRs are compared with the x-ray images from respective views of the vertebra.

In step 143, based upon the comparison, the DRR that best matches each of the x-ray images of the vertebra is selected. Typically, for the simulated camera position that would generate the best-matching DRR, the computer processor determines the viewing angle and viewing distance of the camera from the 3D image of the vertebra.

It is noted that the above steps are performed separately for each of the 2D x-ray images that is used for the registration. For some applications, each time one or more new 2D x-ray images are acquired, the image(s) are automatically registered to the 3D image data using the above described technique. The 2D to 3D registration is thereby updated based upon the new 2D x-ray acquisition(s).

Figure 19A:
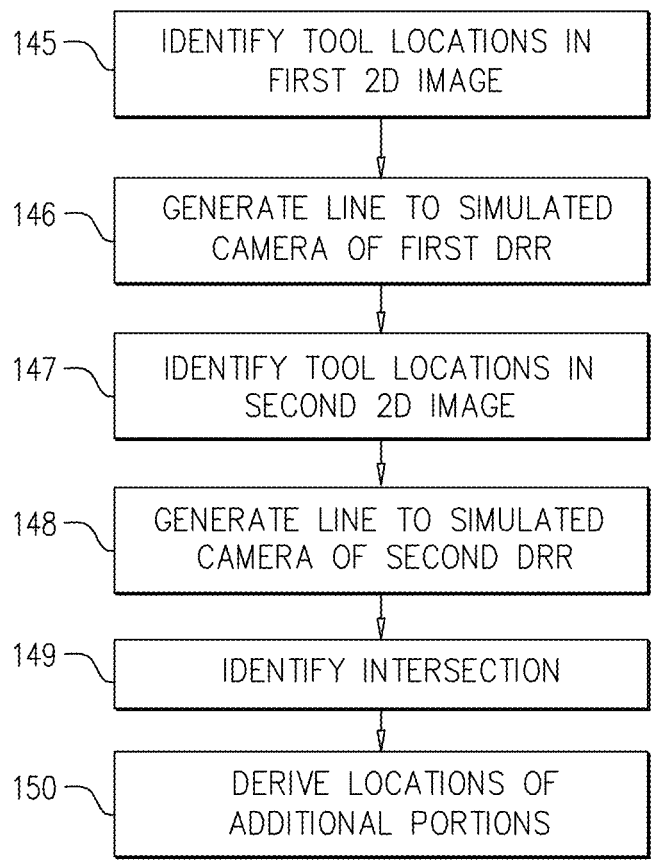
FIG. 19A is a flowchart showing steps of an algorithm that is performed by a computer processor, in accordance with some applications of the present invention.

Reference is now made to FIG. 19A, which is a flowchart showing steps of an algorithm that is performed by computer processor 22 of system 20, in accordance with some applications of the present invention.

As described hereinabove, for each of the x-ray images (denoted X1 and X2), the computer processor determines a corresponding DRR from a simulated camera view (the simulated cameras being denoted C1 for X1 and C2 for X2).

The 3D scan and two 2D images are now co-registered, and the following 3D-2D bi-directional relationship generally exists:

Geometrically, a point P3D in the 3D scan of the body portion (in three coordinates) is at the intersection in 3D space of two straight lines
i. A line drawn from simulated camera C1 through the corresponding point PX1 (in two image coordinates) in 2D image X1.
ii. A line drawn from simulated camera C2 through the corresponding point PX2 (in two image coordinates) in 2D image X2.

Therefore, referring to FIG. 19A, for some applications, for a portion of a tool that is visible in the 2D images, such as the tool tip or a distal portion of the tool, the computer processor determines its location within the 3D image data (denoted TP3D), using the following algorithmic steps:

Step 145: Identify, by means of image processing, the tool's tip TPX1 in image X1 (e.g., using the image processing techniques described hereinabove). For some applications, to make the tool tip point better defined, the computer processor first generates a centerline for the tool and then the tool's distal tip TPX1 is located upon on that centerline.

In general, the computer processor identifies the locations of a tool or a portion thereof in the 2D x-ray images, typically, solely by means of image processing. For example, the computer processor may identify the tool by using a filter that detects pixel darkness (the tool typically being dark), using a filter that detects a given shape (e.g., an elongated shape), and/or by using masks. For some applications, the computer processor compares a given region within the image to the same region within a prior image. In response to detecting a change in some pixels within the region, the computer processor identifies these pixels as corresponding to a portion of the tool. For some applications, the aforementioned comparison is performed with respect to a region of interest in which the tool is likely to be inserted, which may be based upon a known approach direction of the tool. For some applications, the computer processor identifies the portion of the tool in the 2D images, solely by means of image processing, using algorithmic steps as described in US 2010-0161022 to Tolkowsky, which is incorporated herein by reference. For some applications, the computer processor identifies the portion of the tool in the 2D images, solely by means of image processing, using algorithmic steps as described in US 2012-0230565 to Steinberg, which is incorporated herein by reference. For some applications, the tool or portion thereof is identified manually, and pointed at on one or more of the images, by the operator.

For some applications, identification of the portion of the tool in the 2D images is facilitated, manually or automatically, by defining a region of interest (ROI) in a 2D image around the planned insertion line of the tool, as such line was determined in the planning phase using techniques described by the present application, and then registered to the 2D image using techniques described by the present application. Next, the portion of the tool is searched within the ROI using techniques described by the present application.

Figure 19C:
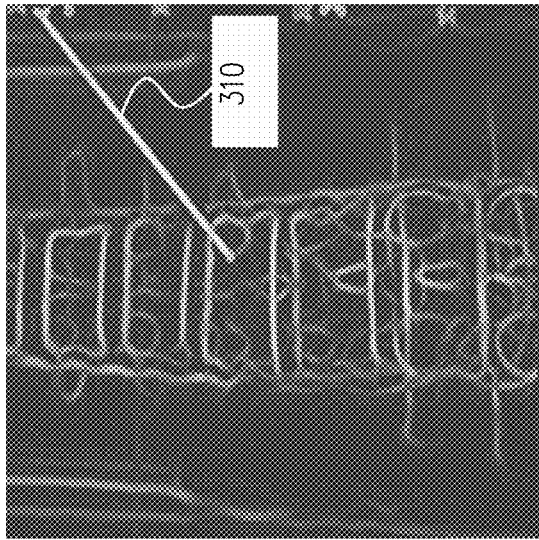
FIGS. 19B-19E show an example of the automatic detection within an x-ray image of a tool that is inserted into a vertebra, in accordance with some applications of the present invention.
Figure 19E:
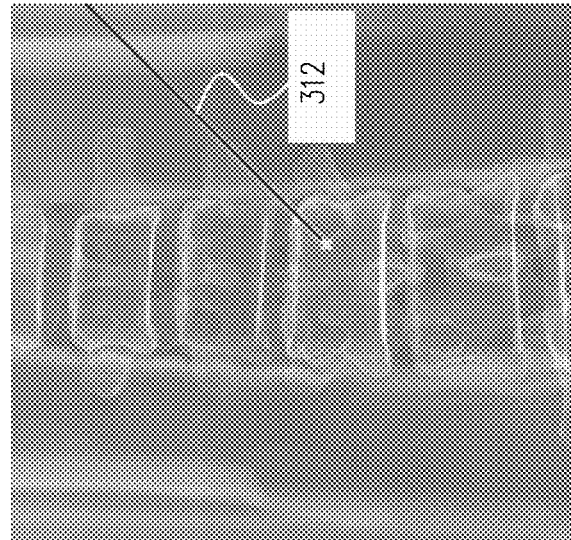
Figure 19B:
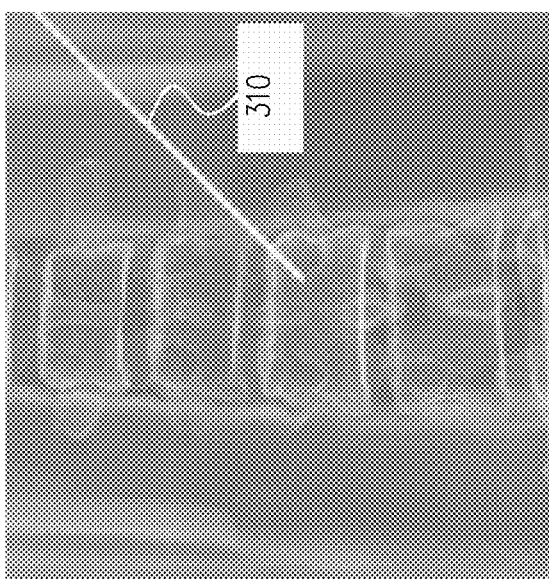
Figure 19D:
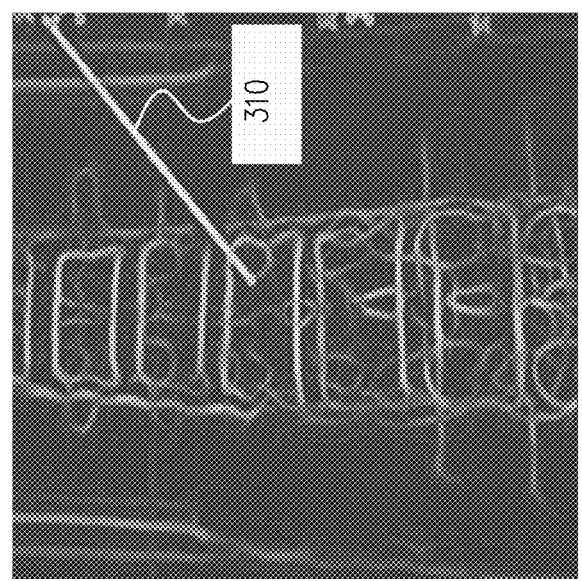

Reference is made to FIGS. 19B-E, showing an example of the automatic detection within an x-ray image, using the MatLab computing environment, of a tool that is inserted into a vertebra. FIG. 19B shows an x-ray image in which a tool 310 may be observed. FIG. 19C shows an outcome of activating "vesselness" detection upon the x-ray image. FIG. 19D shows an outcome after applying a threshold to the vesselness measure. FIG. 19E shows a line 312 representing the detected tool, which overlaps the actual tool, in the x-ray image.

Step 146: Generate a typically-straight line L1 from C1 to TPX1. (It is noted that, as with other steps described as being performed by the computer processor, the generation of a line refers to a processing step that is the equivalent of drawing a line, and should not be construed as implying that a physical line is drawn. Rather the line is generated as a processing step).

Step 147: Identify, by means of image processing, the tool's tip TPX2 in image X2 (e.g., using the image processing techniques described hereinabove). For some applications, to make the tool tip point better defined, the computer processor first generates a centerline for the tool and then the tool's distal tip TPX2 is located upon on that centerline. The image processing techniques that are used to tool's tip TPX2 in image X2 are generally similar to those described above with reference to step 145.

Step 148: Generate a typically-straight line L2 from C2 to TPX2.

Step 149: Identify the intersection of L1 and L2 in 3D space as the location of the tool's tip relative to the 3D scan data.

Step 150: Assuming that the shape of the tool is known (e.g., if the tool is a rigid or at least partially rigid tool, or if the tool can be assumed to have a given shape by virtue of having been placed into tissue), the computer processor derives the locations of additional portions of the tool within 3D space. For example, in the case of a tool with straight shaft in whole or in its distal portion, or one that may be assumed to be straight once inserted into bone, or at least straight in its distal portion once inserted into bone, then this shaft, or at least its distal portion, resides at the intersection of two planes, each extending from the simulated camera to the shaft (or portion thereof) in the corresponding 2D image. For some applications, the direction of the shaft from its tip to proximal and along the intersection of the two planes is determined by selecting a point proximally to the tool's tip on any of the x-ray images and observing where a line generated between such point and the corresponding simulated camera intersects the line of intersection between the two planes.

It is noted that, since the co-registration of the 3D image data to the 2D images is bidirectional, for some applications, the computer processor identifies features that are identifiable within the 3D image data, and determines the locations of such features with respect to the 2D x-rays, as described in further detail hereinbelow. The locations of each such feature with respect to any of the 2D x-rays are typically determined by (a) generating a typically-straight line from the simulated camera that was used to generate the DRR corresponding to such x-ray image and through the feature within the 3D image data and (b) thereby determining the locations of the feature with respect to the x-ray images themselves. For some applications, the locations of such features with respect to the 2D x-ray images are determined by determining the locations of the features within the DRRs that match the respective x-ray images, and assuming that the features will be at corresponding locations within the matching x-ray images.

For some applications, based upon the registration, 3D image data is overlaid upon a 2D image. However, typically, the 3D image data (e.g., a 3D image, a 2D cross-section derived from 3D image data, and/or a 2D projection image derived from 3D image data) are displayed alongside 2D images, as described in further detail hereinbelow.

Figure 20A:
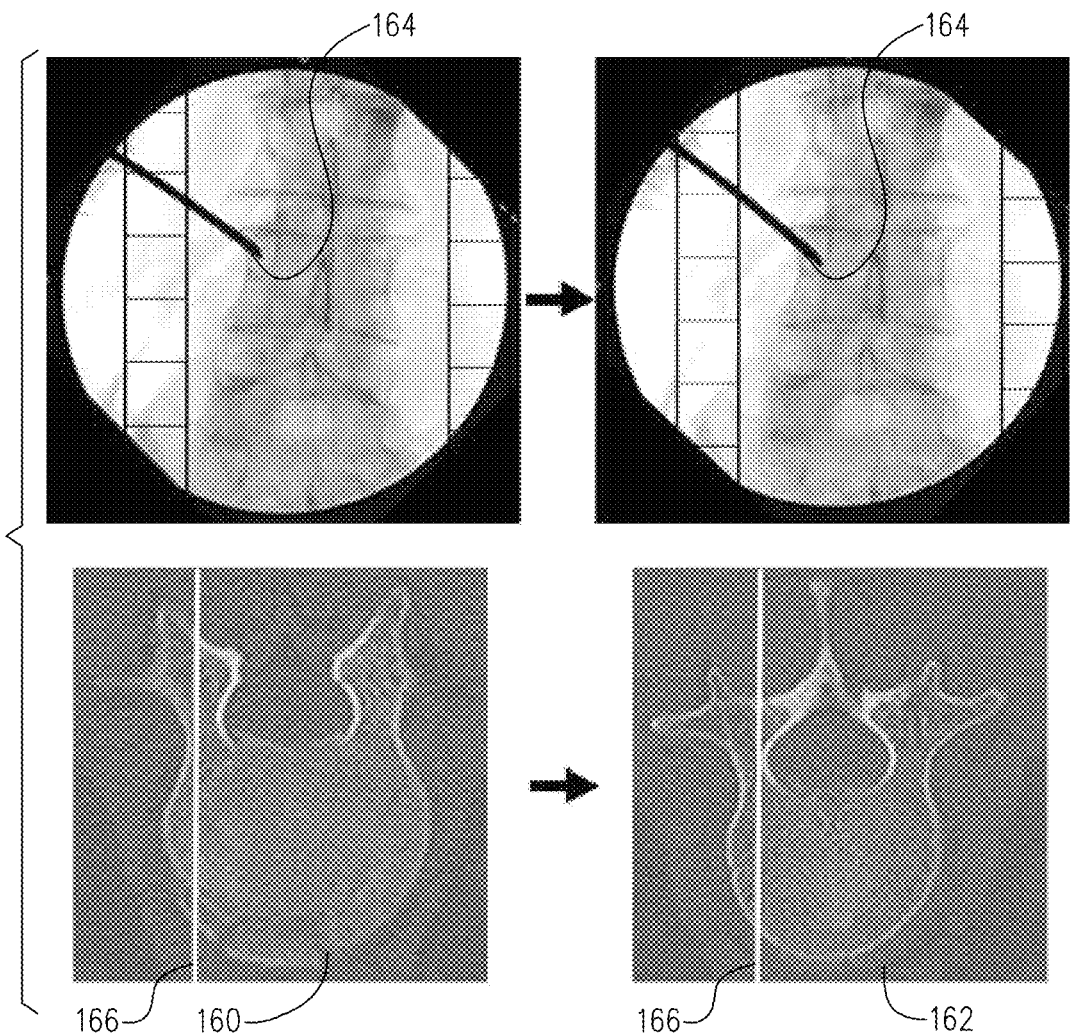
FIG. 20A shows an example of axial cross-sections of a vertebra corresponding, respectively, to first and second locations of a tip of a tool that is advanced into the vertebra along a longitudinal insertion path, as shown on corresponding 2D x-ray images that are acquired from a single x-ray image view, in accordance with some applications of the present invention.

Reference is now made to FIG. 20A, which shows an example of cross-sections 160 and 162 of a vertebra corresponding, respectively, to first and second locations of a tip 164 of a tool that is advanced into the vertebra along a longitudinal insertion path, as shown on corresponding 2D x-ray images, in accordance with some applications of the present invention. Typically, the tool has a straight shaft in whole or in its distal portion, and/or may be assumed to be straight once inserted into bone, or at least straight in its distal portion once inserted into bone. Referring also to step 84 of FIG. 6, for some applications, based upon the identified location of the tip of tool with respect to one or more 2D x-ray image of the vertebra that are acquired from a single image view, and the registration of an x-ray from the single 2D x-ray image view to the 3D image data (e.g., by matching a DRR from the 3D image data to the 2D x-ray image), computer processor 22 determines a location of the tip of the tool with respect to a DRR that is derived from the 3D image data (e.g., the DRR that was determined to match the 2D x-ray image), and in response thereto, drives the display to display a cross-section of the vertebra, the cross-section being derived from the 3D image data, and corresponding to the location of the tool tip. The cross-section is typically of a given plane at the identified location. Typically, the cross-section is an axial cross-section, but for some applications, the cross-section is a sagittal cross-section, a coronal cross-section, and/or a cross-section that is perpendicular to or parallel with the direction of the tool insertion.

For some applications, upon the cross-section, the computer processor drives the display to show a line 166 (e.g., a vertical line), indicating that the location of the tip of the tool is somewhere along that line. For some applications, the line is drawn vertically upon an axial cross-section of the vertebra, as shown. For some applications, the surgeon is able to determine the likely location of the tool along the line based upon their tactile feel. Alternatively or additionally, based on the 3D image data, the computer processor drives the display to display how deep below the skin the vertebra is disposed, which acts as a further aid to the surgeon in determining the location of the tool along the line.

As noted above, typically it is possible to generate an output as shown in FIG. 20A, by acquiring one or more 2D x-ray images from only a single x-ray image view of the tool and the vertebra, and registering one of the 2D x-ray images to the 3D image data using the registration techniques described herein. Typically, by registering the 2D x-ray image acquired from the single image view to the 3D image data, computer processor 22 determines, with respect to 3D image data (e.g., with respect to the DRR that was determined to match the 2D x-ray image), (a) a plane in which the tip of the tool is disposed, and (b) a line within the plane, somewhere along which the tip of the tool is disposed, as shown in FIG. 20A. As described hereinabove, typically, when the tip of the tool is disposed at an additional location with respect to the vertebra, further 2D x-ray images of the tool at the additional location are acquired from the same single x-ray image view, or a different single x-ray image view, and the above-described steps are repeated. Typically, for each location of the tip of the tool to which the above-described technique is applied, 2D x-ray images need only be acquired from a single x-ray image view, which may stay the same for the respective locations of the tip of the tool, or may differ for respective locations of the tip of the tool.

Figure 20B:
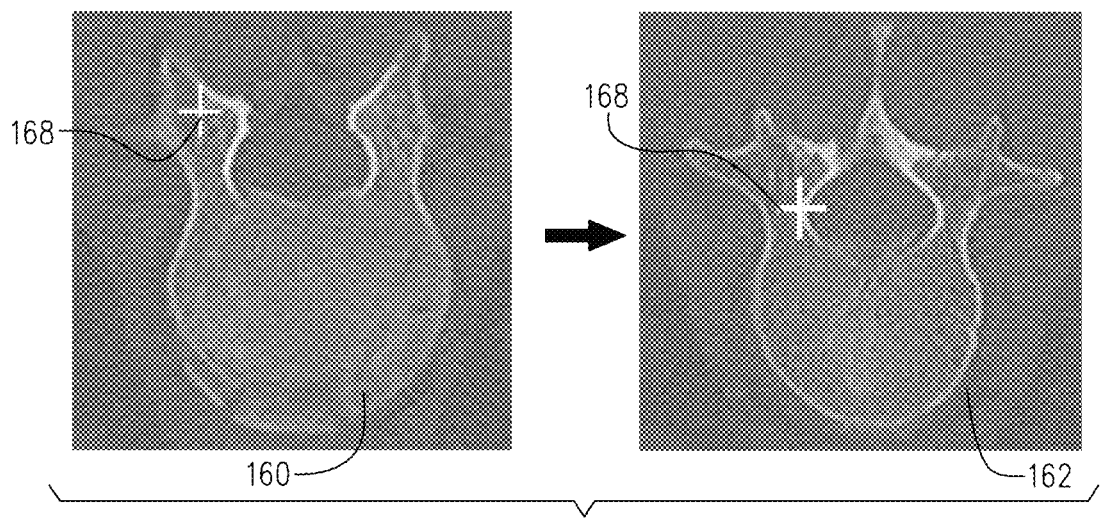
FIG. 20B shows an example of axial cross-sections of a vertebra upon which, respectively, first and second locations of a tip of a tool that is advanced into the vertebra along a longitudinal insertion path are displayed, the locations being derived using x-ray images acquired from two or more x-ray image views, in accordance with some applications of the present invention.

Reference is now made to FIG. 20B, which is a schematic illustration of the location of the tool tip 168 denoted by cross-hairs upon cross-sections 160 and 162 of the vertebra corresponding, respectively, to first and second locations of a tip 164 of a tool that is advanced into the vertebra along a longitudinal insertion path (as shown in FIG. 15A), in accordance with some applications of the present invention. For some applications, by initially registering two or more 2D x-ray images of the tool and the vertebra that were acquired from respective 2D x-ray image views, to the 3D image data, the precise location of the tip of the tool within a cross-section derived from the 3D image data is determined and indicated upon the cross-section, as shown in FIG. 20A. As described hereinbelow, with reference to FIGS. 25A-25B, for some applications, after initially determining the location of the tip of the tool with respect to the 3D image data using two or more 2D x-ray images of the tool and the vertebra that were acquired from respective 2D x-ray image views, subsequent locations of the tip of the tool are determined with respect to the 3D image data by acquiring further x-ray images from only a single x-ray image view.

Figure 21A:
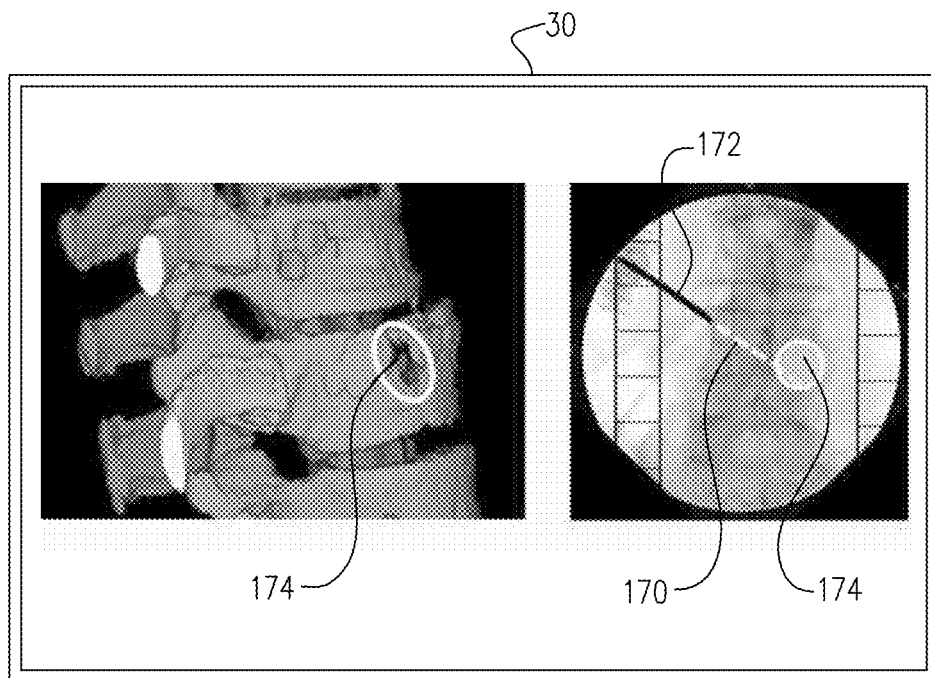
FIGS. 21A and 21B show examples of a display showing a given location designated upon 3D (e.g., CT or MRI) image data and a relationship between an anticipated longitudinal insertion path of a tool and the given location upon, respectively, AP and lateral 2D x-ray images, in accordance with some applications of the present invention.
Figure 21B:
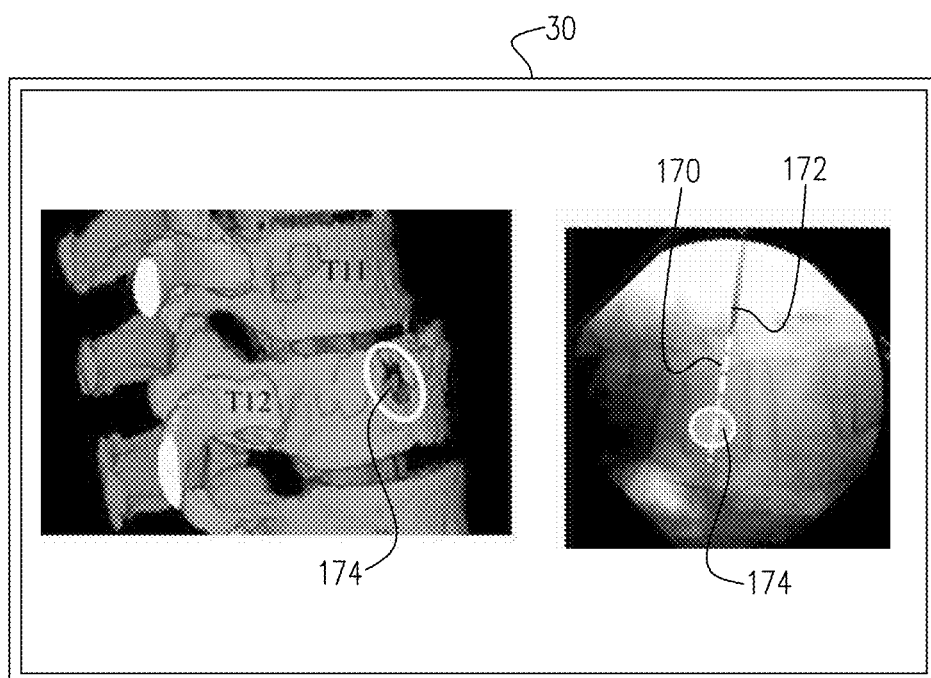

Reference is now made to FIGS. 21A and 21B, which show examples of a display showing a relationship between an anticipated longitudinal insertion path 170 of a tool 172 and a designated location 174 upon, respectively, AP and lateral 2D x-ray images, in accordance with some applications of the present invention. Reference is also made to step 86 of FIG. 6.

For some applications, a location within a vertebra is designated within the 3D image data. For example, an operator may designate a target portion (e.g. a fracture, a tumor, a virtual pedicle screw, etc.), and/or a region which the tool should avoid (such as the spinal cord) upon the 3D image data (e.g., a 3D image, a 2D cross-section derived from 3D image data, and/or a 2D projection image derived from 3D image data). Alternatively or additionally, the computer processor may identify such a location automatically, e.g., by identifying the portion via image processing. Based upon the registration of the first and second 2D x-ray images to the 3D image data, the computer processor derives a position of the designated location within at least one of the x-ray images, using the techniques described hereinabove. In addition, the computer processor determines an anticipated path of the tool within the x-ray image. Typically, the computer processor determines the anticipated path by determining a direction of an elongate portion of the tool (and/or a center line of the elongate portion) within the x-ray image. Since the tool is typically advanced along a longitudinal insertion path, the computer processor extrapolates the anticipated path by extrapolating a straight line along the determined direction.

For some applications, the computer processor performs a generally similar process, but with respect to a desired approach vector (e.g., for insertion and implantation of a screw) that, for example, is input into the computer processor manually, and/or is automatically derived by the processor. For example, such an approach vector may have been generated during a planning phase, typically upon the 3D image data, and based upon the insertion of a simulated tool into the vertebra. Typically, such an approach vector is one that reaches a desired target, while avoiding the spinal cord or exiting the vertebra sideways.

For some applications, in response to the above steps, the computer processor generates an output indicating a relationship between the anticipated longitudinal insertion path of the tool and the designated location. For some applications, the computer processor generates an output on the display, e.g., as shown in FIGS. 21A and 21B. Alternatively or additionally, the computer processor may generate instructions to the operator to redirect the tool. Further alternatively or additionally, the computer processor may generate an alert (e.g., an audio or visual alert) in response to detecting that the tool is anticipated to enter a region that should be avoided (such as the spinal cord) or is anticipated to exit the vertebra sideways in the other direction.

Referring again to step 90 of FIG. 6, for some applications, computer processor 22 determines a location of a portion of the tool with respect to the vertebra, within the x-ray images, by means of image processing, as described hereinabove. Based upon the identified location of the portion of the tool within the x-ray images, and the registration of the first and second 2D x-ray images to the 3D image data, the computer processor determines the location of the portion of the tool with respect to the 3D image data. For some applications, in response thereto, the computer processor shows an image of the tool itself, or a symbolic representation thereof, overlaid upon the 3D image data. Alternatively or additionally, the computer processor derives a relationship between the location of the portion of the tool with respect to the 3D image data and a given location within the 3D image data, and generates an output that is indicative of the relationship. As described hereinabove, the registration of the 2D images to the 3D image data is typically performed with respect to individual vertebrae. Therefore, even is the subject has moved between the acquisition of the 3D image data and the acquisitions of the 2D images, the techniques described herein are typically effective.

For some applications, the representation of the actual tool (or of a portion thereof) is displayed relative to the planned path of insertion, in accordance with techniques described by the present application. For some applications, the planned path of insertion is generated by embodiments of the present invention. For some applications, the actual tool vs. the planned path is displayed upon a 2D slice or a 2D projection of the 3D data. For some applications, the actual tool vs. the planned path is displayed upon a 3D model generated from the 3D data, with such model typically having some level of transparency allowing to see the representations within it. For some applications, the 3D model is auto-rotated to facilitate the operator's spatial comprehension of actual tool vs. planned path. For some applications, the actual tool vs. the planned path is displayed upon a 2D x-ray image in which the tool can be observed and with the planned path registered from the 3D data, for example by means of matching a DRR generated from the 3D data and comprising the planned path with the 2D x-ray image. For some applications, the planned path comprises one or more points along the path, such as the incision site at skin level, the entry point into the vertebra, the out-of-pedicle point, and the target point, or any combination thereof.

Figure 21C:
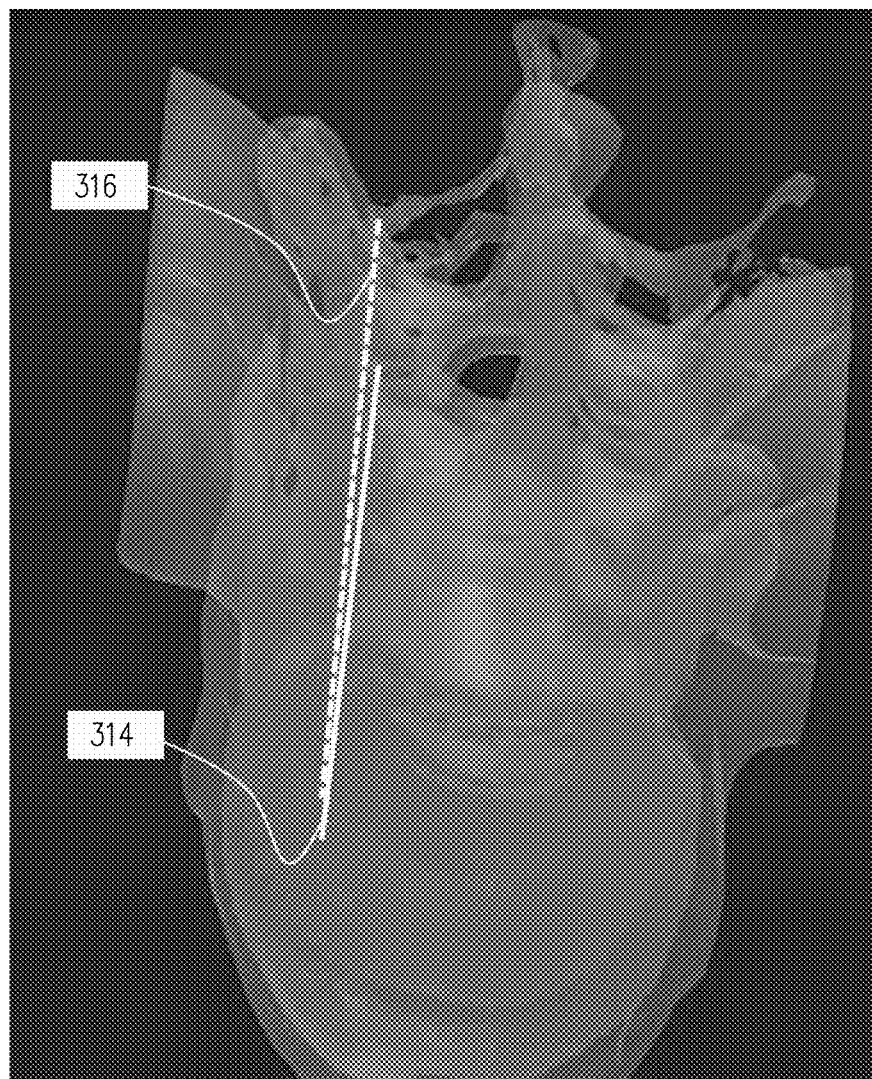
FIG. 21C shows an example of the representations of a portion of an actual tool and the planned insertion path displayed together within a semi-transparent 3D model of a spinal segment, in accordance with some applications of the present invention.

Reference is made to FIG. 21C, which shows an example of the representations of a portion of an actual tool 314 (solid line) and the planned insertion path 316 (dashed line) displayed within a semi-transparent 3D model of a spinal segment, in accordance with some applications of the present invention.

For some applications, the computer processor generates an output that is indicative of the distance of the tip of the tool from the spinal cord and/or outer vertebral border, e.g., using numbers or colors displayed with respect to the 3D image data. For some applications, the computer processor outputs instructions (e.g., textual, graphical, or audio instructions) indicating that the tool should be redirected. For some applications, as an input to this process, the computer processor determines or receives a manual input indicative of a direction or orientation from which the tool is inserted (e.g., from top or bottom, or left or right).

Figure 22A:
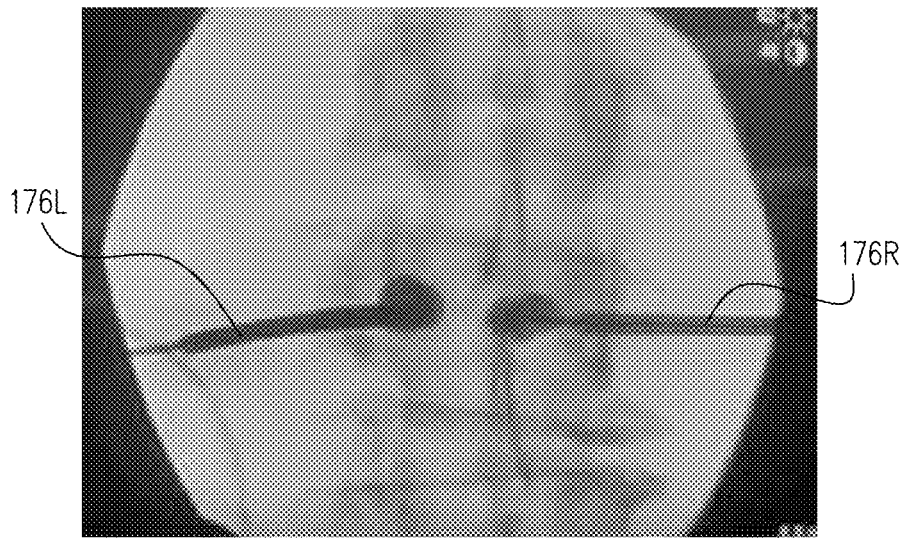
FIG. 22A shows an AP x-ray of two tools being inserted into a vertebra through, respectively, 10-11 o'clock and 1-2 o'clock insertion windows, the AP x-ray being generated using prior art techniques.
Figure 22B:
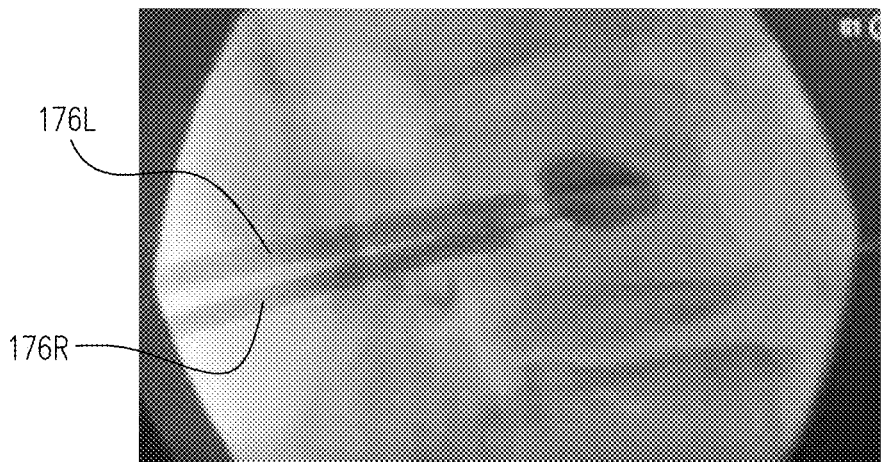
FIG. 22B shows a corresponding lateral x-ray image to FIG. 17A, the lateral x-ray being generated using prior art techniques.

Reference is now made to FIG. 22A, which shows an AP x-ray of two tools 176L and 176R being inserted into a vertebra through, respectively, 10-11 o'clock and 1-2 o'clock insertion windows, and to FIG. 22B, which shows a corresponding lateral x-ray image to FIG. 22A, the images being acquired in accordance with prior art techniques. As described hereinabove, in many cases, during spinal surgery, two or more tools are inserted into a vertebra, for example, from the 10 o'clock to 11 o'clock insertion window and from the 1 o'clock to 2 o'clock insertion window, with the process repeated, as applicable, for one or more further vertebrae. Within the AP x-ray view, tools 176L and 176R, inserted into respective windows, are typically discernible from one another, as shown in FIG. 22A. Furthermore, with reference to FIGS. 5A-B, for some applications, within the AP view, the computer processor discerns between tool inserted via the respective insertion windows based upon the arrangements of marker sets 50. However, if the tools are of identical or similar appearance, then from some imaging directions it is challenging to identify which tool is which. In particular, it is challenging to identify which tool is which in lateral x-ray views, as may be observed in FIG. 22B. In general, it is possible to discern between tools in images acquired along the direction of insertion, and more difficult to discern between tools in images acquired along other directions.

Figure 23A:
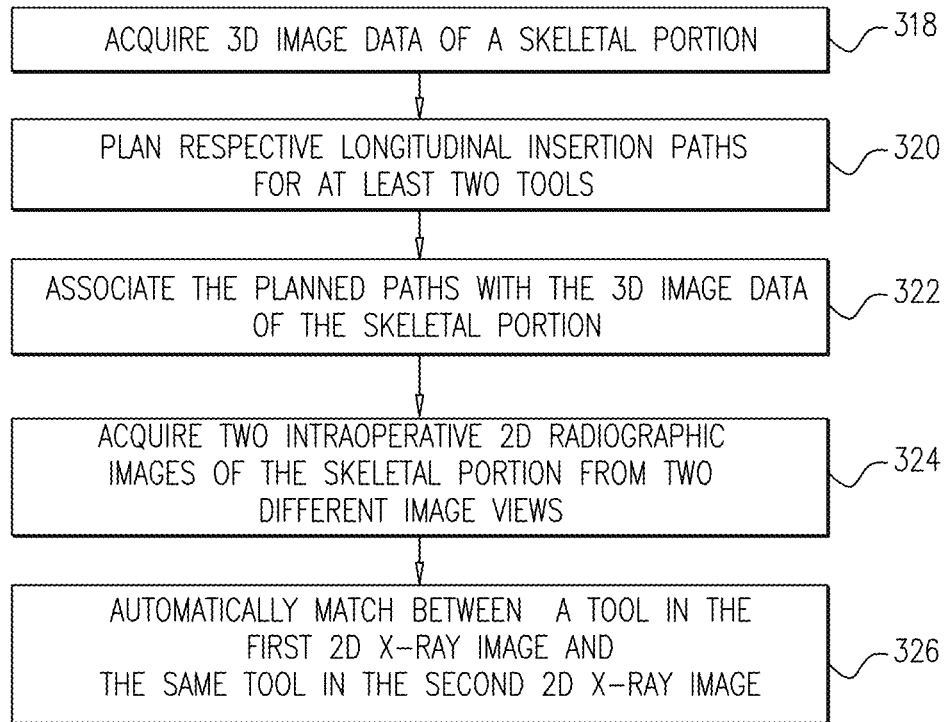
FIGS. 23A and 23B are flowcharts for a method for matching between a tool in one x-ray image acquired from a first view, and the same tool in a second x-ray image acquired from a second view, in accordance with some applications of the present invention.
Figure 23B:
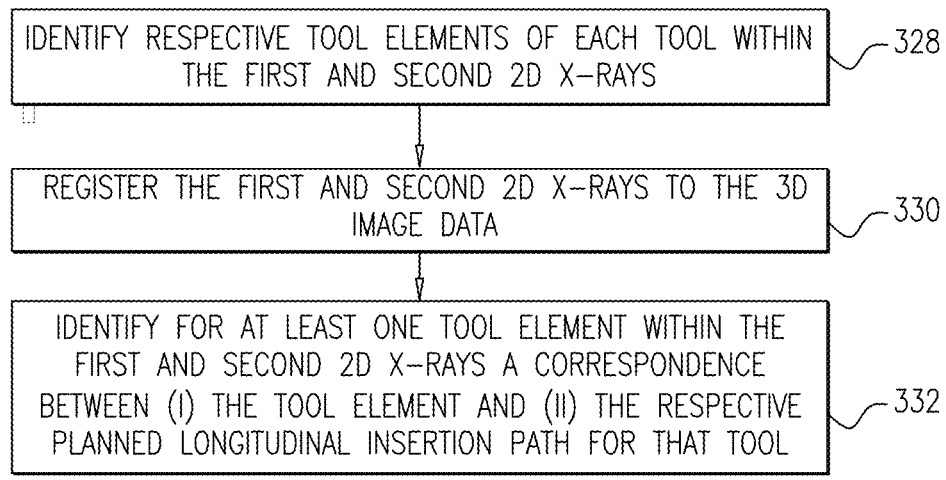

Reference is now made to FIGS. 23A-B, which show flowcharts for matching between a tool in one x-ray image acquired from a first view, and the same tool in a second x-ray image acquired from a second view. For some applications, computer processor 22 matches automatically between a tool in one x-ray image acquired from a first view, and the same tool in a second x-ray image acquired from a second view, using techniques described by the present application and comprising the following steps:
 (i) acquiring 3D image data of a skeletal portion (step 318),
 (ii) planning respective longitudinal insertion paths for each of at least two tools (step 320),
 (iii) associating the planned respective longitudinal insertion paths with the 3D image data (step 322),
 (iv) while respective portions of the tools are disposed at first respective locations along their respective longitudinal insertion paths with respect to the skeletal portion, acquiring two 2D x-ray images of the skeletal portion from two different respective image views (step 324) (typically using an x-ray imaging device that is not registered with respect to the subject's body), and
 (v) using computer processor 22, automatically matching between a tool in the first 2D x-ray image and the same tool in the second 2D x-ray image (step 326).

FIG. 23B shows the steps computer processor 22 performs to do the automatic matching, as follows:
 (A) identifying respective tool elements of each of the tools within each of the first and second 2D x-ray images, by means of image processing (step 328),
 (B) registering the first and second x-ray images to the 3D image data, as described hereinabove (step 330), and (C) based upon the identified respective tool elements within the first and second 2D x-ray images, and the registration of the first and second 2D x-ray images to the 3D image data, identifying for at least one tool element within the first and second 2D x-ray images a correspondence between the tool element and the respective planned longitudinal insertion path for that tool (step 332), i.e., the planned insertion line of each tool is matched with the tool observed in the x-ray images to be nearest that line, after the planning data from the CT has been projected (i.e., overlaid) onto the x-ray image.

Once a correspondence is made in both the first and second x-rays between a tool element in the x-rays and its corresponding planned longitudinal insertion path, computer processor 22 thus identifies which tool in the first x-ray is the same tool in the second x-ray and can then position respective representations of the respective tool elements within a display of the 3D image data.

For some applications, the computer processor matches automatically between a tool in one x-ray image acquired from a first view, and the same tool in a second x-ray image acquired from a second view, by defining a region of interest (ROI) in each x-ray image around the planned insertion line of the tool, as such line was determined in the planning phase using techniques described by the present application and then registered to the 2D image using techniques described by the present application, and then matching between instances of the tool, or portions thereof, that appear in both ROIs.

For some applications, the planned insertion line of each tool is displayed distinctively, e.g., each in a unique color within the 3D image data. The planned respective longitudinal insertion paths may also be distinctively overlaid on the first and second x-ray images, facilitating identification of each insertion path in the x-ray images on which the planning data has been projected (i.e., overlaid), and thus facilitating manual association of each tool with a nearby planned insertion line, e.g., how close the tool is to the planned insertion line, in each of the x-ray images and for each tool among the x-ray images.

For some applications, the planning data (or portions thereof) is, using techniques described by the present application, projected and displayed upon each x-ray image that is acquired and registered with the 3D data. For some applications, a first tool (e.g., needle, wire) seen in an x-ray image is distinguished, typically automatically and typically be means of image processing, from a second tool (e.g., forceps) used to grab the first tool, by the first tool having a single longitudinal shaft and the second tool having a dual longitudinal shaft.

Referring again to step 90 of FIG. 6, for some applications, rather than displaying the tool, a representation thereof, and/or a path thereof upon a 3D image, the computer processor drives the display to display the tool, a representation thereof, and/or a path thereof upon a 2D cross-section of the vertebra that is derived from the 3D image. For some applications, the computer processor determines the location of the centerline of the tool shaft, by means of image processing. For example, the computer processor may use techniques for automatically identifying a centerline of an object as described in US 2010-0161022 to Tolkowsky, which is incorporated herein by reference. For some applications, the computer processor drives the display to display the centerline of the tool upon the 3D image data, the end of the centerline indicating the location of the tool tip within the 3D image data. Alternatively or additionally, the computer processor drives the display to display an extrapolation of the centerline of the tool upon the 3D image data, the extrapolation of the centerline indicating an anticipated path of the tool with respect to the 3D image data. For some applications, the computer processor drives the display to display a dot at the end of the extrapolated centerline upon the 3D image data, the dot representing the anticipated location of the tip of the tool.

For some applications, the computer processor drives the display to display in a semi-transparent format a 3D image of the vertebra with the tool, a representation thereof, and/or a path thereof disposed inside the 3D image. Alternatively or additionally, the computer processor drives the display to rotate the 3D image of the vertebra automatically (e.g., to rotate the 3D image back-and-forth through approximately 30 degrees). For some applications, the computer processor retrieves an image of a tool of the type that is being inserted from a library and overlays the image upon the derived centerline upon the 3D image data. Typically, the tool is placed along the centerline at an appropriate scale with the dimensions being derived from the 3D image data. For some applications, a cylindrical representation of the tool is overlaid upon the derived centerline upon the 3D image data. For some applications, any one of the above representations is displayed relative to a predesignated tool path, as derived automatically by processor 22, or as input manually by the surgeon during a planning stage.

Referring again to FIG. 2, tool insertion into a vertebra must avoid the spinal cord 42, and at the same time needs to avoid exiting the vertebra from the sides, leaving only two narrow tool insertion windows 44, on either side of the vertebra. Typically, the greater the level of protrusion of a tool or implant into the spinal cord, the worse the clinical implications. For some applications, volumes within the 3D image of the vertebra (and/or a cross-sectional image derived therefrom) are color coded (e.g., highlighted) to indicate the level of acceptability (or unacceptability) of protrusion into those volumes. For some applications, during the procedure, the computer processor determines the location of the tool with respect to the 3D image data, and in response thereto, the computer processor drives the display to highlight a vertebral volume into which there is a protrusion that is unacceptable. For some applications, the computer processor drives the display to display a plurality (e.g., 2-6) of, typically concentric, cylinders within the 3D image of the vertebra, the cylinders indicating respective levels of acceptability of protrusion of a tool into the volumes defined by the cylinders. During the procedure, the computer processor determines the location of the tool with respect to the 3D image data, and in response thereto, the computer processor drives the display to highlight the cylinder in which the tool or a portion thereof is disposed, and/or is anticipated to enter. For some applications, the computer processor performs the above-described functionalities, but not with respect to the tool that is currently being inserted (which may be a narrow tool, such as a needle), rather with respect to the eventual implant (e.g., a pedicle screw, which typically has a larger diameter) that will be positioned later using the current tool. For some applications, the computer processor performs the above-described steps with respect to a 2D cross-sectional image that is derived from the 3D image data. For such cases, rectangles, rather than cylinders are typically used to represent the respective levels of acceptability of protrusion of a tool into the areas defined by the rectangles.

For some applications, the processor allows a 3D image of the vertebra with the tool, a representation of the tool, and/or a path of the tool indicated within the image to be rotated, or the processor rotates the image automatically, in order for the user to better understand the 3D placement of the tool. It is noted that, since the images of the vertebra and the tool were input from different imaging sources, the segmented data of what is the tool (or its representation) and what is the vertebra is in-built (i.e., it is already known to the computer processor). For some applications, the computer processor utilizes this in-built segmentation to allow the operator to virtually manipulate the tools with respect to the vertebra. For example, the operator may virtually advance the tool further along its insertion path, or retract the tool and observe the motion of the tool with respect to the vertebra. For some applications, the computer processor automatically virtually advances the tool further along its insertion path, or retracts the tool with respect to the vertebra in the 3D image data.

For some applications, accuracy of determining the position of the portion of the tool within the 3D image data is enhanced by registering three 2D x-ray images to the 3D image data, the images being acquired from respective, different views from one another. Typically, for such applications, an oblique x-ray image view is used in addition to AP and lateral views. For some applications, accuracy of determining the position of the portion of the tool within the 3D image data is enhanced by using x-ray images in which multiple portions of the tool, or portions of multiple tools, are visible and discernible from one another in the x-ray images. For some applications, the tools are discerned from one another based on a manual input by the operator, or automatically by the computer processor. For some applications, accuracy of determining the position of the portion of the tool within the 3D image data is enhanced by referencing the known shapes and/or dimensions of radiopaque markers 52 as described hereinabove.

Figure 24:
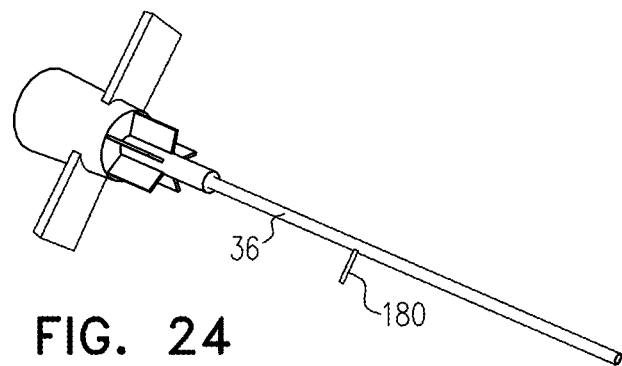
FIG. 24 is a schematic illustration of a Jamshidi™ needle with a radiopaque clip attached thereto, in accordance with some applications of the present invention.

Reference is now made to FIG. 24, which is a schematic illustration of Jamshidi™ needle 36 with a radiopaque clip 180 attached thereto, in accordance with some applications of the present invention. For some applications, accuracy of determining the position of the portion of the tool within the 3D image data is enhanced by adding an additional radiopaque element to the tool (such as clip 180), such that the tool has at least two identifiable features in each 2D image, namely, its distal tip and the additional radiopaque element. For some applications, the additional radiopaque element is configured to be have a defined 3D arrangement such that the additional radiopaque element provides comprehension of the orientation of the tool. For example, the additional radiopaque element may include an array of radiopaque spheres. For some applications, the additional radiopaque element facilitates additional functionalities, e.g., as described hereinbelow. For some applications, the tool itself includes more than one radiopaque feature that is identifiable in each 2D x-ray image. For such applications, an additional radiopaque element (such as clip 180) is typically not attached to the tool.

For some applications, the imaging functionalities described above with reference to the 3D image data are performed with respect to the 2D x-ray images, based upon the co-registration of the 2D images to the 3D image data. For example, the tool may be color-coded in the x-ray images according to how well the tool is placed. For some applications, if the tool is placed incorrectly, the computer processor drives the display to show how the tool should appear when properly placed, within the 2D x-ray images.

Figure 25A:
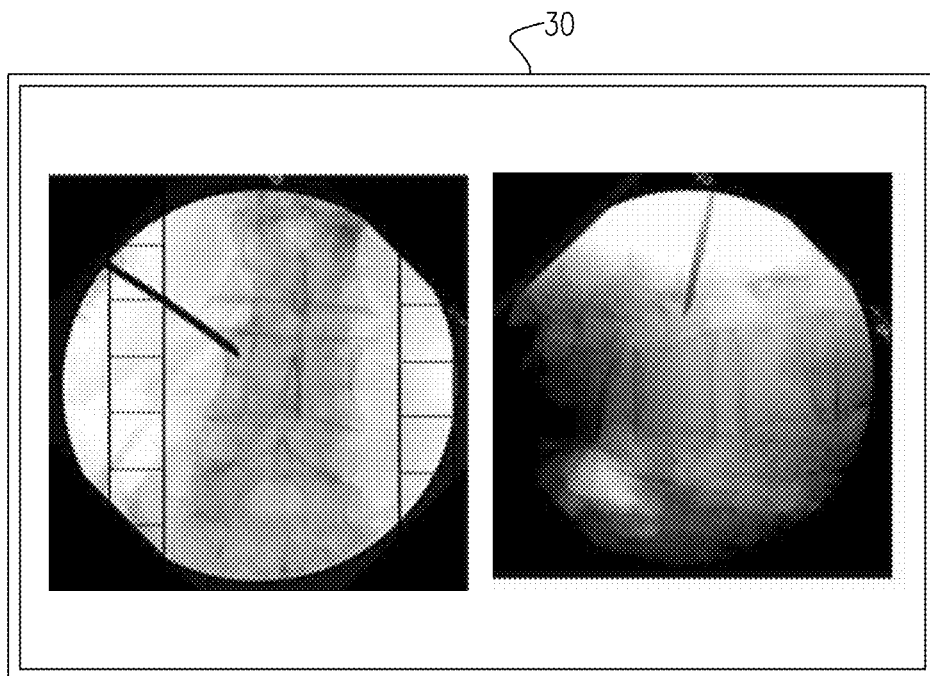
FIG. 25A shows an AP x-ray image and a corresponding lateral x-ray image of a vertebra, at a first stage of the insertion of a tool into the vertebra, in accordance with some applications of the present invention.
Figure 25B:
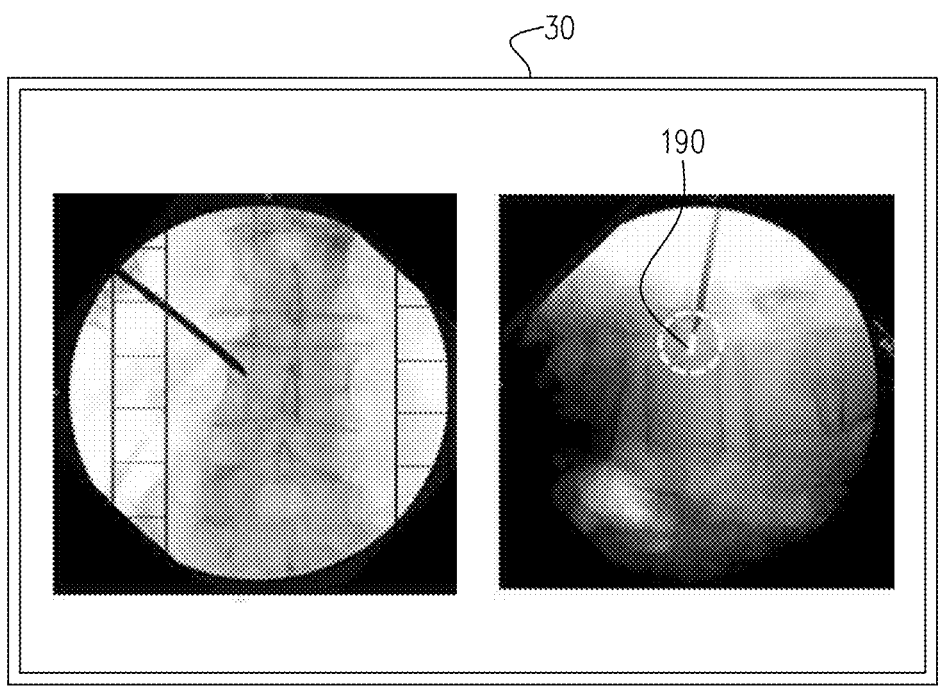
FIG. 25B shows an AP x-ray image of the vertebra, at a second stage of the insertion of the tool into the vertebra, and an indication of the derived current location of the tool tip displayed upon a lateral x-ray image of the vertebra, in accordance with some applications of the present invention.

Reference is now made to FIGS. 25A and 25B, which show examples of AP x-ray images and corresponding lateral x-ray images of a vertebra, at respective stages of the insertion of a tool into the vertebra, in accordance with some applications of the present invention. Reference is also made to step 88 of FIG. 6. A common practice in spinal surgery that is performed under x-ray is to use two separate c-arm poses (typically any two of AP, lateral and oblique) to gain partial 3D comprehension during tool insertion and/or manipulation. This typically requires moving the C-arm back and forth, and exposes the patient to a high radiation dose.

For some applications of the present invention, images are initially acquired from two poses, which correspond to respective image views. For example, FIG. 25A shows examples of AP and lateral x-ray images of a tool being inserted dorsally into a vertebra. Subsequently, the C-arm is maintained at a single pose for repeat acquisitions during tool insertion and/or manipulation, but the computer processor derives the position of the tool with respect to the vertebra in additional x-ray imaging views, and drives the display to display the derived position of the tool with respect to the vertebra in the additional x-ray image views. For example, FIG. 25B shows an example of an AP image of the tool and the vertebra of FIG. 25A, but with the tool having advanced further into the vertebra relative to FIG. 25A. Based upon the AP image in which the tool has advanced the computer processor derives the new, calculated position of the tool with respect to the lateral x-ray imaging view, and drives the display to display a representation 190 of the new tool position upon the lateral image. Typically, the new, calculated tool position is displayed upon the lateral image, in addition to the previously-imaged position of the tool tip within the lateral image, as shown in FIG. 25B. Typically, the computer processor derives the location of portion of the tool with respect to one of the two original 2D x-ray image views, based upon the current location of the portion of the tool as identified within a current 2D x-ray image, and a relationship that is determined between images that were acquired from the two original 2D x-ray image views, as described in further detail hereinbelow.

For some applications, the repeat acquisitions are performed from a 2D x-ray image view that is the same as one of the original 2D x-ray image views, while for some applications the repeat acquisitions are performed from a 2D x-ray image view that is different from both of the original 2D x-ray image views. For some applications, in the subsequent step, the tool within the vertebra is still imaged periodically from one or more additional 2D x-ray image views, in order to verify the accuracy of the position of the tool within the additional views that was derived by the computer processor, and to correct the positioning of the tool within the additional 2D x-ray image views if necessary. For some applications, the C-arm is maintained at a single pose (e.g., AP) for repeat acquisitions during tool insertion and/or manipulation, and the computer processor automatically derives the location of portion of the tool with respect to the 3D image data of the vertebra, and updates the image of the tool (or a representation thereof) within the 3D image data.

Typically, applications as described with reference to FIGS. 25A-B are used with a tool that is inserted into the skeletal anatomy along a longitudinal (i.e., a straight-line, or generally-straight-line) insertion path. For some applications, the techniques are used with a tool that is not inserted into the skeletal anatomy along a straight-line insertion path. For such cases, the computer processor typically determines the non-straight line anticipated path of progress of the tool by analyzing prior progress of the tool, and/or by observing anatomical constraints along the tool insertion path and predicting their effect. For such applications, the algorithms described hereinbelow are modified accordingly.

For some applications, the techniques described with reference to FIGS. 25A-B are performed with respect to a primary x-ray imaging view which is typically from the direction along which the intervention is performed (and typically sets 50 of markers 52 are placed on or near the subject such that the markers appear in this imaging view), and a secondary direction from which images are acquired to provide additional 3D comprehension. In cases in which interventions are performed dorsally, the primary x-ray imaging view is typically generally AP, while the secondary view is typically generally lateral.

For some applications, computer processor 22 uses one of the following algorithms to perform the techniques described with reference to FIGS. 25A-B.

Algorithm 1:
1. The original two 2D x-ray images X1 and X2 are registered to 3D image data using the techniques described hereinabove.
2. Based upon the registration, a generally-straight-line of the tool TL (e.g., the centerline, or tool shaft), as derived from the 2D x-ray images, is positioned with respect to the 3D image data as TL-3D.
3. The generally-straight-line of the tool with respect to the 3D image data is extrapolated to generate a forward line F-TL3D with respect to the 3D image data.
4. When the tool is advanced, a new 2D x-ray X1^ is acquired from one of the prior poses only, e.g., from the same pose from which the original X1 was acquired. (Typically, to avoid moving the C-arm, this is the pose at which the most recent of the two previous 2D x-rays was acquired.)
   For some applications, the computer processor verifies that there has been no motion of the C-arm with respect to the subject, and/or vice versa, between the acquisitions of X1 and X1^, by comparing the appearance of markers 52 in the two images. For some applications, if there has been movement, then Algorithm 2 described hereinbelow is used.
5. The computer processor identifies, by means of image processing, the location of the tool's distal tip in image X1^. This is denoted TPX1^.
6. The computer processor registers 2D x-ray image X1^ to the 3D image data using the DRR that matches the first x-ray view. It is noted that since pose did not change between the acquisitions of X1 and X1^, the DRR that matches x-ray X1^ is same as for x-ray X1. Therefore, there is no need to re-search for the best DRR to match to x-ray X1^.
7. The computer processor draws a line with respect to the 3D image data from C1 through TPX1^.
8. The computer processor identifies the intersection of that line with the F-TL3D line as the new location of the tip, with respect to the 3D image data. It is noted that in cases in which the tool has been retracted, the computer processor identifies the intersection of the line with the straight-line of the tool with respect to the 3D image data TL-3D, rather than with forward line F-TL3D with respect to the 3D image data.
9. The computer processor drives the display to display the tool tip (or a representation thereof) at its new location with respect to the 3D image data, or with respect to x-ray image X2.

Algorithm 2:
1. The original two 2D x-ray images X1 and X2 are registered to 3D image data using the techniques described hereinabove.
2. Based upon the registration, a generally-straight-line TL of the tool (e.g., the centerline, or tool shaft) as derived from the x-ray images is positioned with respect to the 3D image data as TL-3D.
3. The generally-straight-line of the tool with respect to the 3D image data is extrapolated to generate a forward line F-TL3D with respect to the 3D image data.
4. When the tool is advanced, a new 2D x-ray X3 is acquired from, typically, any pose, and not necessarily one of the prior two poses.
5. The computer processor identifies, by means of image processing, the location of the tool's distal tip in image X3. This is denoted TPX3.
6. The computer processor registers 2D x-ray image X3 to the 3D image data of the vertebra by finding a DRR that best matches 2D x-ray image X3, using the techniques described hereinabove. The new DRR has a corresponding simulated camera position C3.
7. The computer processor draws a line with respect to the 3D image data from C3 through TPX3.
8. The computer processor identifies the intersection of that line with the F-TL3D line as the new location of the tip, with respect to the 3D image data. It is noted that in cases in which the tool has been retracted, the computer processor identifies the intersection of the line with the straight-line of the tool with respect to the 3D image data TL-3D, rather than with forward line F-TL3D with respect to the 3D image data.
9. The computer processor drives the display to display the tool tip (or a representation thereof) at its new location with respect to the 3D image data, or with respect to x-ray image X1 and/or X2.

For some applications, Algorithm 1 or Algorithm 2 are further facilitated by adding a radio-opaque feature, for example by means of clipping, typically to the out-of-body portion of the tool. In such cases, a feature, or an identifiable sub-feature thereof, serves as a second feature, in addition to the tool's distal tip, for determining the direction of the tool's shaft. For some applications, the clip, or another radiopaque feature attached to the tool, are as shown in FIG. 24. For some applications, the clip, or another radiopaque feature attached to the tool, improve the accuracy of determining the direction of the tool's shaft.

For some applications, for Algorithm 1 or Algorithm 2, a software algorithm is applied for identifying situations of singularity, with respect to the tool, of X-Ray images X1 and X2. For some applications, such algorithm not only identifies the singularity but also recommends which of X1 and/or X2 should be reacquired from a somewhat different pose. For some applications, such algorithm also guides the user as to what such new pose may be. For some applications, the aforementioned clip, or another radiopaque feature attached to the tool, assists in identifying and/or resolving situations of singularity between x-ray images X1 and X2.

For some applications, the use of Algorithm 1 or Algorithm 2 has an additional benefit of reducing the importance that the X-ray images are acquired in what is known as Ferguson views. In a Ferguson view, the end plates appear as flat and as parallel to one another as possible. It is considered advantageous for proper tool insertion into a vertebra. However, once any acquired 2D x-ray image is co-registered with the 3D CT data, as described by applications of the present invention, and furthermore once a tool seen in the 2D x-ray images is registered with the 3D data, again as described by applications of the present invention, the operator can assess in 3D the correctness of the insertion angle and without needing x-ray images acquired specifically in Ferguson view. Typically, it takes multiple trials-and-errors, when manipulating an x-ray c-arm relative to the subject's body, to achieve Ferguson views. Multiple x-ray images are typically acquired in the process till the desired Ferguson view is achieved, with potential adverse implications on procedure time and the amount of radiation to which the subject and medical staff who are present are exposed.

For some applications, the use of Algorithm 1 or Algorithm 2 has an additional benefit of reducing the importance that the X-ray images are acquired in what is known as "bull's-eye" views. In a "bull's-eye" view, the tool being inserted is viewed from the direction of insertion, ideally with the tool seen only as a cross-section, to further facilitate the surgeon's understanding of where the tool is headed relative to the anatomy. However, once any acquired 2D x-ray image is co-registered with the 3D CT data, as described by applications of the present invention, and furthermore once a tool seen in the 2D x-ray images is registered with the 3D data, again as described by applications of the present invention, the operator can assess in 3D the correctness of the insertion angle and without needing x-ray images acquired specifically in "bull's-eye" view. Typically, it takes multiple trials-and-errors, when manipulating an x-ray c-arm relative to the subject's body, to achieve "bull's-eye" views. Multiple x-ray images are typically acquired in the process till the desired "bull's-eye" view is achieved, with potential adverse implications on procedure time and the amount of radiation to which the subject and medical staff who are present are exposed.

For some applications of the present invention, the operator is assisted in manipulating the c-arm to a Ferguson view prior to activating the c-arm for acquiring images. On the system's display, the vertebra in 3D, with the tool depicted upon it, is rotated to a Ferguson view. Next, the operator manipulates the c-arm such that the tool is positioned relative to the detector at a similar angle to the one depicted on the system's display relative to the operator; only then is the c-arm activated to acquire x-ray images.

Figure 26:
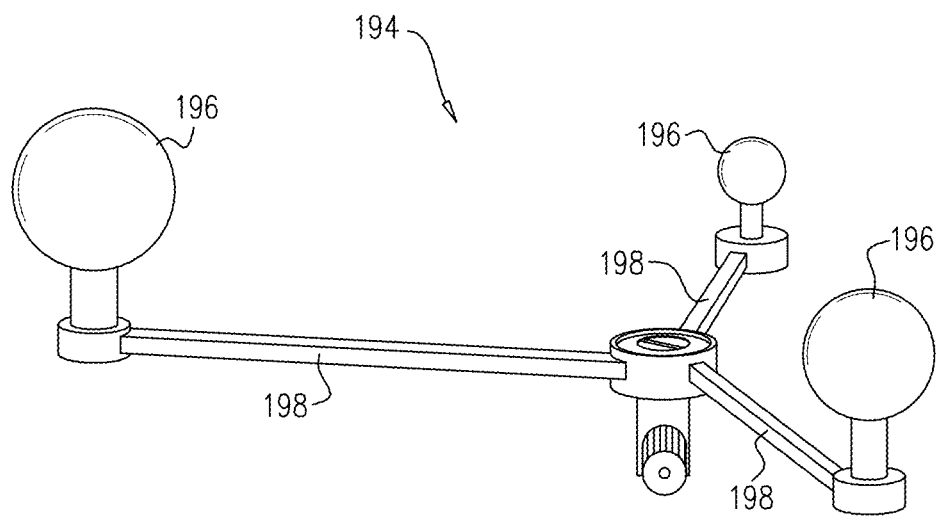
FIG. 26 is a schematic illustration of a three-dimensional rigid jig that comprises at least portions thereof that are radiopaque and function as radiopaque markers, the radiopaque markers being disposed in a predefined three-dimensional arrangement, in accordance with some applications of the present invention.

Algorithm 3:

Reference is now made to FIG. 26, which is a schematic illustration of a three-dimensional rigid jig 194 that comprises at least portions 196 thereof that are radiopaque and function as radiopaque markers, the radiopaque markers being disposed in a predefined three-dimensional arrangement, in accordance with some applications of the present invention. For some applications, as shown, radiopaque portions 196 are radiopaque spheres (which, for some applications, have different sizes to each other, as shown), and the spheres are coupled to one another by arms 198 that are typically radiolucent. Typically, the spheres are coupled to one another via the arms, such that the spatial relationships between the spheres are known precisely.

The following algorithm is typically implemented by computer processor 22 even in cases in which the x-ray images are not registered with 3D image data of the vertebra. Typically, this algorithm is for use with a three-dimensional radiopaque jig, such as jig 194, sufficient portions of which are visible in all applicable x-ray images and can be used to relate them to one another. For some applications, the jig includes a 3D array of radiopaque spheres, as shown in FIG. 20. For example, the jig may be attached to the surgical table.

1. The original two 2D x-ray images X1 and X2 are registered to one another, using markers of the jig as an anchor to provide a 3D reference frame.
2. When the tool is advanced, a new x-ray X1^ is acquired from one of the prior poses, e.g., from the same pose from which the original X1 was acquired. (Typically, to avoid moving the C-arm, this is the pose at which the most recent of the two-previous x-ray was acquired.)
   For some applications, the computer processor verifies that there has been no motion of the C-arm with respect to the subject, and/or vice versa, between the acquisitions of X1 and X1^, by comparing the appearance of markers 52 (typically, relative to the subject's visible skeletal portion), and/or portions 196 of jig 194 (typically, relative to the subject's visible skeletal portion), in the two images. For some applications, if there has been movement, then one of the other algorithms described herein is used.
3. The computer processor identifies, by means of image processing, the location of the tool's distal tip in image X1^. This is denoted TPX1^.
4. The computer processor registers 2D x-ray image X1^ with X2 using the jig.
5. The computer processor calculates the new location of the tool tip upon X2, based upon the registration.
6. The computer processor drives the display to display the tool tip (or a representation thereof) at its new location with respect to x-ray image X2.

Algorithm 4:

The following algorithm is typically implemented by computer processor 22 even in cases in which the x-ray images are not registered with 3D image data of the vertebra. Typically, this algorithm is for use with a tool that has two or more identifiable points in each 2D x-ray image. For example, this algorithm may be used with a tool to which a clip, or another radiopaque feature is attached as shown in FIG. 24.

1. Within the original two 2D x-ray images X1 and X2, the computer processor identifies, by means of image processing, the two identifiable points of the tool, e.g., the distal tip and the clip.
2. The computer processor determines a relationship between X1 and X2, in terms of image pixels. For example:
   a. In X1, the two-dimensional distances between the tool tip and the clip are dx1 pixels horizontally and dy1 pixels vertically.
   b. In X2, the two-dimensional distances between the tool tip and the clip are dx2 pixels horizontally and dy2 pixels vertically
   c. Thus, the computer processor determines a 2D relationship between the two images based upon the ratios dx2:dx1 and dy2:dy1.
3. When the tool is advanced, a new x-ray X1^ is acquired from one of the prior poses, e.g., from the same pose from which the original x-ray X1 was acquired. (Typically, to avoid moving the C-arm, this will be the pose at which the most recent of the previous x-rays was acquired.)
   For some applications, the computer processor verifies that there has been no motion of the C-arm with respect to the subject, and/or vice versa, between the acquisitions of X1 and X1^, by comparing the appearance of markers 52 in the two images. For some applications, if there has been movement, then one of the other algorithms described herein is used.

4. The computer processor identifies, by means of image processing, the tip of the tool in image X1^.
5. The computer processor determines how many pixels the tip has moved between the acquisitions of images X1 and X1^.
6. Based upon the 2D relationship between images X1 and X2, and the number of pixels the tip has moved between the acquisitions of images X1 and X1^, the computer processor determines the new location of the tip of the tool in image X2.
7. The computer processor drives the display to display the tool tip (or a representation thereof) at its new location with respect to x-ray image X2.

With reference to FIGS. 25A and 25B, in general, the scope of the present invention includes acquiring 3D image data of a skeletal portion, and acquiring first and second 2D x-ray images, from respective x-ray image views, of the skeletal portion and a portion of a tool configured to be advanced into the skeletal portion along a longitudinal insertion path, while the portion of the tool is disposed at a first location with respect to the insertion path. The location of a portion of the tool with respect to the skeletal portion is identified within the first and second 2D x-ray images, by computer processor 22 of system 20, by means of image processing, and the computer processor registers the 2D x-ray images to the 3D image data, e.g., using the techniques described herein. Thus, a first location of the portion of the tool with respect to the 3D image data is determined. Subsequently, the tool is advanced along the longitudinal insertion path with respect to the skeletal portion, such that the portion of the tool is disposed at a second location along the longitudinal insertion path. Subsequent to moving the portion of the tool to a second location along the insertion path, one or more additional 2D x-ray images of at least the portion of the tool and the skeletal portion are acquired from a single image view. In accordance with respective applications, the single image view is the same as one of the original 2D x-ray image views, or is a third, different 2D x-ray image view. Computer processor 22 of system 20 identifies the second location of the portion of the tool within the one or more additional 2D x-ray images, by means of image processing, and derives the second location of the portion of the tool with respect to the 3D image data, based upon the second location of the portion of the tool within the one or more additional 2D x-ray images, and the determined first location of the portion of the tool with respect to the 3D image data. Typically, an output is generated in response thereto (e.g., by displaying the derived location of the tool relative to the x-ray image view with respect to which the location has been derived).

In accordance with some applications, first and second 2D x-ray images are acquired, from respective x-ray image views, of the skeletal portion and a portion of a tool configured to be advanced into the skeletal portion along a longitudinal insertion path, while the portion of the tool is disposed at a first location with respect to the insertion path. The location of a portion of the tool with respect to the skeletal portion is identified within the first and second 2D x-ray images, by computer processor 22 of system 20, by means of image processing, and the computer processor determines a relationship between the first and second 2D x-ray images, e.g., using any one of algorithms 1-4 described hereinabove. Subsequently, the tool is advanced along the longitudinal insertion path with respect to the skeletal portion, such that the portion of the tool is disposed at a second location along the longitudinal insertion path. Subsequent to moving the portion of the tool to the second location along the insertion path, one or more additional 2D x-ray images of at least the portion of the tool and the skeletal portion are acquired from a single image view. In accordance with respective applications, the single image view is the same as one of the original 2D x-ray image views, or is a third, different 2D x-ray image view. Computer processor 22 of system 20 identifies the second location of the portion of the tool within the one or more additional 2D x-ray images by means of image processing, and derives the second location of the portion of the tool with respect to one of the original 2D x-ray image views, based upon the second location of the portion of the tool that was identified within the additional 2D x-ray image, and the determined relationship between the first and second 2D x-ray images. Typically, an output is generated in response thereto (e.g., by displaying the derived location of the tool relative to the x-ray image view with respect to which the location has been derived).

Some examples of the applications of the techniques described with reference to FIGS. 25A and 25B are as follows. For an intervention that is performed dorsally, initially x-rays may be acquired from lateral and AP views. Subsequent x-rays may be generally acquired from an AP view only (with optional periodic checks from the lateral view, as described hereinabove), with the updated locations of the tool with respect to the lateral view being derived and displayed. It is noted that although, in this configuration, the C-arm may disturb the intervention, the AP view provides the best indication of the location of the tool relative to the spinal cord. Alternatively, subsequent x-rays may be generally acquired from a lateral view only (with optional periodic checks from the AP view as described hereinabove), with the updated locations of the tool with respect to the AP view being derived and displayed. Typically, for such applications, sets 50 of markers 52 are placed on the patient such that at least one set of markers is visible from the lateral view. Further alternatively, subsequent x-ray may be generally acquired from an oblique view only (with optional periodic checks from the lateral and/or AP view as described hereinabove), with the updated locations of the tool with respect to the AP and/or lateral view being derived and displayed. It is noted that the above applications are presented as examples, and the scope of the present invention includes using the techniques described with reference to FIGS. 25A and 25B with interventions that are performed on any portion of the skeletal anatomy, from any direction of approach, and with any type of x-ray image views, mutatis mutandis.

For some applications, the assumption that the tool, after having been inserted into the vertebra (and typically fixated firmly within the vertebra), has indeed proceeded along an anticipated longitudinal forward path is verified, typically automatically. Consecutive x-ray images acquired from a same pose are overlaid upon one another to check whether, when the images are positioned such that a position of the tool as seen in a second image is longitudinally aligned with a prior position of the same tool in a first image, the observed anatomies in both images indeed overlap with one another. Or, alternatively, when the images are positioned such that the observed anatomies in both images overlap with one another, the position of the tool as seen in a second image is indeed longitudinally aligned with a prior position of the same tool in a first image. For some applications, the motion detection sensor described by the present application is used for verifying that no motion (or no motion above a certain threshold) of the subject has occurred during the acquisition of the subsequent images. For some applications, comparison of the alignment is manual (visual) by the user, or automatic (by means of image processing), or any combination thereof.

Figures 27A, 27B:
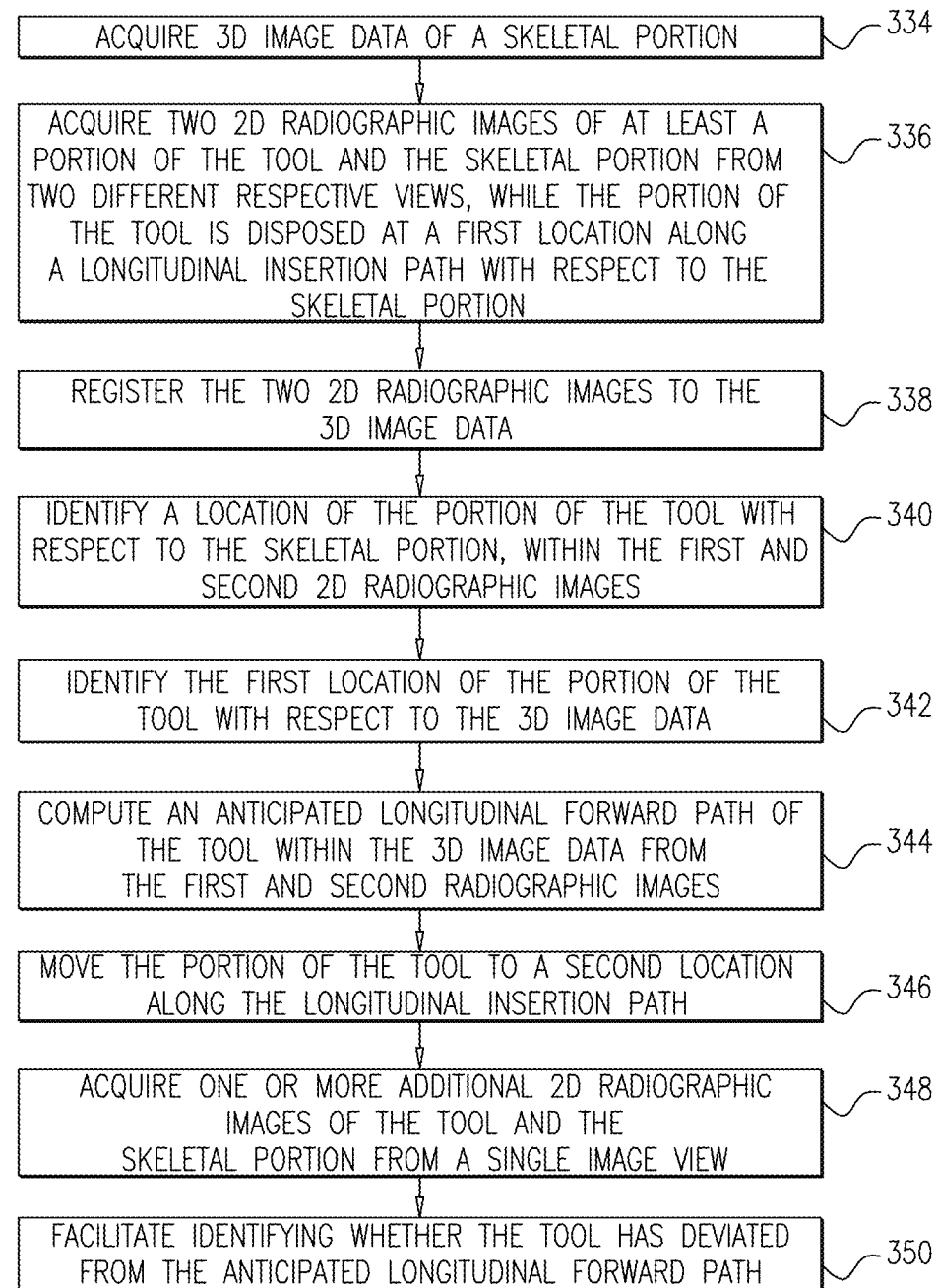
FIGS. 27A and 27B are flowcharts for a method for verifying if the tool has indeed proceeded along an anticipated longitudinal path, in accordance with some applications of the present invention.
Figure 28A:
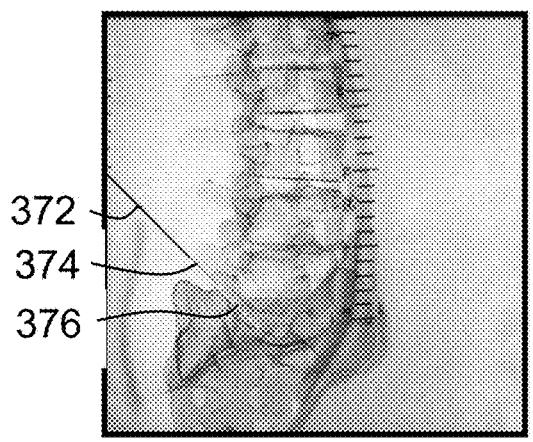
FIGS. 28A-E show an example of a tool bending during its insertion, with the bending becoming increasingly visible (manually) or identifiable (automatically), in accordance with some applications of the present invention.
Figure 28B:
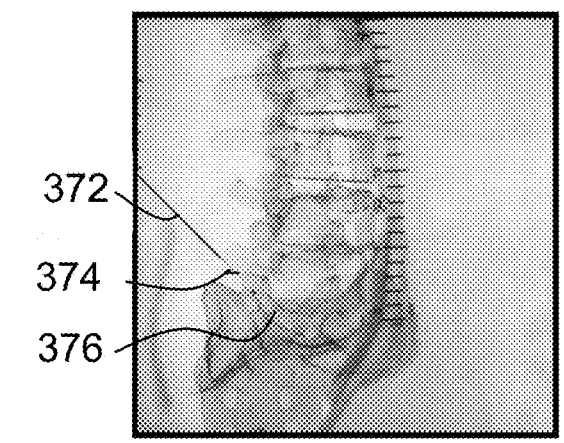
Figure 28C:
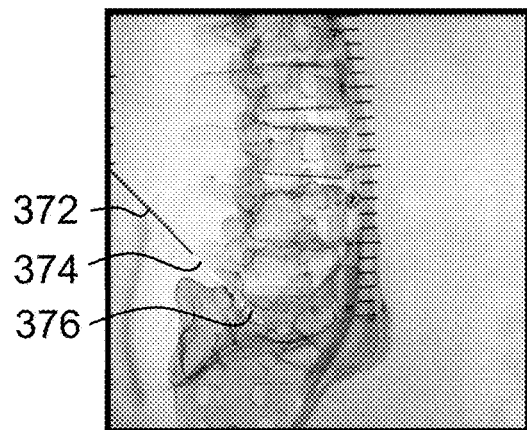
Figure 28D:
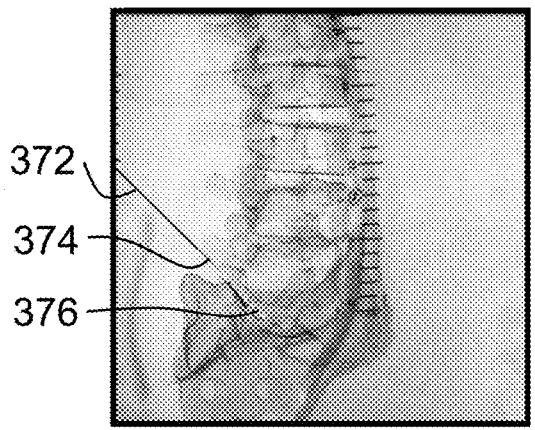
Figure 28E:
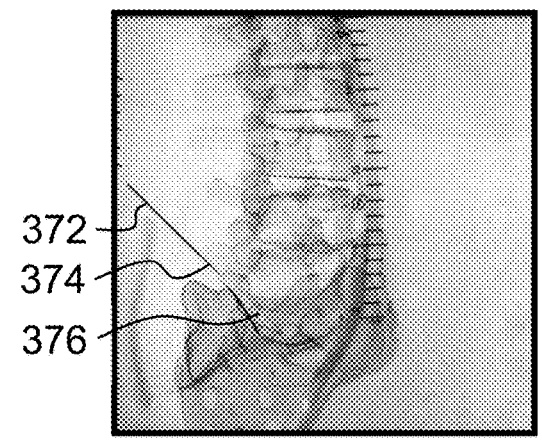

Reference is now made to FIGS. 27A-B, which show flowcharts for a method for verifying if the tool has indeed proceeded along an anticipated longitudinal path, in accordance with some applications of the present invention. For some applications, the assumption that once the tool was inserted into the vertebra (and typically fixated firmly) it has indeed proceeded along an anticipated longitudinal path is verified, typically automatically, as follows:

1. 3D image data is acquired of the skeletal portion, e.g., vertebra (step 334).
2. The anticipated longitudinal forward path of the tool is computed within the 3D image data (step 344) from two x-ray images (i) acquired (typically using an x-ray imaging device that is unregistered with respect to the body of the subject) from different views while the tool is in the same position, i.e., at a first location along the longitudinal insertion path of the tool (step 336), (ii) registered with the 3D scan data, using techniques disclosed by the present application (step 338), and (iii) in each of which a location of the portion of the tool with respect to the skeletal portion is identified (step 340), such that the first location of the portion of the tool is identified with respect to the 3D image data (step 342).
3. The tool is moved further, typically forward, to a second location along the longitudinal insertion path (step 346).
4. One or more additional x-ray images is acquired (from any view, not necessarily from one of the two prior views, see Algorithm 1 and Algorithm 2 of the 2D-3D registration) (step 348).
5. With reference to FIG. 27B, computer processor 22 is used to facilitate identifying whether the tool has deviated from the anticipated longitudinal forward path (step 350 of FIG. 27A) as follows:
6. The newly-acquired x-ray image is registered with the 3D scan data within which the anticipated longitudinal progression, i.e., forward, path has been computed (step 352).
7. The anticipated longitudinal progression path now becomes registered with the newly-acquired, i.e., additional one or more, x-ray image; optionally, it may now be shown on the newly-acquired x-ray image.
8. In the newly-acquired x-ray image, the actual tool, and particularly the distal portion thereof, is identified (step 354) and may be compared with the anticipated longitudinal progression path to identify whether the tool has deviated from the anticipated longitudinal forward, e.g., progression, path. For some applications, the comparison is manual (visual) by the user, or automatic by the system (typically by means of image processing), or any combination thereof (It should be noted that such comparison is typically only in the imaging plane of the x-ray system.)
9. For some applications, if a significant difference (which may also be defined as above a certain threshold) between the actual distal portion of the tool and the anticipated longitudinal progression path has been identified manually (visually) by the user, or automatically (in pixels, or in absolute distance, by means of image processing) by the system, then the anticipated longitudinal progression path may be recalculated by moving the x-ray source into a substantially different viewing position, without moving the tool, acquiring another x-ray image, and have the system recalculate the anticipated longitudinal progression path using the two most recently acquired x-ray images (i.e., the x-ray image just acquired from the substantially different viewing position and the additional x-ray image acquired in step 348).

Reference is now made to FIGS. 28A-E, which show an example of a tool bending during its insertion, with the bending becoming increasingly visible (manually) or identifiable (automatically). (The black line 372 is the tool in the x-ray, the solid white line 374 is the anticipated longitudinal progression path where it still matches the actual tool, and the dashed white line 376 is where the tool becomes further away from the anticipated longitudinal progression path. Solid white line 374 and dashed white line 376 are in some embodiments generated by the system. In some embodiments, there is only one white line not broken into a solid section and a dashed section.)

For some applications, the image of the tool (a representation thereof, and/or a path thereof) as derived from the 2D images is overlaid upon the 3D image data of the vertebra as a hologram. As noted hereinabove, since, in accordance with such applications, the images of the vertebra and the tool (or a representation thereof) are input from different imaging sources, the segmented data of what is the tool (or its representation) and what is the vertebra is in-built (i.e., it is already known to the computer processor). For some applications, the computer processor utilizes this in-built segmentation to allow the operator to virtually manipulate the tool with respect to the vertebra, within the hologram. For example, the operator may virtually advance the tool further along its insertion path, or retract the tool and observe the motion of the tool with respect to the vertebra. Or, the computer processor may automatically drive the holographic display to virtually advance the tool further along its insertion path, or retract the tool. For some applications, similar techniques are applied to other tools and bodily organs, mutatis mutandis. For example, such techniques could be applied to a CT image of the heart in combination with 2D angiographic images of a catheter within the heart.

For some applications, an optical camera is used to acquire optical images of a tool. For example, optical camera 114, which is disposed on x-ray C-arm 34, as shown in FIG. 1, may be used. Alternatively or additionally, an optical camera may be disposed on a separate arm, may be handheld, may be the back camera of a display such as a tablet or mini-tablet device, may be placed on the surgeon's head, may be placed on another portion of the surgeon's body, and/or may be held by another member of the surgical staff. Typically, the computer processor derives the location of the tool with respect to the 3D image data, based upon 2D images in which the tool was observed and using the registration techniques described hereinabove. For some applications, in addition, the computer processor identifies the tool within an optical image acquired by the optical camera. For some such applications, the computer processor then overlays the 3D image data upon the optical image by aligning the location of the tool within the 3D image data and the location of the tool within the optical image. The computer processor then drives an augmented reality display to display the 3D image data overlaid upon the optical image. Such a technique may be performed using any viewing direction of the optical camera within which the tool is visible, and typically without having to track the position of the subject with respect to the optical camera.

For some applications, the location of the tool within the optical image space is determined by using two or more optical cameras, and/or one or more 3D optical cameras. For some applications, even with one 2D optical camera, the 3D image data is overlaid upon the optical image, by aligning two or more tools from each of the imaging modalities. For some applications, even with one 2D optical camera and a single tool, the 3D image data is overlaid upon the optical image, by acquiring additional information regarding the orientation (e.g., rotation) of the tool, and/or the depth of the tool below the skin. For some applications, such information is derived from 3D image data from which the location of the skin surface relative to the vertebra is derived. Alternatively or additionally, such information is derived from an x-ray image in which the tool and the subject's anatomy are visible. Alternatively or additionally, such information is derived from the marker set as seen in an x-ray image in which the tool and the subject's anatomy are visible.

As noted hereinabove, since the images of the vertebra and the tool (or a representation thereof) are input from different imaging sources, the segmented data of what is the tool (or its representation) and what is the vertebra is in-built (i.e., it is already known to the computer processor). For some applications, the computer processor utilizes this in-built segmentation to allow the operator to virtually manipulate the tool with respect to the vertebra, within an augmented reality display. For example, the operator may virtually advance the tool further along its insertion path, or retract the tool and observe the motion of the tool with respect to the vertebra. Or, the computer processor may automatically drive the augmented reality display to virtually advance the tool further along its insertion path, or retract the tool.

Although some applications of the present invention have been described with reference to 3D CT image data, the scope of the present invention includes applying the described techniques to 3D MRI image data. For such applications, 2D projection images (which are geometrically analogous to DRRs that are generated from CT images) are typically generated from the MRI image data and are matched to the 2D images, using the techniques described hereinabove. For some applications, other techniques are used for registering MRI image data to 2D x-ray images. For example, pseudo-CT image data may be generated from the MRI image data (e.g., using techniques as described in "Registration of 2D x-ray images to 3D MRI by generating pseudo-CT data" by van der Bom et al., Physics in Medicine and Biology, Volume 56, Number 4), and the DRRs that are generated from the pseudo-CT data may be matched to the x-ray images, using the techniques described hereinabove.

For some applications, MRI imaging is used during spinal endoscopy, and the techniques described herein (including any one of the steps described with respect to FIG. 6) are used to facilitate performance of the spinal endoscopy. Spinal endoscopy is an emerging procedure that is used, for example, in spinal decompression. By using an endoscope, typically, tools can be inserted and manipulated via a smaller incision relative to current comparable surgery that is used for similar purposes, such that a smaller entry space provides a larger treatment space than in traditional procedures. Typically, such procedures are used for interventions on soft tissue, such as discs. Such tissue is typically visible in MRI images, but is less, or not at all, visible in CT images or in 2D x-ray images. Traditionally, such procedures commence with needle insertion under C-Arm imaging. A series of dilators are then inserted to gradually broaden the approach path. Eventually, an outer tube having a diameter of approximately 1 cm is then kept in place and an endoscope is inserted therethrough. From this point on, the procedure is performed under endoscopic vision.

For some applications, level verification as described hereinabove is applied to a spinal endoscopy procedure in order to determine the location of the vertebra with respect to which the spinal endoscopy is to be performed. Alternatively or additionally, the incision site for the spinal endoscopy may be determined using bidirectional mapping of optical images and x-ray images, as described hereinabove. Alternatively or additionally, planning of the insertion may be performed upon the 3D MRI data as described hereinabove. Alternatively or additionally, actual insertion vs. the planned path may be represented upon the 3D MRI data as described hereinabove. Alternatively or additionally, actual insertion vs. the planned path may be represented upon a 2D x-ray image as described hereinabove. For some applications, MRI image data are registered to intraprocedural 2D x-ray images. Based upon the registration, additional steps which are generally as described hereinabove are performed. For example, the needle, dilator, and/or endoscope (and/or a representation thereof, and/or a path thereof) may be displayed relative to a target within the MRI image data (e.g., a 3D MRI image, a 2D cross-section derived from 3D MRI image data, and/or a 2D projection image derived from 3D MRI image data). For some applications, endoscopic image data are co-registered to intraprocedural 2D x-ray images. For example, respective endoscopic image data points may be co-registered with respective locations within the intraprocedural images. For some applications, the co-registered endoscopic image data are displayed with the intraprocedural images, together with an indication of the co-registration of respective endoscopic image data points with respective locations within the intraprocedural images. Alternatively or additionally, endoscopic image data are co-registered to MRI image data. For example, respective endoscopic image data points may be co-registered with respective locations within the MRI image data. For some applications, the co-registered endoscopic image data are displayed with the MRI image data, together with an indication of the co-registration of respective endoscopic image data points with respective locations within the MRI image data.

For some applications, the techniques described herein are performed in combination with using a robotic arm, such as a relatively low-cost robotic arm having 5-6 degrees of freedom. In accordance with some applications, the robotic arm is used for holding, manipulating, and/or activating a tool, and/or for operating the tool along a pre-programmed path. For some applications, computer processor 22 drives the robotic arm to perform any one of the aforementioned operations responsively to imaging data, as described hereinabove.

Figure 29A:
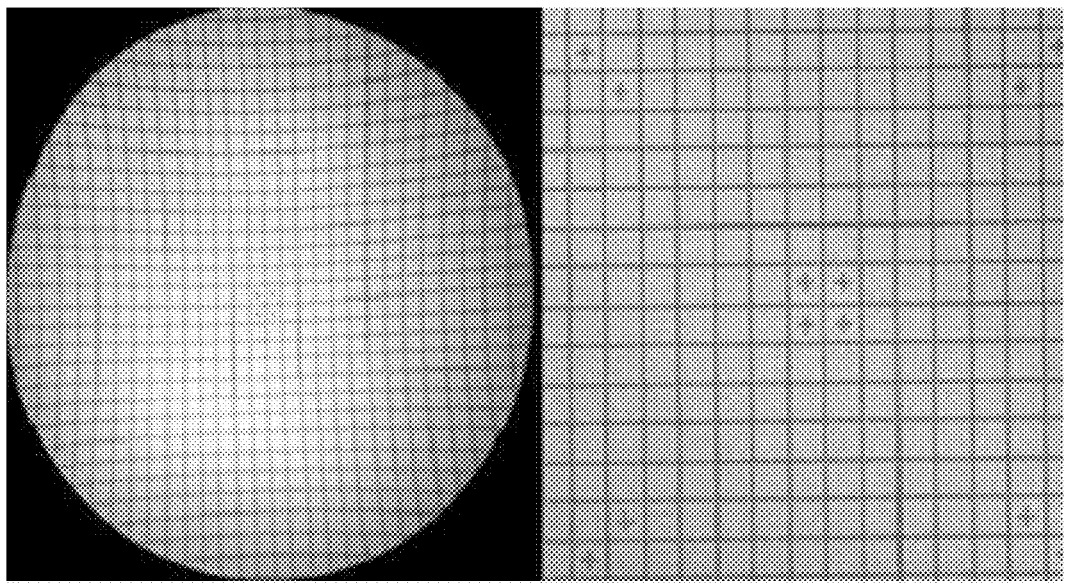
FIG. 29A show examples of x-ray images of a calibration jig generated by a C-arm that uses an image intensifier, and by a C-arm that uses a flat-panel detector, such images reflecting prior art techniques.
Figure 29B:
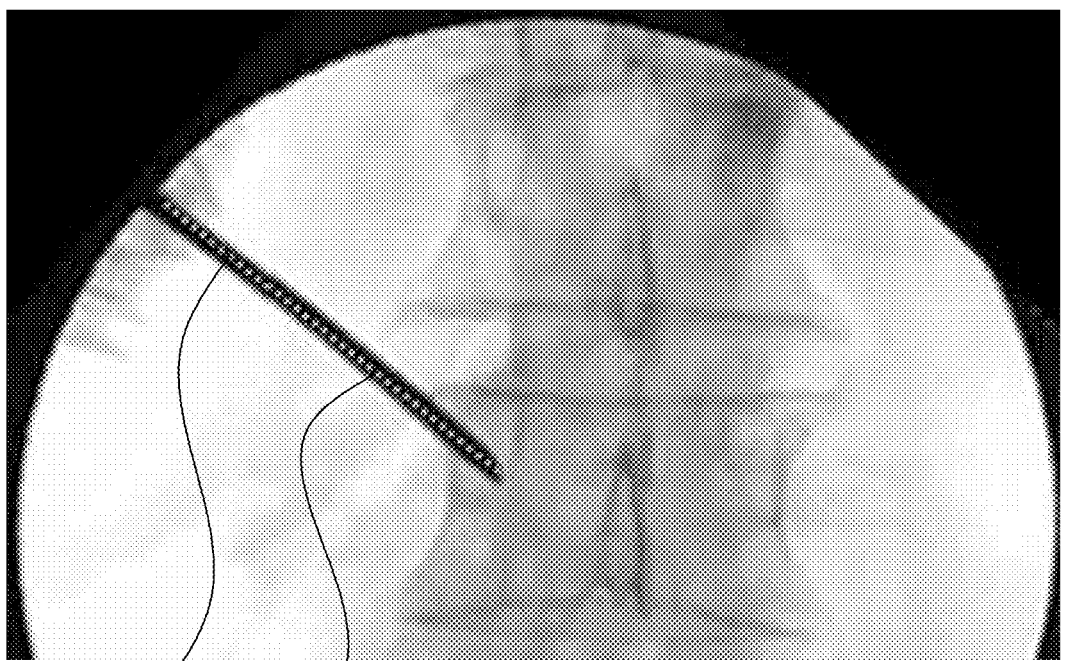
FIG. 29B shows an example of an x-ray image acquired by a C-arm that uses an image intensifier, the image including a radiopaque component that corresponds to a portion of a tool that is known to be straight, and a dotted line overlaid upon the image indicating how a line defined by the straight portion would appear if distortions in the image are corrected, in accordance with some applications of the present invention.

Reference is now made to FIG. 29A, which shows examples of x-ray images of an image calibration jig generated by a C-arm that uses an image intensifier (on the left), and by a C-arm that uses a flat-panel detector (on the right), such images reflecting prior art techniques. Reference is also made to FIG. 29B, which shows an example of an x-ray image acquired by a C-arm that uses an image intensifier, the image including a radiopaque component 200 that corresponds to a portion of a tool that is known to be straight, and a dotted line 210 overlaid upon the image indicating how a line (for example, a centerline) defined by the straight portion would appear if distortions in the image are corrected, in accordance with some applications of the present invention.

As may be observed in the example shown in FIG. 29A, in x-ray images generated by a C-Arm that uses an image intensifier, there is typically image distortion, which increases toward the periphery of the image. By contrast, in images generated using a flat-panel detector, there is typically no distortion. For some applications of the present invention, distortions in x-ray images generated by a C-Arm that uses an image intensifier are at least partially corrected automatically, by means of image processing. For example, the distortion of such images may be corrected in order to then register the corrected image to a 3D image data, using the techniques described hereinabove.

Referring to FIG. 29B, for some applications such an x-ray image is at least partially corrected by computer processor 22 identifying, by means of image processing, a radiopaque component 200 of an instrument within a portion of the radiographic image. For some applications, the radiopaque component is a portion of the tool that is known to be straight, a component having a different known shape, and/or two or more features that are disposed in known arrangement with respect to one another. For example, the straight shaft of a Jamshidi™ needle may be identified.

For some applications, in order to at least partially correct an x-ray image comprising a radiopaque component that is known to be straight, the computer processor uses techniques for automatically identifying a centerline of an object, for example, as described in US 2010-0161022 to Tolkowsky, which is incorporated herein by reference, to generate a centerline of said component. Typically, the computer processor then at least partially corrects the image distortion, in at least a portion of the image in which the component that is known to be straight is disposed, by deforming the portion of the radiographic image, such that the centerline of the radiopaque component of the instrument that is known to be straight appears straight within the radiographic image. FIG. 29B shows an example of how an x-ray image, prior to correcting its distortion, comprises component 200 that is known to be straight and yet does not appear straight within the image, as can be observed relative to straight line 210. For some applications, two or more such components are identified in respective portions of the image, and distortion of those portions of the image are corrected accordingly. For some applications, distortions in portions of the image in which no such components are disposed are corrected, based upon distortion correction parameters that are determined by means of the radiopaque component that is known to be straight, or known to have a different known shape.

For some applications of the present invention, techniques described hereinabove are combined with a system that determines the location of the tip of a tool with respect to a portion of the subject's body by (a) calculating a location of a proximal portion of the tool that is disposed outside the subject's body, and (b) based upon the calculated position of the proximal portion of the tool, deriving a location of a tip of the tool with respect to the portion of the subject's body with respect to the 3D image data. For example, such techniques may be used with a navigation system that, for example, may include the use of one or more location sensors that are attached to a portion of a tool that is typically disposed outside the subject's body even during the procedure. (It is noted that the location sensors that are disposed upon the tool may be sensors that are tracked by a tracker that is disposed elsewhere, or they may be a tracker that tracks sensors that are disposed elsewhere, and thereby acts a location sensor of the tool.) For example, a tool may be inserted into the subject's vertebra, such that its distal tip (or a distal portion of the tool) is disposed inside the vertebra, and a location sensor may be disposed on a proximal portion of the tool that is disposed outside the subject's body. The navigation system typically derives the location of the tip of the tool (or a distal portion of the tool), by detecting the location(s) of the location sensor(s) that are disposed on the proximal portion of the tool, and then deriving the location of the tip of the tool (or a distal portion of the tool) based upon an assumed location of the distal tip of the tool (or a distal portion of the tool) relative to the location sensor(s). The navigation system then overlays the derived location of the tip of the tip of the tool (or a distal portion of the tool) with respect to the vertebra upon previously acquired 3D image data (e.g., images acquired prior to the subject being placed in the operating room, or when the subject was in the operating room, but typically prior to the commencement of the intervention). Alternatively or additionally, the location of a proximal portion of the tool that is disposed outside the subject's body may be calculated by video tracking the proximal portion of the tool, and/or by means of tracking motion of a portion of a robot to which the proximal portion of the tool is coupled, relative to a prior known position, e.g., based upon the values of the joints of the robot relative to the corresponding values of the joints of the robot at the prior known position.

In such cases, there may be errors associated with determining the location of the tip of the tool (or a distal portion of the tool), based upon the assumed location of the distal tip of the tool (or a distal portion of the tool) relative to the location sensor(s) being erroneous, e.g., due to slight bending of the tool upon being inserted into the vertebra. Therefore, for some applications, during the procedure, typically periodically, 2D x-ray images are acquired within which the actual tip of tool (or distal portion of the tool) within the vertebra is visible. The location of the tip of the tool (or distal portion of the tool) with respect to the vertebra as observed in the 2D x-ray images is determined with respect to the 3D image data, by registering the 2D x-ray images to the 3D image data. For example, the 2D x-ray images may be registered to the 3D image data using techniques described hereinabove. In this manner, the actual location of the tip of the tool (or distal portion of the tool) with respect to the vertebra is determined with respect to the 3D image data. For some applications, in response thereto, errors in the determination of the location of the tip of the tool (or distal portion of the tool) with respect to the vertebra within the 3D image space resulting from the navigation system, are periodically corrected by system 20. For example, based upon the determined location of at least the tip of the tool (or distal portion of the tool), the computer processor may drive the display to update the indication of the location of the tip of the tool (or distal portion of the tool) with respect to the vertebra with respect to the 3D image data. For some applications, the navigation systems comprise the use of augmented reality, or virtual reality, or robotic manipulation of tools, or any combination thereof.

By way of illustration and not limitation, it is noted that the scope of the present invention includes applying the apparatus and methods described herein to any one of the following applications:

Multiple tool insertions (e.g., towards both pedicles) in the same vertebra.

Any type of medical tool or implant, including, Jamshidi™ needles, k-wires, pedicle markers, screws, endoscopes, RF probes, laser probes, injection needles, etc.

An intervention that is performed from a lateral approach, in which case the functional roles of the AP and lateral x-ray views described hereinabove are typically switched with one another.

Interventions using x-ray views other than lateral and AP views as an alternative or in addition to such views. For example, oblique imaging views may be used.

An intervention that is performed from an anterior, oblique and/or posterior interventional approach.

Interventions performed upon multiple vertebrae. Even for such cases, the intra-operative x-ray images of the vertebrae are typically registered with the 3D image data of the corresponding vertebrae on an individual basis.

Interventions performed on discs in between vertebrae.

Interventions performed on nerves.

Tool insertion under x-ray in a video imaging mode.

Use of certain features of system 20 utilizing intraprocedural 2D x-ray imaging, but without utilizing preprocedural 3D imaging.

Use of certain features of system 20 without some or all of the above-described disposable items, such as a drape.

Various orthopedic surgeries, such as surgeries performed on limbs and/or joints.

Interventions in other body organs.

For some applications system 20 includes additional functionalities to those described hereinabove. For example, the computer processor may generate an output that is indicative of a current level of accuracy (e.g., of verification of the vertebral level, determination of the insertion site, and/or registration of the 3D image data to the 2D images), e.g., based upon a statistical calculation of the possible error. For some applications, the computer processor generates a prompt indicating that a new x-ray from one or more views should be acquired. For example, the computer processor may generate such a prompt based on the time elapsed since a previous x-ray acquisition from a given view, and/or based on the distance a tool has moved since a previous x-ray acquisition from a given view, and/or based on observed changes in the position of markers 52 relative to the C-arm.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 22. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 22) coupled directly or indirectly to memory elements (such as memory 24) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that blocks of the flowchart shown in FIGS. 7, 14A, and 14B, combinations of blocks in the flowcharts, as well as any one of the algorithms described herein, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 22) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 22 and the other computer processors described herein are typically hardware devices programmed with computer program instructions to produce a special purpose computer. For example, when programmed to perform the algorithms described herein, the computer processor typically acts as a special purpose skeletal-surgery-assisting computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for performing a procedure using a tool configured to be advanced into a skeletal portion within a body of a subject along a longitudinal insertion path, the method comprising:
   acquiring 3D image data of the skeletal portion;
   while a portion of the tool is disposed at a first location along the longitudinal insertion path with respect to the skeletal portion, sequentially:
   1. acquiring a first 2D x-ray image of at least the portion of the tool and the skeletal portion from a first view, using a 2D x-ray imaging device that is disposed at a first pose with respect to the subject's body;
   2. moving the 2D x-ray imaging device to a second pose with respect to the subject's body; and
   3. while the 2D x-ray imaging device is at the second pose, acquiring a second 2D x-ray image of at least the portion of the tool and the skeletal portion from a second view; using at least one computer processor:
   registering the first and second 2D x-ray images to the 3D image data;
   identifying a location of the portion of the tool with respect to the skeletal portion, within the first and second 2D x-ray images,
   based upon (a) the identified location of the portion of the tool within the first and second 2D x-ray images, and (b) the registration of the first and second 2D x-ray images to the 3D image data, identifying the first location of the portion of the tool with respect to the 3D image data; and
   computing an anticipated longitudinal forward path of the tool within the 3D image data based on the first and second 2D x-ray images;
   subsequently, moving the portion of the tool to a second location along the longitudinal insertion path with respect to the skeletal portion;
   subsequent to moving the portion of the tool to the second location, acquiring one or more additional 2D x-ray images of at least the portion of the tool and the skeletal portion from a single image view; and
   using the computer processor, facilitating identifying whether or not the tool has deviated from the anticipated longitudinal forward path by:
   registering the additional one or more 2D x-ray images to the 3D image data, such that the anticipated longitudinal forward path of the tool is registered with the additional one or more 2D x-ray images, and
   identifying a location of the portion of the tool with respect to the skeletal portion, within the additional one or more 2D x-ray images.

2. The method according to claim 1, wherein acquiring one or more of the x-ray images selected from the group consisting of: the first 2D x-ray image of at least the portion of the tool and the skeletal portion from the first view, the second 2D x-ray image of at least the portion of the tool and the skeletal portion from the second view, and the one or more additional x-ray images, comprises using a 2D x-ray imaging device that is unregistered with respect to the body of the subject.

3. The method according to claim 1, further comprising, using the computer processor, subsequently to registering the additional one or more 2D x-ray images to the 3D image data, overlaying the anticipated longitudinal forward path of the tool on the additional one or more 2D x-ray images.

4. The method according to claim 3, wherein identifying whether the tool has deviated from the anticipated longitudinal forward path comprises comparing a position of the tool in the one or more additional 2D x-ray images with the anticipated longitudinal forward path overlayed on the one or more additional 2D x-ray images.

5. The method according to claim 4, wherein comparing the position of the tool in the one or more additional 2D x-ray images with the anticipated longitudinal forward path overlayed on the one or more additional 2D x-ray images comprises comparing a position of a distal portion of the tool in the one or more additional 2D x-ray images with the anticipated longitudinal forward path overlayed on the one or more additional 2D x-ray images.

6. The method according to claim 4, wherein comparing the position of the tool in the one or more additional 2D x-ray images with the anticipated longitudinal forward path overlayed on the one or more additional 2D x-ray images comprises:
   (a) a user visually comparing the position of the tool in the one or more additional 2D x-ray images with the anticipated longitudinal forward path overlayed on the one or more additional 2D x-ray images, or
   (b) using the at least one computer processor, comparing the position of the tool in the one or more additional 2D x-ray images with the anticipated longitudinal forward path overlayed on the one or more additional 2D x-ray images, or
   (c) a combination of (a) and (b).

7. The method according to claim 6, wherein using the at least one computer processor, comparing the position of the tool in the one or more additional 2D x-ray images with the anticipated longitudinal forward path overlayed on the one or more additional 2D x-ray images comprises comparing the position of the tool in the one or more additional 2D x-ray images with the anticipated longitudinal forward path overlayed on the one or more additional 2D x-ray images by means of image processing.

8. The method according to claim 1, wherein acquiring one or more additional 2D x-ray images of at least the portion of the tool and the skeletal portion from the single image view comprises acquiring one or more additional 2D x-ray images from either the first view or the second view.

9. The method according to claim 1, wherein acquiring one or more additional 2D x-ray images of at least the portion of the tool and the skeletal portion from the single image view comprises acquiring one or more additional 2D x-ray images from an image view other than the first view or the second view.

10. The method according to claim 1, wherein registering the first and second 2D x-ray images to the 3D image data comprises:
    generating a plurality of 2D projections from the 3D image data, and
    identifying respective first and second 2D projections that match the first and second 2D x-ray images of the skeletal portion.

11. The method according to claim 10, wherein the identifying of the respective first and second ones of the 2D projections that match the first and second 2D x-ray images of the skeletal portion is performed using a machine learning technique.

12. The method according to claim 1, wherein registering the first and second 2D x-ray images to the 3D image data comprises registering the first and second 2D x-ray images to the 3D image data using a machine learning technique.

13. The method according to claim 1, wherein identifying the location of the portion of the tool with respect to the skeletal portion, within the first and second 2D x-ray images, comprises identifying the location of the portion of the tool with respect to the skeletal portion, within the first and second 2D x-ray images, by means of image processing.

14. The method according to claim 1, wherein identifying a location of the portion of the tool with respect to the skeletal portion, within the additional one or more 2D x-ray images, comprises identifying a location of the portion of the tool with respect to the skeletal portion, within the one or more additional 2D x-ray images, by means of image processing.

15. The method according to claim 1, wherein the method further comprises, in response to an identification that the tool has deviated from the anticipated longitudinal forward path by more than a threshold amount:
moving the 2D x-ray imaging device to an image view that is different from the single image view,
without moving the tool, acquiring another 2D x-ray image of at least the portion of the tool and the skeletal portion from the different image view, and
using the at least one computer processor, recalculating the anticipated longitudinal forward path based on the another 2D x-ray image and the one or more additional 2D x-ray images.

16. Apparatus for performing a procedure in which a tool is advanced into a skeletal portion within a body of a subject along a longitudinal insertion path, and for use with:
(i) a 3D imaging device configured to acquire 3D image data of the skeletal portion; and
(ii) a 2D x-ray imaging device that is configured to:
(a) while a portion of the tool is disposed at a first location along the longitudinal insertion path with respect to the skeletal portion, sequentially:
while the 2D x-ray imaging device is disposed at a first pose with respect to the subject's body, acquire a first 2D x-ray image of at least the portion of the tool and the skeletal portion from a first view;
be moved to a second pose with respect to the subject's body, and
while the 2D x-ray imaging device is at the second pose, acquire a second 2D x-ray image of at least the portion of the tool and the skeletal portion from a second view, and
(b) subsequent to the portion of the tool being moved to a second location along the longitudinal insertion path with respect to the skeletal portion, acquire one or more additional 2D x-ray images from a single image view, the apparatus comprising:
at least one computer processor configured to:
(a) receive from the 3D imaging device the 3D image data;
(b) receive from the 2D x-ray imaging device the first and second 2D x-ray images of at least the portion of the tool and the skeletal portion;
(c) register the first and second 2D x-ray images to the 3D image data;
(d) identify a location of the portion of the tool with respect to the skeletal portion, within the first and second 2D x-ray images;
(e) based upon the identified location of the portion of the tool within the first and second 2D x-ray images, and the registration of the first and second 2D x-ray images to the 3D image data, identify the first location of the portion of the tool with respect to the 3D image data,
(f) compute an anticipated longitudinal forward path of the tool within the 3D image data based on the first and second 2D x-ray images;
(g) receive from the 2D x-ray imaging device the one or more additional 2D x-ray images of at least the portion of the tool and the skeletal portion; and
(h) facilitate identifying whether the tool has deviated from the anticipated longitudinal forward path by:
registering the additional one or more 2D x-ray images to the 3D image data, such that the anticipated longitudinal forward path of the tool is registered with the additional one or more 2D x-ray images, and
identifying a location of the portion of the tool with respect to the skeletal portion, within the additional one or more 2D x-ray images.

17. The apparatus according to claim 16, wherein:
the at least one computer processor is further configured to, subsequent to registering the one or more additional 2D x-ray images to the 3D image data, overlay the anticipated forward path of the tool on the one or more additional 2D x-ray images,
identifying whether the tool has deviated from the anticipated longitudinal forward path comprises comparing a position of the tool in the one or more additional 2D x-ray images with the anticipated longitudinal forward path overlayed on the one or more additional 2D x-ray images, the comparing comprising:
(a) a user visually comparing the position of the tool in the one or more additional 2D x-ray images with the anticipated longitudinal forward path overlayed on the one or more additional 2D x-ray images, or
(b) the at least one computer processor comparing the position of the tool in the one or more additional 2D x-ray images with the anticipated longitudinal forward path overlayed on the one or more additional 2D x-ray images, or
(c) a combination of (a) and (b).

18. A non-transitory computer software product for facilitating performing a procedure in which a tool is advanced into a skeletal portion within a body of a subject along a longitudinal insertion path, the non-transitory computer software product for use with:
(i) a 3D imaging device configured to acquire 3D image data of the skeletal portion; and
(ii) a 2D x-ray imaging device that is configured to:
(a) while a portion of the tool is disposed at a first location along the longitudinal insertion path with respect to the skeletal portion, sequentially:
while the 2D x-ray imaging device is disposed at a first pose with respect to the subject's body, acquire a first 2D x-ray image of at least the portion of the tool and the skeletal portion from a first view;
be moved to a second pose with respect to the subject's body, and
while the 2D x-ray imaging device is at the second pose, acquire a second 2D x-ray image of at least the portion of the tool and the skeletal portion from a second view, and (b) subsequent to the portion of the tool being moved to a second location along the longitudinal insertion path with respect to the skeletal portion, acquire one or more additional 2D x-ray images from a single image view, the non-transitory computer software product comprising a non-transitory computer-readable medium in which program instructions are stored, which instructions, when read by a computer cause the computer to perform the steps of:

(a) receiving from the 3D imaging device the 3D image data;

(b) receiving from the 2D x-ray imaging device the first and second 2D x-ray images of at least the portion of the tool and the skeletal portion;

(c) registering the first and second 2D x-ray images to the 3D image data;

(d) identifying a location of the portion of the tool with respect to the skeletal portion, within the first and second 2D x-ray images;

(e) based upon the identified location of the portion of the tool within the first and second 2D x-ray images, and the registration of the first and second 2D x-ray images to the 3D image data, identifying the first location of the portion of the tool with respect to the 3D image data, (f) computing an anticipated longitudinal forward path of the tool within the 3D image data based on the first and second 2D x-ray images;

(g) receiving from the 2D x-ray imaging device the one or more additional 2D x-ray images of at least the portion of the tool and the skeletal portion; and (h) facilitating identifying whether the tool has deviated from the anticipated longitudinal forward path by:
registering the additional one or more 2D x-ray images to the 3D image data, such that the anticipated longitudinal forward path of the tool is registered with the additional one or more 2D x-ray images, and identifying a location of the portion of the tool with respect to the skeletal portion, within the additional one or more 2D x-ray images.

19. The non-transitory computer software product according to claim 18, wherein:

the instructions, when read by a computer cause the computer to further perform the step of, subsequent to registering the one or more additional 2D x-ray images to the 3D image data, overlaying the anticipated forward path of the tool on the one or more additional 2D x-ray images, and identifying whether the tool has deviated from the anticipated longitudinal forward path comprises comparing a position of the tool in the one or more additional 2D x-ray images with the anticipated longitudinal forward path overlayed on the one or more additional 2D x-ray images, the comparing comprising:

(a) a user visually comparing the position of the tool in the one or more additional 2D x-ray images with the anticipated longitudinal forward path overlayed on the one or more additional 2D x-ray images, or (b) the computer comparing the position of the tool in the one or more additional 2D x-ray images with the anticipated longitudinal forward path overlayed on the one or more additional 2D x-ray images, or (c) a combination of (a) and (b).

* * * * *